US012344891B2

(12) United States Patent
Howorka et al.

(10) Patent No.: US 12,344,891 B2
(45) Date of Patent: Jul. 1, 2025

(54) MEMBRANE BOUND NUCLEIC ACID NANOPORES

(71) Applicant: UCL Business Ltd, London (GB)

(72) Inventors: Stefan Howorka, London (GB); Yongzheng Xing, London (GB)

(73) Assignee: UCL Business Ltd, London (GB)

( * ) Notice: Subject to any disclaimer, the term of this patent is extended or adjusted under 35 U.S.C. 154(b) by 1187 days.

(21) Appl. No.: 17/265,244

(22) PCT Filed: Aug. 2, 2019

(86) PCT No.: PCT/GB2019/052181

§ 371 (c)(1), (2) Date: Feb. 2, 2021

(87) PCT Pub. No.: WO2020/025974

PCT Pub. Date: Feb. 6, 2020

(65) Prior Publication Data

US 2021/0301334 A1 Sep. 30, 2021

(30) Foreign Application Priority Data

Aug. 2, 2018 (GB) ...................................... 1812615

(51) Int. Cl.

*C12Q 1/6869* (2018.01)
*C12Q 1/6837* (2018.01)
*B82Y 5/00* (2011.01)

(52) U.S. Cl.

CPC ......... *C12Q 1/6869* (2013.01); *C12Q 1/6837* (2013.01); *B82Y 5/00* (2013.01)

(58) Field of Classification Search

CPC ................................................... C12Q 1/6869

See application file for complete search history.

(56) References Cited

FOREIGN PATENT DOCUMENTS

| | | | | |
|---|---|---|---|---|
| EP | 2695949 A1 * | 2/2014 | ............... | C12Q 1/68 |
| WO | 2017177047 A1 | 10/2017 | | |

OTHER PUBLICATIONS

Bell et al. "Nanopores formed by DNA origami: A review." FEBS Letters 588(19): 3564-3570 (2014).

Zheng et al. "Small circular DNA molecules act as rigid motifs to build DNA nanotubes." Journal of the American Chemical Society 136(29): 10194-10197 (2014).

* cited by examiner

*Primary Examiner* — Albert M Navarro

(74) *Attorney, Agent, or Firm* — Nixon Peabody LLP; David S. Resnick; Nicole D. Kling

(57) ABSTRACT

A membrane-spanning nanopore is provided, the nanopore comprising: a. one or more polynucleotide strands that provide a scaffold component; and b. a plurality of polynucleotide strands that provide a plurality of staple components; wherein each of the plurality of staple components hybridise to the scaffold component; wherein the orientation of a major portion of at least one polynucleotide strand comprised within the scaffold component is substantially parallel to a planar surface of a membrane as well as embedded within and substantially coplanar with the membrane; wherein the nanopore defines a channel that is suitable for perforating the membrane; the channel having a longitudinal axis extending along the centre thereof and a minimum internal dimension perpendicular to the longitudinal axis of at least about 3 nm. A membrane comprising the nanopore, biological sensors comprising the membrane and a method for molecular sensing using the membrane are also disclosed.

25 Claims, 11 Drawing Sheets

Specification includes a Sequence Listing.

(a)

(b)

(c)

(a)

(b)

MEMBRANE BOUND NUCLEIC ACID NANOPORES

CROSS-REFERENCE TO RELATED APPLICATIONS

This application is a 35 U.S.C. § 371 National Phase Entry Application of International Application No. PCT/GB2019/052181 filed Aug. 2, 2019, which designates the U.S. and claims benefit under 35 U.S.C. § 119(a) of G.B. Provisional Application No. 1812615.1 filed Aug. 2, 2018, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jan. 28, 2021, is named 2021-02-02-Sequence-Listing-051039-099590USPX.txt and is 169,443 bytes in size.

FIELD OF THE INVENTION

The invention is in the field of nucleic acid-based nanostructures that can insert into membranes and function as nanopores. Such nanopores may find utility in the fields of chemical and biological sensors, nanoscale devices and molecular gating applications.

BACKGROUND OF THE INVENTION

Nanopores are membrane spanning polymers and complexes that can define a perforation and thereby form a channel in a membrane that forms a partition between two fluids, typically liquids, suitably aqueous solutions, through which ions and certain molecules may pass. The minimum diameter of the channel is typically in the nanometre ($10^{-9}$ metre) range hence giving certain of these polypeptides the name 'nanopores'. The channel typically is formed in a perpendicular orientation relative to the planar axis of the membrane and can be formed from proteins, peptides, synthetic organic compounds or nucleic acids, such as DNA (Howorka, Nature Nanotech., 12, July; 619-630 (2017)).

Nanopores bound in membranes have many potential uses. One example is the use of nanopores as sensors to analyse biomolecules in a label-free and portable fashion. In an embodiment of this approach, an electrical potential is applied across a membrane-bound nanopore causing ions to flow through the channel. This flow of ions can be measured as an electrical current. Suitable electrical measurement techniques using single channel recording have been described, for example, in WO 2000/28312 and D. Stoddart et al., Proc. Natl. Acad. Sci., 2010, 106, 7702-7. Multi-channel recording techniques have also been described, for example, in WO 2009/077734 and International Application WO-2011/067559. Optical measurements may be combined with electrical measurements (Soni G V et al., Rev Sci Instrum. 2010 January; 81(1):014301). Alternatively flow of ions through the membrane-bound nanopore may be achieved by providing an ionic gradient across the membrane. A measured electrical current can be used to assess of the size or degree of obstruction of the channel. These changes in electrical current can be used to identify that a molecule, or part of a molecule, has bound at or near the pore (molecular sensing), or in certain systems, it can be used to determine the identity of a molecule that is present within the pore based on its size (nucleic acid sequencing). Strand sequencing of nucleic acids has been described in relation to several protein based nanopores such as for mutant MspA, Clya, alpha-hemolysin and also CsgG (see WO-2016/034591).

However, protein based nanopores are very difficult to handle and design de novo. They typically exhibit pore channels with narrow lumens (less than 5 nm) that can restrict their utility in diverse bio-sensing applications. The thermodynamics of folding can be complicated and result in misfolded proteins that do not insert into and bridge the membrane. To be useful as a sensor for folded proteins or other large biomolecules, suitable membrane channels formed by a nanopore should meet certain criteria, namely:

1) the channel lumen should be at least about 5 nm wide to accommodate the large biomolecule molecules inside the channel lumen; binding of the large biomolecule within the channel results in higher read-out sensitivity than when analytes bind at the pore entrance;
2) the pores should be structurally defined to attain a constant base level in the electrical read-out (i.e. reduce background noise); and
3) the pore dimensions should be easily tunable to adapt them to different biomolecule sizes.

To date none of the existing biological or engineered pores fulfil all of these criteria.

To address the limitations of protein-based nanopores researchers have sought to use nucleic acid-based systems. Pores composed of nucleic acid duplexes, in particular DNA duplexes, have been shown to be capable of forming stable nanopores of tunable internal width (Burns J. R., et al. Angew. Chem. Int. Ed. 52, 12069-12072 (2013); and Seifert A., Göpfrich K., Burns J. R., Fertig N., Keyser U. F., Howorka S. ACS Nano 9, 1117-1126 (2015)). The modular construction principle for DNA nanopores has enabled customized pore diameter (Göpfrich et al, Nano. Lett., 15(5), 3134-3138 (2015); WO 2013/083983) and installation of a controllable gate to regulate transport (Burns J. R., Seifert A., Fertig N., Howorka S. A., Nat. Nanotechnol. 11, 152-156 (2016)).

Membrane spanning nucleic acid nanopores are typically comprised of a structural core of a plurality of interlinked DNA duplexes that enclose a hollow channel, open at both ends. The technique of DNA origami can be used to create a stem that penetrates and spans a lipid membrane, whilst a barrel-shaped cap adheres to one side of the membrane and extends outwardly to form a funnel (Langecker et al., Science, November 16; 338(6109): 932-936 (2012)). In this way the nucleic acid nanopore mimics the configuration of analogous protein nanopores. However, a problem associated with such configurations for both protein and nucleic acid nanopores is that the molecules, such as analytes, can be subject to non-specific binding interactions with the walls defining the internal surface of the lumen or the entry or exit apertures of the nanopore. Such non-specific binding can lead to blockage of the channel of the pore, thereby reducing the efficiency, signal and working life of devices and sensors that comprise such pores.

A further consideration with nucleic acid nanopores that are comprised of a plurality of bundled duplexes is that they can be prone to ion leakage across the pore resulting in variations in measured current. Variation of this kind is undesirable and leads to a reduction in accuracy and fidelity of signal, with significantly increased background noise. Without wishing to be bound by theory, it is considered that the variations are due to loss of structural integrity in the nucleic acid duplex bundles which are subjected to planar membrane forces causing the bundles to separate briefly or become misaligned allowing current to flow through the gaps that are formed.

It is an object of the present invention to overcome or, at least, ameliorate the problems that exist in the prior art. These and other uses, features and advantages of the invention should be apparent to those skilled in the art from the teachings provided herein.

SUMMARY OF THE INVENTION

In a first aspect the invention provides for a membrane-spanning nanopore, the nanopore comprising:

a. one or more polynucleotide strands that provide a scaffold component; and b. a plurality of polynucleotide strands that provide a plurality of staple components;

wherein each of the plurality of staple components hybridise to the scaffold component;

wherein the orientation of a major portion of at least one polynucleotide strand comprised within the scaffold component is substantially parallel to a planar surface of a membrane as well as embedded within and substantially coplanar with the membrane;

wherein the nanopore defines a channel that is suitable for perforating the membrane;

the channel having a longitudinal axis extending along the centre thereof and a minimum internal dimension perpendicular to the longitudinal axis of at least about 3 nm.

In a specific embodiment of the invention either or both of the one or more polynucleotide strands that provide a scaffold component and at least one of the plurality of staple components further comprise at least one hydrophobic anchor that facilitates insertion of the nanopore into the membrane.

In another embodiment, the channel has a shape perpendicular to the longitudinal axis selected from the group consisting of: annular; elliptical; and polygonal In a specific embodiment of the first aspect of the membrane-spanning nanopore of the first aspect of the invention, the nanopore comprises:

a. one or more polynucleotide strands that provide a scaffold component; and b. a plurality of polynucleotide strands that provide a plurality of staple components;

wherein each of the plurality of staple components hybridise to the scaffold component;

wherein the orientation of a major portion of a polynucleotide strand comprised within the scaffold component is substantially parallel to a planar surface of a membrane as well as embedded within and substantially coplanar with the membrane, such that the nanopore thereby defines a channel that perforates the membrane, the central channel having a lumen that has a minimum internal width of at least about 3 nm.

In an embodiment, the membrane-spanning nanopore of the invention comprises one or more modules. Suitably, the nanopore further comprises sub-modules connected between the one or more modules. In embodiments, the or each module are the same such that the nanopore has rotational symmetry about the longitudinal axis of the channel. In further embodiments, the or each module is connected to at least one other module. Suitably, the connection between modules is provided by structures selected from the group consisting of: a staple strand or portion thereof of one of the modules; a scaffold strand or portion thereof of one of the modules; a sub-module; one or more polynucleotide strands that provide a spacer component.

In embodiments, the scaffold component of the membrane-spanning nanopore comprises at least a second polynucleotide strand, optionally at least second and third or more scaffold polynucleotide strands. Suitably, the polynucleotide strand of the one or more polynucleotide strands comprised within the scaffold component, and/or the plurality of polynucleotide strands comprised within the staple component, and/or the spacer component, when present, comprises DNA. Typically, the assembly of the nanopores of the invention and/or components thereof is via DNA origami techniques. In a particular embodiment of the invention the one or more scaffold components, assume a stacked ring configuration that is in a coplanar orientation with respect to the membrane into which the nanopore may be embedded. In an alternative embodiment, the one or more scaffold components, assume a side-by-side configuration that, each scaffold component in a coplanar orientation with respect to the membrane into which the nanopore may be embedded.

According to specific embodiments of the invention the at least one hydrophobic anchor is comprised of a hydrophobic portion of a polynucleotide strand comprised within the scaffold component. Alternatively or additionally, the at least one hydrophobic anchor may be comprised of at least one of the plurality of polynucleotide strands comprised within the staple component which includes a hydrophobic portion. Optionally, substantially all of at least one of the staple polynucleotide strands is hydrophobic and thereby defines a hydrophobic anchor.

In a specific embodiment the at least one hydrophobic anchor comprises at least one, suitably a plurality of hydrophobic anchor molecules. Suitably, the plurality of hydrophobic anchor molecules are:

a. attached to and spaced substantially equidistantly about the periphery of the nanopore, and wherein the plurality of hydrophobic anchor molecules are orientated radially outwardly from the longitudinal axis of the channel of the nanopore; and/or b. attached to a membrane-facing side of the nanopore or a portion thereof such that the plurality of hydrophobic anchor molecules are orientated to interact with and/or extend into the membrane once inserted.

In a further embodiment of the invention, the nanopore comprises at least three, optionally four, suitably at least five hydrophobic anchor molecules, and optionally six or more hydrophobic anchor molecules.

In embodiments of the invention the at least one hydrophobic anchor molecule is selected from: a lipid; and a porphyrin. Typically, when the anchor comprises a lipid, the lipid is selected from the group consisting of: sterols; alkylated phenols; flavones; saturated and unsaturated fatty acids; and synthetic lipid molecules (including dodecyl-beta-D-glucoside). In specific embodiments of the invention:

the sterols are selected from the group consisting of: cholesterol; derivatives of cholesterol; phytosterol; ergosterol; and bile acid;

the alkylated phenols are selected from the group consisting of: methylated phenols;

and tocopherols;

the flavones are selected from the group consisting of: flavanone containing compounds; and 6-hydroxyflavone;

the saturated and unsaturated fatty acids are selected from the group consisting of: derivatives of lauric acid; oleic acid; linoleic acid; and palmitic acids; and/or the synthetic lipid molecule is dodecyl-beta-D-glucoside.

According to specific embodiments of the invention the nanopore is in the form of a polygon selected from the group consisting of: a triangle; a square; a quadrilateral; a pentagon; a hexagon; a heptagon; and an octagon. It is typical, but not mandatory, that the minimum internal width of the lumen defined by the channel of the nanopore is greater than about 10 nm and less than about 20 nm.

In particular embodiments of the invention the scaffold component comprises at least one polynucleotide strand is comprised of a polynucleotide having the sequence selected from the group consisting of: SEQ ID NO: 1; SEQ ID NO: 2; SEQ ID NO: 13; and SEQ ID NO: 14. Optionally, the staple components are comprised of a plurality of polynucleotide strands comprising at least one polynucleotide having a sequence selected from the group consisting of: SEQ ID NOs: 3 to 12; SEQ ID NOs: 15 to 56; SEQ ID NOs: 65 to 94; SEQ ID NOs: 105 to 140; and SEQ ID NOs: 153 to 268.

In a specific embodiment of the invention, the membrane-spanning nanopore further comprises at least one linker, wherein at least a portion of the linker is located on or proximate to a surface of the channel, when the nanopore has assumed its three-dimensional configuration. Suitably, the linker is attached to an analyte binding molecule, and wherein the analyte binding molecule is thereby located within or proximate to the channel. Suitably, the linker is a polynucleotide strand. Suitably, the linker is attached to the analyte binding molecule via a covalent linkage, electrostatic interaction or via hydrogen bonding. In specific embodiments, the analyte binding molecule comprises a molecule selected from the group consisting of: an antibody, or an antigen binding fragment thereof, including a Fab fragment; a peptide aptamer; a microprotein; an affimer; and a nucleic acid aptamer. Optionally the linker is attached to a biomolecule that possesses a catalytic activity, such as an enzyme, for example a polymerase; a helicase; a gyrase; and a telomerase. In exemplary embodiments of the invention, the biomolecule is selected from an analyte binding polypeptide or nucleic acid.

A second aspect of the invention provides a membrane-spanning nanopore, wherein the nanopore is configured to form an annular or polygonal structure that is located within a membrane, the nanopore comprising:

i. at least one scaffold polynucleotide strand; and ii. a plurality of staple polynucleotide strands;

wherein each of the plurality of staple polynucleotide strands hybridises to the at least one scaffold polynucleotide strand to form a three-dimensional configuration of the membrane-spanning nanopore, wherein either or both of the at least one scaffold polynucleotide strand and the plurality of staple polynucleotide strands further comprises a plurality of hydrophobic anchor molecules, and wherein the membrane-spanning nanopore is positioned such that the orientation of a majority of the at least one scaffold polynucleotide strand is substantially parallel to the planar surface of the membrane and thereby defines a central channel with a minimum internal width of at least about 4 nm.

A third aspect of the invention provides a membrane, suitably a membrane comprising a hydrophobic bilayer or amphiphilic layer, into which is inserted at least one membrane-spanning nanopore as described in any aspect or embodiment exemplified herein. Typically the membrane comprises a semi-fluid membrane formed of polymers or a solid state membrane. Suitably, the semi-fluid membrane is composed of amphiphilic synthetic block copolymers, suitably selected from hydrophilic copolymer blocks and hydrophobic copolymer blocks. In an embodiment of the invention the hydrophilic copolymer blocks are selected from the group consisting of: poly(ethylene glycol) (PEG/PEO); and poly(2-methyloxazoline); and the hydrophobic copolymer blocks are selected from the group consisting of: polydimethylsiloxane (PDMS); poly(caprolactone (PCL); poly(lactide) (PLA); and poly(methyl methacrylate) (PMMA). In an alternative embodiment, the polymer membrane is composed of the amphiphilic block copolymer poly 2-(methacryloyloxy)ethyl phosphorylcholine-b-disisopropylamino) ethyl methacrylate (PMPC-b-PDPA). Optionally the membrane is, or comprises, a biological lipid bilayer membrane.

In a specific embodiment of the invention the membrane is in the form of a vesicle, a micelle, a planar membrane or a droplet.

In another embodiment, the membrane is a solid state membrane formed of a material selected from the group consisting of: Group II-IV and III-V oxides and nitrides, solid state organic and inorganic polymers, plastics, elastomers, and glasses.

A fourth and fifth aspect of the invention provides a biological sensor, wherein the biological sensor comprises at least one membrane as described herein and also apparatus for electrical or fluorescence measurement respectively. A further embodiment of the invention provides for a biological sensor that comprises a plurality of membrane-spanning nanopores comprised within one or more membranes.

A sixth aspect of the invention provides for a sensing device comprising one or more biological sensors as described herein. The sensing device may serve as a diagnostic or prognostic apparatus. The sensing device may comprise electrodes arranged on each side of the membrane in order to measure an ion current through an aperture/membrane perforation under a potential difference. The electrodes may be connected to an electrical circuit which includes a control circuit arranged to supply a voltage to the electrodes and a measurement circuit arranged to measure the ion flow. A common electrode may be provided to measure ion flow through the apertures between the common electrode and electrodes provided on the opposite side of the membrane.

A seventh aspect of the invention provides a method for molecular sensing comprising:

I. providing a membrane as described herein;

II. contacting the nanopore with an analyte and establishing a flow of ions through the at least one nanopore or an electron flow across the nanopore; and III. measuring an electrical signal across the nanopore, wherein the molecular sensing comprises analyte detection or characterisation, wherein a change in electrical measurement is indicative of the analyte.

In an embodiment of the present invention, the electrical measurement is selected from: a current measurement; an impedance measurement; a tunnelling measurement; and a field effect transistor (FET) measurement. Optionally, the electrical measurement comprises determining a flow of ions from a first side of the membrane to a second side of the membrane. Optionally, the method described comprises after step (III) the further step of determining the presence of the analyte by a change in ion flow or electron flow through or across the one or more membrane-spanning nanopores compared to the ion flow or electron flow through or across the one or more membrane-spanning nanopores when the analyte is absent.

In a eighth aspect of the invention, a method for molecular gating is provided, the method comprising:

a) Providing the membrane according to the third aspect of the invention;
b) Providing at least one biomolecule with a diameter of less than the minimum internal width of a channel in the nanopore; and
c) Incubating until the at least one biomolecule has passed through the nanopore.

In an embodiment of the eighth aspect of the invention, when at least one biomolecule has passed through the nanopore, it is subjected to a physical change that prevents it returning through the nanopore. In further embodiments, the at least one biomolecule is a globular protein, a polynucleotide-protein construct, a labelled polynucleotide or a labelled protein.

It will be appreciated that the invention may be defined by further combinations of several of the features disclosed herein but which are not explicitly recited above.

BRIEF DESCRIPTION OF THE DRAWINGS

The invention is illustrated by the accompanying drawings in which.

DETAILED DESCRIPTION OF THE INVENTION

Figure 1A:
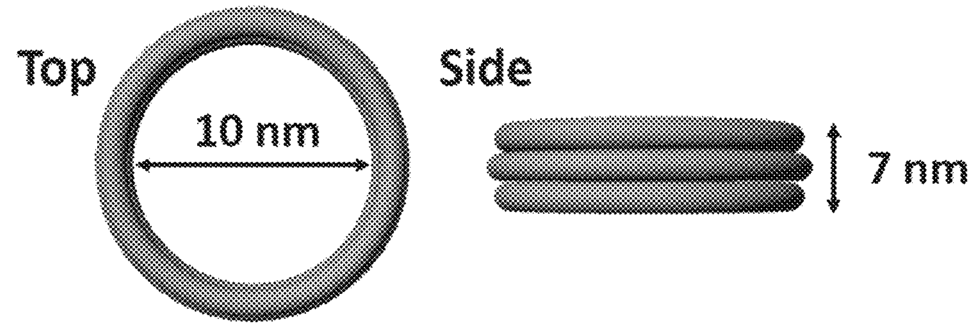
FIG. 1 (*a*) is a representation of a nucleic acid nanopore structure according to one embodiment of the invention showing a stacked ring-like configuration but omitting the presence of separate lipid anchors in top (plan) view showing the channel that defines a lumen of internal width of 10 nm and in side view; (b) is a representation of a nucleic acid nanopore structure according to one embodiment of the invention with a linker group and analyte binding agent (biotin) tethered within the channel defined by the pore; (c) shows a representation of a nucleic acid nanopore structure according to one embodiment of the invention showing the ring-like configuration with the presence of six membrane anchors extending radially outwardly in top (plan) and oblique view—denoted as r6c; and (d) is a representation of ring nanopores according to the embodiment of (a) which are inserted into a lipid membrane, thereby permitting the passage of analytes across the membrane via the channel of the nanopore.
Figure 1B:
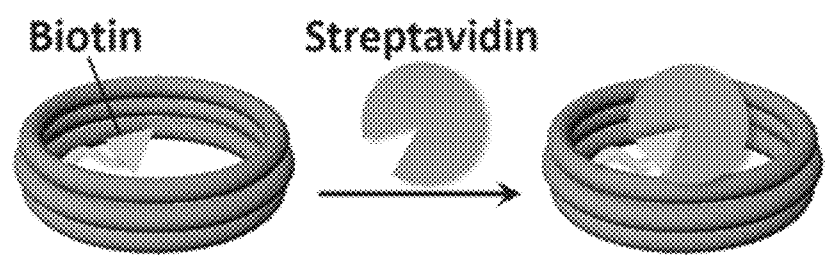

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term 'comprising' means any of the recited elements are necessarily included and other elements may optionally be included as well. 'Consisting essentially of' means any recited elements are necessarily included, elements that would materially affect the basic and novel characteristics of the listed elements are excluded, and other elements may optionally be included. 'Consisting of' means that all elements other than those listed are excluded. Embodiments defined by each of these terms are within the scope of this invention.

The term 'membrane' as used herein is an enclosing or separating selectively-permeable boundary, partition, barrier or film. The membrane has two sides or surfaces which may be named the cis and trans side respectively. The membrane is thin (i.e. has a thickness substantially less than its width and length) allowing it to be spanned by the nanopore. In the context of the present invention, the membrane thickness is the typically in the nanometre ($10^{-9}$ metre) range. The arrangement of the membrane is not limited and may assume any form, for example, a liposome, and a vesicle or as a planar or a non-planar sheet. Specific examples of membranes useful in the present invention include lipid bilayers, polymeric films, or solid state substrates.

The term 'solid state membrane' or 'solid state substrate' as used herein refers to a membrane formed from a solid state substance—i.e. not a semi-fluid membrane—in which one or more apertures are provided. One or more nanopores may be positioned within the respective one or more apertures disclosed for example in U.S. Pat. No. 8,828,211, hereby incorporated by reference. The solid state membrane may comprise either or both of organic and inorganic materials, including, but not limited to, microelectronic materials, whether electrically conducting, electrically semiconducting, or electrically insulating, including materials such as II-IV and III-V materials, oxides and nitrides, such as silicon nitride, $Al2O_3$, and $SiO_2$, Si, $MoS_2$, solid state organic and inorganic polymers such as polyamide, plastics such as Teflon®, or elastomers such as two-component addition-cure silicone rubber, and glasses. A membrane may be formed from monatomic layers, such as graphene, or layers that are only a few atoms thick such as those disclosed in U.S. Pat. No. 8,698,481, and U.S. Patent Application Publication 2014/174927, both hereby incorporated by reference. More than one layer of material can be included, such as more than one graphene layer, as disclosed in US Patent Application Publication 2013/309776, incorporated herein by reference. Suitable silicon nitride membranes are disclosed in U.S. Pat. No. 6,627,067, and the membrane may be chemically functionalized, such as disclosed in U.S. Patent Application Publication 2011/053284, both hereby incorporated by reference. Such a structure is disclosed for example in U.S. Pat. No. 8,828,211, hereby incorporated by reference. The internal walls of the apertures may be coated with a functionalised coating, such as disclosed in published application WO 2009/020682. The one or more apertures may be hydrophobic or provided with a hydrophobic coating to assist the provision of the one or more nanopores in the respective one or more apertures. Suitable methods for providing apertures in solid state substrates are disclosed in published applications WO 03003446 and WO 2016/187519.

The term 'modular' as used herein refers to the use of one or more units, or modules, to design or construct a whole or part of a larger system. In the context of the present invention it refers to the use of individual modules, sub-units or building blocks to construct a nanopore. The modules may be each the same or the modules may be different. To form the nanopore, the individual modules may be connected or inter-linked to one or more other modules. The means of connection between modules may be by chemical or physical means, such as covalent or non-covalent chemical bonding or by electrostatic or other attractive forces. Alternatively, or in addition, the means of connection may be via an additional module, bracing member, portion or linkage. The modular design of a nanopore may comprise a frame or framework of modules, and additional, typically smaller, sub-modules that connect, or support the frame, acting as struts or bracing members. The modules span the membrane to enable formation the channel of the nanopore; the sub-modules do not generally span the membrane and are intended only as structural support in the nanopore. The design of the modules and sub-modules, or how they connect, may be chosen to support and strengthen the formed channel of the nanopore such that it maintains its shape and conformational integrity when inserted in a membrane. The modules or sub-modules may be formed of nucleic acids, typically DNA. Each individual unit may be assembled by DNA origami techniques described elsewhere herein using suitably selected scaffold and staple strands. The individual modules may be joined by further DNA strands, or by direct bonding between the DNA strands of the individual modules. In some cases, the individual modules are arranged radially around a central axis, and thereby form, a channel. In other cases, the individual modules may be stacked on top of one another in a direction perpendicular to the plane of the membrane to form a tower or pile. In some instances, the tower or pile may be shaped in cross section such that the tower or pile forms a channel of sufficient length to span a membrane within which the nanopore is to be inserted. Any combination or arrangement of modules is envisaged such that they can form a channel that spans a membrane.

The term 'nucleic acid' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and are typically manufactured synthetically, but may also be isolated from natural sources. Nucleic acids may further include modified DNA or RNA, for example DNA or RNA that has been methylated or that has been subject to chemical modification, for example 5'-capping with 7-methylguanosine, 3'-processing such as cleavage and polyadenylation, and splicing, or labelling with fluorophores or other compounds. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Hence, where the terms 'DNA' and 'RNA' are used herein it should be understood that these terms are not limited to only include naturally occurring nucleotides. Sizes of nucleic acids, also referred to herein as 'polynucleotides' are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 100 nucleotides in length are typically called 'oligonucleotides'.

As used herein, the terms '3" ('3 prime') and '5" ('5 prime') take their usual meanings in the art, i.e. to distinguish the ends of polynucleotides. A polynucleotide has a 5' and a 3' end and polynucleotide sequences are conventionally written in a 5' to 3' direction. The term 'complements of a polynucleotide molecule' denotes a polynucleotide molecule having a complementary base sequence and reverse orientation as compared to a reference sequence.

The term 'duplex' is used herein refers to double-stranded DNA, meaning that the nucleotides of two complimentary DNA sequences have bonded together and then coiled to form a double helix. According to the present invention, homology to the nucleic acid sequences described herein is not limited simply to 100% sequence identity. Many nucleic acid sequences can demonstrate biochemical equivalence to each other despite having apparently low sequence identity. In the present invention homologous nucleic acid sequences are considered to be those that will hybridise to each other under conditions of low stringency (Sambrook J. et al, Molecular Cloning: a Laboratory Manual, Cold Spring Harbor Press, Cold Spring Harbor, NY).

As used herein, the term 'nanostructure' refers to a predesigned two or three dimensional molecular structure typically comprised from a biopolymer, suitably a naturally or non-naturally occurring nucleic acid, which structure has at least one dimension or an aspect of its geometry that is within the nanoscale (i.e. 10-9 metres). Nanoscale structures suitably have dimensions or geometry of less than around 100 nm, typically less than 50 nm, and most suitably less than 20 nm. Nanoscale structures suitably possess dimensions or geometry greater than around 0.1 nm, typically greater than around 1 nm, and optionally greater than around 2 nm. Assembly of nucleic acid nanostructures may occur spontaneously in solution, such as by heating and cooling a mixture of DNA strands of preselected sequences, or may require presence of additional co-factors including, but not limited to, nucleic acid scaffolds, nucleic acid aptamers, nucleic acid staples, co-enzymes, and molecular chaperones. Where desired nanostructures result from one or more predesigned spontaneously self-folding nucleic acid molecules, such as DNA, this is typically referred to as nucleic acid 'origami'. Rational design and folding of DNA to create two dimensional or three dimensional nanoscale structures and shapes is known in the art (e.g. Rothemund (2006) Nature 440, 297-302). In the classical scaffold-and-staple approach, one or more long biogenic scaffold strand component(s) is folded into a defined DNA nanostructure with a staple component consisting of shorter synthetic staple oligonucleotides. Classical DNA nanostructures are formed of bundles of parallel aligned DNA duplexes that are arranged into polygons that enclose a channel and puncture a membrane bilayer. However, a challenge with nucleic acid nanostructures remains that the strong net negative charge of the phosphodiester background hinders insertion into amphipathic and hydrophobic planar membranes. As a result, this has often favoured their use in solid state contexts, as nanofunnels attached to or sited within a nanoscale aperture in a substrate. A problem associated with such arrangements, however, is that they can often exhibit high levels of ionic leakage in sensor applications due to poor fit between the DNA duplex and the nanoscale aperture. Ionic leakage is much reduced when nanopores are embedded within semi-fluid membranes which surround the pore.

The nucleic acid sequences that form the nanostructures will typically be manufactured synthetically, although they may also be obtained by conventional recombinant nucleic acid techniques. DNA constructs comprising the required sequences may be comprised within vectors grown within a microbial host organism (such as *E. coli*). This would allow for large quantities of the DNA to be prepared within a bioreactor and then harvested using conventional techniques. The vectors may be isolated, purified to remove extraneous material, with the desired DNA sequences excised by restriction endonucleases and isolated, such as by using chromatographic or electrophoretic separation.

The term 'amino acid' in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=11e; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term 'amino acid' further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as 'functional equivalents' of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

A 'polypeptide' is a polymer of amino acid residues joined by peptide bonds, whether produced naturally or in vitro by synthetic means. Polypeptides of less than around 12 amino acid residues in length are typically referred to as 'peptides' and those between about 12 and about 30 amino acid residues in length may be referred to as 'oligopeptides'. The term 'polypeptide' as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term 'protein' is used herein to refer to a macromolecule comprising one or more polypeptide chains.

The term 'folded protein' as used herein refers to a protein that has acquired some three-dimensional shape after translation of the polypeptide chain from which it is formed (the primary structure). The term may refer to the secondary structure of the protein which is typically the first stage of the folding process where local three-dimensional structures are formed, for example, alpha helices or beta sheets. The term may more typically refer to the tertiary structure of a protein where the secondary structures of the protein have folded to stabilise the structure through hydrophobic or covalent interactions. The term also encompasses proteins having a quaternary structure where one or more protein subunits are assembled. As appropriate, the folded protein may also be termed the 'native' protein structure, and may be the form of the protein that exhibits its biological function.

The term 'interior width' when used herein refers to the straight distance spanning the interior of the channel (e.g. the lumen) from an interior face of one wall to an interior face of an opposing wall in a plane perpendicular to the longitudinal axis of the channel. The interior width of the channel may be constant along its longitudinal axis or it may vary due to the presence of one or more constrictions. The 'minimum interior width' is the minimum interior width along the longitudinal axis of the channel between an entrance and an exit of the channel. The minimum interior width of a channel defines the maximum size of an object, such as an analyte, that may pass through the channel.

As used herein the term 'hydrophobic' refers to a molecule having apolar character including organic molecules and polymers. Examples are saturated or unsaturated hydrocarbons. The molecule may have amphipathic properties.

As used herein, the term 'hydrophobically-modified' relates to the modification (joining, bonding or otherwise linking) of a polynucleotide strand with one or more hydrophobic moieties. A 'hydrophobic moiety' as defined herein is a hydrophobic organic molecule. The hydrophobic moiety may be any moiety comprising non-polar or low polarity aliphatic, aliphatic-aromatic or aromatic chains. Suitably, the hydrophobic moieties utilised in the present invention encompass molecules such as long chain carbocyclic molecules, polymers, block co-polymers, and lipids. The term 'lipids' as defined herein relates to fatty acids and their derivatives (including tri-, di-, monoglycerides, and phospholipids), as well as sterol-containing metabolites such as cholesterol. The hydrophobic moieties comprised within the embodiments of the present invention are capable of forming non-covalent attractive interactions with phospholipid bilayers, such as the lipid-based membranes of cells and act as membrane anchors for the nanopore. According to certain embodiments of the present invention suitable hydrophobic moieties, such as lipid molecules, possessing membrane anchoring properties may include sterols (including cholesterol, derivatives of cholesterol, phytosterol, ergosterol and bile acid), alkylated phenols (including methylated phenols and tocopherols), flavones (including flavanone containing compounds such as 6-hydroxyflavone), saturated and unsaturated fatty acids (including derivatives such as lauric, oleic, linoleic and palmitic acids), and synthetic lipid molecules (including dodecyl-beta-D-glucoside). The anchors for the polymer membrane may be the same as for lipid bilayers or they may be different. The specific hydrophobic moiety anchor may be selected based on the binding performance of the membrane chosen.

In an alternative embodiment of the invention, the hydrophobic modification is comprised within one or more synthetic nucleic acids (XNAs) incorporated into the nanopore structure itself.

The inventors have identified a structurally-defined wide-channel low profile organic nanopore. The structure of the nanopore renders it suitable for a number of uses in which a nanopore is positioned in a membrane that partitions two solutions. One such use is biomolecule sensing applications, in particular protein sensing applications where the folded protein may pass, bind or lodge within the pore. Modified versions of the nanopore may serve to further enhance the suitability of the channel for a particular folded protein or other biomolecule. Biomolecule sensing may be enhanced by the installation of a molecular receptor, binding molecule or enzyme within the pore lumen or channel.

The ability to create nanopores with controlled pore sizes and insert them into natural or synthetic membranes allows the construction of customised selectively-permeable membranes where control over the lumen dimensions, and optionally, other features of the pores enables control over which biomolecules are able to pass through these membranes. Of particular utility in the present invention is the increased control over internal width/size of the nanopores of the present invention that allows large biomolecules, including large globular proteins, to pass through such membranes. This has potential utility in medicine alongside other uses in the field of biology. For example, there are several large i.e. 10-30 nm diameter membrane pores that are either produced by immune cells to kill bacteria, such as in the 'complement system' (a part of the innate immune system that enhances (complements) the ability of antibodies and phagocytic cells to clear microbes and damaged cells from an organism, promotes inflammation, and attacks the pathogen's plasma membrane).

As an example, vesicles or microscale compartments formed of natural or synthetic polymers comprising nanopores according to the present invention may be used as nanoreactors. It is envisaged that substrate proteins or biomolecules may enter the vesicle interior through the nanopore where encapsulated enzymes in the interior of the vesicle enable a desired reaction to take place within the vesicle. As an example, encapsulated protease enzymes, such as trypsin may be retained inside a vesicle where the relatively large and controllable size of the nanopores could allow some substrate proteins but not others to enter for degradation, thereby protecting particular proteins from indiscriminate digestion. Similarly, control over the release of cargo contained within similar vesicles, such as protein or peptide based pharmaceutical agents would be possible with membranes with nanopores which allow passage of the cargo. Nanoreactors as described herein can be used in microfluidic biosynthetic processes and as part of lab-on-a-chip devices.

The nanopore according to an embodiment of the present invention a membrane-spanning nanostructure that is embedded within and, at least a portion thereof, is oriented substantially coplanar to a membrane. In an embodiment of the invention, the nanopore is located in a membrane in a manner akin to a grommet or eyelet mounted in a planar or curved sheet material. Hence, in a specific embodiment of the invention the nucleic acid nanostructure of the invention is defined as a nanoscale grommet or eyelet, this is irrespective of the shape of the channel(s) which may be circular or polygonal. A visual representation of one such arrangement is set out in FIG. 1 (*d*), where an embodiment showing a ring nanopore is shown embedded within a planar lipid membrane. According to this embodiment of the invention it is apparent that a majority of the nanostructure of the nanopore is embedded within the membrane compared to the proportion of the nanostructure extending outside of the membrane. This is in direct contrast to many previous nucleic acid nanopores.

Suitably the nanopores of the invention comprise one or more polynucleotide strands that provide a functional scaffold component, wherein the polynucleotide strands comprised within the scaffold component include a polynucleotide backbone; and a plurality of polynucleotide strands that provide a plurality of functional staple components. The scaffold strand(s) cooperate with and hybridise to the plurality of staple polynucleotide strands—e.g. via appropriate Watson-Crick base pairing hybridisation—in order to form a three-dimensional configuration of the nanopore. It is desirable that the nanopore assembles into an annular, elliptical or polygonal structure that is able to be embedded within a membrane such that a majority of the 5' to 3' orientation of the staple component(s) is coplanar with the membrane.

Suitably, the nanopores of the present invention are assembled via the 'scaffold-and-staple' approach. In this important route to DNA nanostructures, DNA is utilized as a building material in order to make nanoscale three dimensional shapes. Assembly of these complex nanostructures from a plurality of un-hybridized linear molecules is typically referred to as 'DNA origami'.

The DNA origami process generally involves the folding of the one or more elongate, 'scaffold' DNA strands into a particular shape using a plurality of rationally designed 'staple' DNA strands. The scaffold strand can have any sufficiently non-repetitive sequence. The sequences of the staple strands are designed such that they hybridize to particular defined portions of the scaffold strands and, in doing so, these two components cooperate force the scaffold strands to assume a particular structural configuration. Methods useful in the making of DNA origami structures can be found, for example, in Rothemund, P. W., Nature 440:297-302 (2006); Douglas et al, Nature 459:414-418 (2009); Dietz et al, Science 325:725-730 (2009); and U.S. Pat. App. Pub. Nos. 2007/0117109, 2008/0287668, 2010/0069621 and 2010/0216978, each of which is incorporated by reference in its entirety. Staple sequence design can be facilitated using, for example, CaDNAno software, available at http://www.cadnano.org.

In embodiments of the invention the staple and/or scaffold components further comprise a plurality of hydrophobic membrane anchor molecules that are attached thereto. The hydrophobic anchors (or portions of the sequence) facilitate insertion of the nanopore into a curved or planar membrane such that the orientation of a major portion of the first scaffold polynucleotide strand is substantially parallel to the surface of the membrane and wherein the first scaffold polynucleotide strand is embedded within and is substantially coplanar with the membrane. In referring to 'a major portion' of a scaffold polynucleotide stand it is meant that substantially more than 50%, suitably more than 60%, even greater than 70%, and as much as 90%, of the total length of that strand is orientated so that it is substantially coplanar with the membrane. In a specific embodiment the entire length of the scaffold strand, excepting crossovers and/or Holliday junctions necessary to impart three dimensional structure on a resultant nanopore, is orientated so that it is substantially coplanar with the membrane. It will be appreciated that DNA origami techniques allow for variations of the embodied structures that, nevertheless, fall within the overall design constraints of the recited nanostructures of the present invention. By way of example, the scaffold strand may be comprised of a plurality of shorter scaffold strands that, when assembled following hybridisation to appropriate staple strands, will cooperate to serve in a manner equivalent to a unitary single length scaffold strand.

Figure 8:
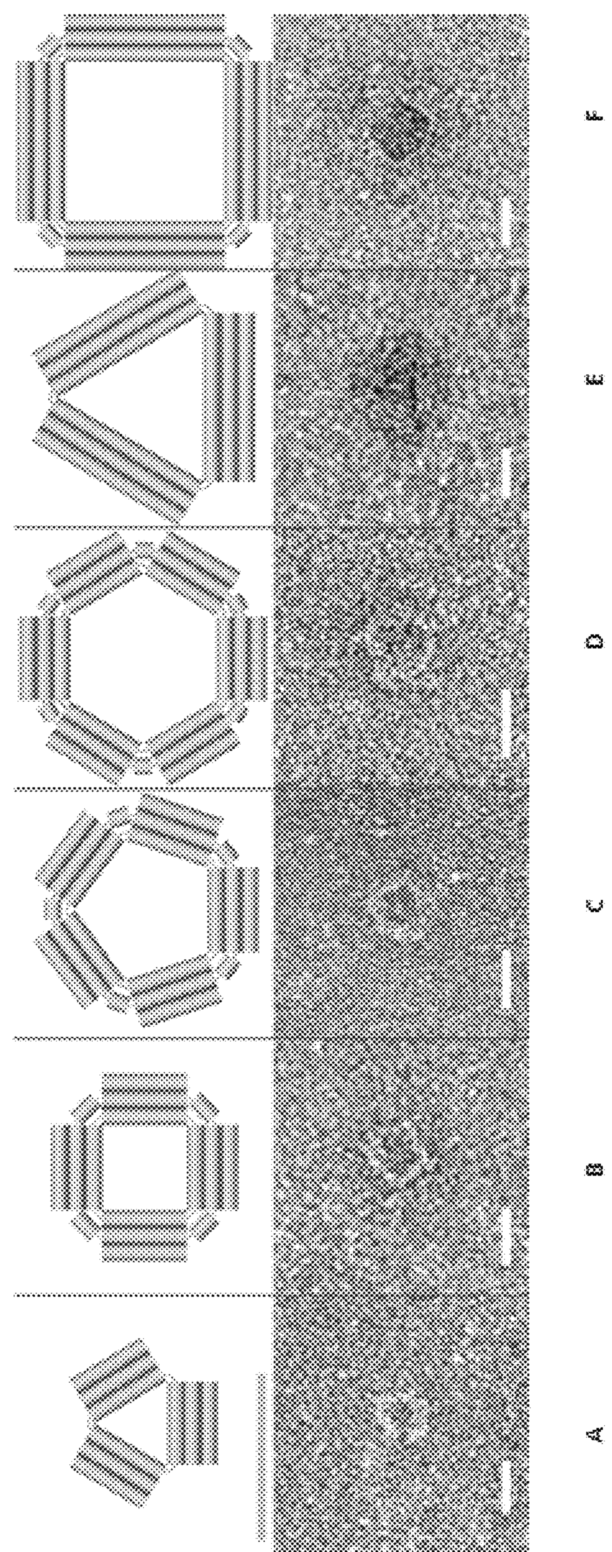
FIG. 8 shows schematic representations of the design of polygonal DNA nanopores and their exemplary TEM images. All scalebars are 20 nm in length.

In embodiments, the nanopores of the present invention are formed or constructed from one or more modules. In embodiments, the nanopore may be formed of an arrangement of modules that forms a basic frame or framework. In embodiments, the modules of the frame are supported by additional, typically smaller, sub-modules that connect and support the structure of the frame. At least part of the module is intended to form at least part of the channel wall of the nanopore and therefore the module is designed and configured to span a membrane in which it is inserted. Sub-modules are intended for structural benefits only and therefore are not intended or configured to span the membrane. While each module of the frame, or the sub-modules, may be different, suitably, the modules of the frame are suitably substantially or completely identical units, as are the sub-modules forming the support, when present. In these embodiments, the modules and sub-modules are each formed of the same scaffold and staple DNA structure and assembled in the same way. The individual modules may be joined by DNA strands, the DNA strand either being integral with the module, or hybridised to each module. While any arrangement of the modules is contemplated, suitably, for circular or elliptical cross-section nanopores, the modules may be arranged to overlie each other to form a generally hollow stack or tower thereby forming a channel. Suitably, for nanopores having a polygonal cross-section, the modules are arranged such that they sit side by side in the plane of a membrane. A combination of the above arrangements is also contemplated. The modules may have tuneable side length (a side length in this context being defined as the longest dimension of the module parallel to the plane of the membrane), which when chosen with an appropriate final overall shape, allows for different sized and/or shaped nanopores, and different sized and/or shaped lumens within the channels of those pores to be prepared. The channels and the lumens defined thereby may be regularly or irregularly shaped. For example, the lumens defined by the channel may be a regular or irregular circle or polygon, such as a triangle, a quadrilateral (e.g. a square, a rectangle or a trapezoid), a pentagon, a hexagon, a heptagon, an octagon and so on. Alternatively, the channels may be an elongate circle (ellipse) or elongate polygon, such as rectangular, oblong or slot-shaped channels formed of 4 or more sides. Typically, the side length of the modules would be in the order of between 10 nm and 20 nm (FIG. 8). Suitably, the side length of the modules may be at least 2 nm, 3 nm, 4 nm, 5 nm, 6 nm, 7 nm, 8 nm, 9 nm or 10 nm, Suitably the side length of the modules may be at most 30 nm, 25 nm, 20 nm. The sizing of the sub-modules is determined by the spacing between the modules which is turn is determined by the shape of the pore and the size and number of modules employed. Suitably, the side length of the modules may be at least 0.5 nm, 1 nm, 1.5 nm, 2 nm, 2.5 nm, 3 nm, 3.5 nm, 4 nm or 5 nm, Suitably the side length of the modules may be at most 10 nm, 7.5 nm, or 5 nm.

As used herein, the term 'substantially' refers to the complete or nearly complete extent or degree of an action, characteristic, property, state, structure, item, or result. For example, an object that is 'substantially' coplanar with another object would mean that the object is either completely coplanar or nearly completely coplanar, perhaps varying by a few degrees of variation from complete conformity. The exact allowable degree of deviation from absolute completeness may in some cases depend on the specific context, as would be understood to the person of skill in the art. However, in general terms the nearness of conformity to the absolute will be such as to have the same overall result—e.g. functional equivalence—as if total conformity were achieved.

The three-dimensional configuration of the nanopores of the present invention defines at least one channel, suitably a single channel that spans the membrane, the channel having a lumen that has a minimum internal width of at least about 3 nm. Suitably, the nanopores of the present invention have a single channel located at least substantially centrally in the pore structure when viewed perpendicular to the plane of the membrane in which the pore is intended to reside. The channel defines the lumen that passes through the nanopore which is perpendicular to the planar axis defined by the membrane. The cross-sectional profile of the lumen parallel to the plane of the membrane may be circular, ellipsoid or polygonal and may vary in terms of the internal dimensions. Suitably, the channel has a consistent internal cross-sectional profile and size for its entire length. Suitably, the cross-sectional profile of the channel is a circle or a quadrilateral, typically a square, rectangle or trapezoid. The minimum opening of the channel in this cross-section (i.e. minimum constriction) is suitable to allow access for a folded protein or other analyte. Typically, the minimum opening is at least 3 nm, 6 nm, 6.5 nm, 7 nm, 7.5 nm, 8 nm, 8.5 nm, 9 nm, 9.5 nm, 10 nm, 11 nm, 12 nm, 13 nm, 14 nm, or 15 nm or more. Suitably the lumen is between around 10 nm and around 20 nm in width. The maximum opening of the channel is limited only by the need to maintain structural integrity of the pore and to obtain an electrical read-out when a molecule of interest passes through. Suitably, the maximum opening of the channel (i.e. minimum constriction) is at most 200 nm, 150 nm, 100 nm, 75 nm, 50 nm, 40 nm, 30 nm, 20 nm, 18 nm, 15 nm, 12 nm, or 10 nm. Suitably, the cross-sectional area of the minimum opening of the channel (i.e. minimum constriction) is at least 5 $nm^2$, 12 $nm^2$, 15 $nm^2$, 25 $nm^2$, 35 $nm^2$, 40 $nm^2$, 45 $nm^2$ or 50 $nm^2$ or more. Suitably, the cross-sectional area of the minimum opening of the channel (i.e. minimum constriction) is at most 35 000 $nm^2$, 25 000 $nm^2$, 15 000 $nm^2$, 10 000 $nm^2$, 5 000 $nm^2$, 1500 $nm^2$, 1000 $nm^2$, 750 $nm^2$, 500 $nm^2$, 250 $nm^2$, 100 $nm^2$, 50 $nm^2$, 30 $nm^2$, 20 $nm^2$ or 15 $nm^2$, 10 $nm^2$, 7 $nm^2$ or less.

To achieve optimum performance, the variation in the channel size should be minimized from pore to pore. Even small variations in cross sectional area can lead to a significant discrepancy in ion flow through a given pore, both in the open state (devoid of any target analyte), or in the bound state (with target analyte present in, or proximate to, the channel). Such variation in ion flow leads to a lower signal to noise ratio in the electrical read-out thereby reducing the sensitivity of detection. The nanopores according to the present invention can have low variability in pore size if desired.

As mentioned, in embodiments of the present invention the nanostructures may comprise a channel that has a consistent internal profile and size (i.e. lumen width) for its entire length. However, for certain sensing applications it may be advantageous for the lumen width to vary along the length of the channel with one or more internal constrictions introduced. Such constrictions may be engineered using the same DNA origami techniques that are used in order to design the nanostructure as a whole. Alternatively, constrictions may be added post hoc by way of chemical modification or binding of a blocking molecule to effect a constriction. The introduction of one or more constrictions may affect the kinetics of ion and analyte flow through the nanopore in a similar way to the creation of a funnel.

The nanopore of the present invention may comprise two or more membrane anchors that act to attach or connect or anchor the hydrophilic DNA nanopore to the generally hydrophobic membrane (lipid bilayer or polymer). The lipid anchors are attached to the pore. Suitably attachment is via DNA oligonucleotides that carry the lipid anchor, suitably cholesterol, at the 5' or 3' terminus. Polynucleotides or oligonucleotides may be functionalized using a modified phosphoramidite in the strand synthesis reaction, which is easily compatible for the addition of reactive groups, such as cholesterol and lipids, or attachment groups including thiol and biotin. Enzymic modification using a terminal transferase can also be used to incorporate an oligonucleotide, which incorporates a modification such as an anchor, to the 3' of a single stranded nucleic acid (e.g. ssDNA). These lipid modified anchor strands may hybridize via 'adaptor' oligonucleotides to corresponding sections of the DNA sequence forming the scaffold section of the pore. Alternatively, the lipid anchors are assembled with the pore using lipid-modified oligonucleotides that contribute as either the scaffold or staple strands. A combination of approaches to anchoring using two or more membrane anchors may also be adopted wherein anchors are incorporated into one or all of a scaffold strand, a staple strand and an adaptor oligonucleotide.

Cholesterol has been found to be a particularly suitable lipid for use as an anchor in the present invention. The use of other lipids as anchors is contemplated, although it may be expected that there is a particular preference for a particular lipid, and a given number of membrane anchors, for a given membrane.

In a particular embodiment of the invention the membrane anchors are positioned around the periphery of the nanopore (i.e. away from the channel) such that they may extend radially outwardly from the nanostructure and interact with the amphipathic membrane that surrounds and encloses the nanostructure. In an alternative embodiment, the membrane anchors are positioned on a membrane-facing surface of the nanopore such that they may extend radially outwardly from the nanostructure and interact with the amphipathic membrane that surrounds and encloses the nanostructure. Suitably the plurality of membrane anchors are positioned substantially equidistantly about the periphery of the nanostructure. In this way insertional forces may be distributed more evenly about the outer periphery of the nanopore. By way of example, where two membrane anchors are used they will be spaced about 1800 from each other; where three membrane anchors are used spacing between each is about 120°; for four membrane anchors spacing is around 90°; for five membrane anchors spacing is around 72°; for six membrane anchors spacing is around 60°; and for seven spacing is around 52°. It will be appreciated that the spacing will diminish accordingly for greater number of membrane anchors.

In an alternative embodiment of the invention where the hydrophobic modification is comprised within one or more synthetic nucleic acids (XNAs) incorporated into the nanopore structure, one or more of the scaffold and/or staple strands may be fully or partially comprised of a synthetic nucleic acid analogue. Advantageously, the presence of hydrophobic synthetic nucleic acids enables the nanopore to interact and embed within a membrane. In such an embodiment the presence or one or more additional hydrophobic membrane anchor molecules may be unnecessary, with the requisite level of hydrophobic membrane anchoring capability comprised within the backbone of the nanostructure itself. Hybrid structures comprising a combination of hydrophobic synthetic nucleic acids together with lipid-based membrane anchors are also contemplated as part of the invention.

The membrane in which the nanopore of the present invention may be inserted may be of any suitable type. Depending on the intended use, the membrane may be a lipid bilayer or a polymer sheet or film. The membrane is suitably an amphiphilic layer. The amphiphilic layer may be a monolayer or a bilayer. An amphiphilic layer is a layer formed from amphiphilic molecules which have both hydrophilic and lipophilic properties. The amphiphilic molecules may be synthetic or naturally occurring. The lipophilic properties of the molecules comprising the membrane promote anchoring by lipid anchors or other hydrophobic anchoring regions of the nanopore. It is surprising that nucleic acid nanostructures of the invention are able to be inserted successfully into membranes at all given that the hydrophobic nature of the membrane leads to repulsion of the predominantly negatively charged DNA backbone. It might be expected that the nanostructures of the invention would simply form clustered aggregates on one surface of the membrane as is often the case with complex nucleic acid nanostructures that fail to insert successfully into an amphiphilic mono- or bilayer. The ability of the nanostructures to be embedded within such membranes is, therefore, surprising and most unexpected.

In a specific embodiment of the invention the amphiphilic layer may be a lipid bilayer. The lipid composition may comprise naturally-occurring lipids such as phospholipids and bipolar tetraether lipids, and/or artificial lipids. The lipids typically comprise a head group, an interfacial moiety and two hydrophobic tail groups which may be the same or different. Suitable head groups include, but are not limited to, neutral head groups, zwitterionic head groups, negatively charged head groups and positively charged headgroups. The head group or the tail group of the lipids may be chemically-modified.

It is envisaged that nanopores according to the present invention may be inserted into a membrane of a target cell or vesicle to facilitate translocation of specific folded proteins across the membrane. The specificity of the translocation to certain folded proteins may be controlled through variation of the size of the channel in the nanopore.

Proprietary and non-proprietary synthetic polymer films or sheets are widely used in 'chip-based' nanopore sequencing and analytical applications such as the MinION® system sold by Oxford Nanopore Technologies®; the GS FLX+® and the GS Junior® System sold by Roche®; the HiSeq®, Genome Analyzer IIx, MiSeq® and the HiScanSQ® systems sold by Illumina®; the Ion PGM® System and the Ion Proton System® sold by Life Technologies; the CEQ® system sold by Beckman Coulter®; and the PacBio RS® and the SMRT® system sold by Pacific Biosciences®. The ability of nanopores to insert successfully into polymer membranes of this type allows these systems to be adapted for diverse folded protein sensing applications, for example.

Non-naturally occurring amphiphiles and amphiphiles which form an amphiphilic membrane layer are known in the art and include, for example, block copolymers (Gonzalez-Perez et al., Langmuir, 2009, 25, 10447-10450). The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane may be chosen one of the membranes disclosed in PCT/GB2013/052767, hereby incorporated by reference in its entirety. The amphiphilic molecules may be chemically-modified or functionalised to facilitate coupling an insertion of the nanostructure. The membrane can comprise both a lipid and an amphiphilic polymer such as disclosed in PCT/US2016/040665.

Polymer-based membrane may be formed of any suitable material. Typically, synthetic membranes are composed of amphiphilic synthetic block copolymers. Examples of hydrophilic block copolymers are poly(ethylene glycol) (PEG/PEO) or poly(2-methyloxazoline), while examples of hydrophobic blocks are polydimethylsiloxane (PDMS), poly (caprolactone (PCL), poly(lactide) (PLA), or poly(methyl methacrylate) (PMMA). In embodiments, the polymer membrane used may be formed from the amphiphilic block copolymer poly 2-(methacryloyloxy)ethyl phosphorylcholine-b-disisopropylamino) ethyl methacrylate (PMPC-b-PDPA). DNA nanopores may be inserted into the walls of such polymersomes through incubation. Without wishing to be bound by theory, it is believed that one process of insertion broadly involves first steps of membrane tethering, followed by second steps of orientation of the DNA pore relative to the membrane to achieve complete insertion. This however requires lipid membrane anchors to be comprised within, or at least attached to, the pores, without which insertion does not take place. For alternative configurations of the invention, particularly where nucleic acid analogues (e.g. XNAs) comprise some or all of the backbone of the scaffold and/or staple strands, it is envisaged that more complex insertional dynamics may be observed. It will be appreciated that where the scaffold and staple strands incorporate synthetic biopolymer backbone constituents capable of mediating a hydrophobic interaction with a membrane, the insertion process may or may not involve initial stages of coplanar alignment with the membrane followed by a phase of insertion.

The membrane is typically planar, although in certain embodiments it may be curved or shaped. Amphiphilic membrane layers may also be supported. Suitably the membrane is a lipid bilayer or monolayer. Methods for forming lipid bilayers are known in the art such as disclosed in International Application Number PCT/GB2008/000563. Lipid bilayers are commonly formed by the method of Montal and Mueller (Proc. Natl. Acad. Sci. USA., 1972; 69: 3561-3566).

In another embodiment of the invention, the membrane may comprise a solid state layer. Solid state layers can be formed from organic and/or inorganic materials including, but not limited to, microelectronic materials, insulating materials such as $Si_3N_4$, Al2$O_3$, and SiO, glasses, organic and inorganic polymers such as polyamide and plastics. The solid state layer may be formed from graphene such as disclosed in PCT/US2008/010637. The membrane may be provided with one or more apertures or through-holes of nanometre scale dimensions extending from one side of the membrane to the other. The internal walls of the solid state aperture may be coated with a lipid such as disclosed in US2017/0023544 or chemically functionalized such as disclosed in PCT/US2008/063066, so as to facilitate suitable anchoring of the nanostructures of the invention to the solid state layer.

The ability to adapt the nanopores of the present invention such that they may be inserted into membranes of varying thickness is a significant advantage. In embodiments of the invention one or more scaffold strands may be utilised to form a coil or stacked ring structure in order to vary the depth of the pore and, thus, its ability to be adapted to span membranes of a given thickness (as shown in FIG. 1). In any case, a significant advantage of the nanopores of the present invention is that length of the channel is not required to be considerably greater than the width of the membrane. This ensures that non-specific binding of analyte to the interior walls of the channel is reduced. In addition, the time taken for ions to traverse the membrane, via the pore, is reduced leading to faster readouts.

A further advantage of the nanostructures of the present invention is that they are more structurally stable compared to nucleic acid nanopores that are comprised of a plurality of bundled duplexes that are oriented perpendicularly to the plane of the membrane. As mentioned previously, structural instability due to planar membrane pressures can lead to ion leakage across the pore, reducing accuracy and fidelity of signal, and significantly increasing background noise in sensors that comprise such nanopores. The nanostructures of the present invention are more resistant to the compressive membrane pressures leading to improved structural integrity, greater consistency of pore diameter (i.e. homogeneity of pores and signal) and reduced ion leakage.

In a specific embodiment of the present invention the nanostructures of the invention comprise a membrane spanning nanopore which is functionalised by addition of one or more target molecule binding moieties. The one or more target binding moieties may be placed on one or more modules of the nanopore. There may be one or more binding moieties placed on a single module of the nanopore, or alternatively, there may be one or more binding moieties placed on a different module of the nanopore. The simplicity of functionalising individual modules of the nanopore provides a particular advantage that a specific arrangement or number of binding moieties may be provided on the nanopore allowing more control and efficiency of binding of a target module than offered by prior art nanopores. It is envisioned, for example, that specific binding moieties may be positioned on opposite sides of the opening of the channel to ensure that when a target is captured it more effectively blocks flow through the channel.

The target may comprise an analyte in solution or a molecule that is capable of generating a detectable signal, such as a fluorophore or radiolabel. Binding of the analyte will serve to fully or partially occlude the channel of the nanopore such that a detectable electrical readout can be obtained. The target molecule binding moiety may be comprised within or attached to one or more polynucleotide strands that contribute to the formation of the nanopore, or alternatively added post hoc by binding to an exposed thiol group or biotin tag (via avidin or an analogue thereof) incorporated within the one or more polynucleotide strands. The binding moiety may comprise a polynucleotide or a polypeptide that is capable of binding to an analyte present in a solution that surrounds the membrane-embedded nanopore. Where the binding molecule comprises a polypeptide that is tethered to the nanopore, either within the channel or proximate to the cis or trans side of the nanopore, it may be selected from one of the group consisting of:

I. an enzyme—including a polymerase, a helicase, a gyrase, and a telomerase, as well as nucleic acid binding sub domains or derivatives thereof
II. synthetic or naturally derived affinity binding proteins and peptides—including affimers, antigen binding microproteins, engineered multiple repeat proteins, ankyrin binding domains, lactoferrins, cathelicidins, ficolins, collagenous lectins, T-cell receptor domains and defensins;
III. an antibody—including polyclonal, monoclonal, humanized and camelid antibodies, or antigen binding fragments and derivatives thereof, including Fab, scFv, Bis-scFv, VH, VL, V-NAR, VhH or any other antigen-binding single domain antibody fragment;
IV. synthetic or naturally derived affinity binding nucleic acids and nucleic acid analogues, including oligonucleotide probes, aptamers and ribozymes;
V. naturally occurring or synthetic small molecules, including drugs, fluorophores, metabolites and chemokines; and
VI. signalling molecules and/or polypeptide receptors thereof, including binding domains of receptors, and receptor complexes.

The nanopore structures of the present invention are suited to use in sensor applications that allow for the detection of a diverse range of potential analytes that may exist in a solution that is under test. Exemplary analytes may include:

peptides/polypeptides/proteins—folded, partially/completely unfolded;
enzymes;
protein/nucleic acid constructs;
molecules defined by size;
macromolecules within specified size ranges, for example, in ranges selected from: 1-10 kD, 1-50 kD, 1-100 kD, 10-50 kD, 10-100 kD, 20-50 kD, and 20-100 kD;
multi-protein complexes;
antigens;
glycoproteins;
carbohydrates;
biopolymers;
toxins;
metabolites and by products thereof;
cytokines;
nucleic acids.

The nanopore structures of the present invention may be incorporated within a plurality of improved devices and sensors. Such devices and sensors are useful in applications requiring to sensing and characterization of a variety of materials and analytes. By way of non-limiting example, particularly useful applications, including genome sequencing, protein sequencing, other biomolecular sequencing, and detection of ions, molecules, chemicals, small molecules, biomolecules, metal atoms, contaminants, polymers, nanoparticles etc. Such detecting and characterizing can, in turn, be used to diagnose diseases, in drug development, to identify contamination or adulteration or food or water supplies, and in quality control and standardization.

According to exemplary embodiments of the present invention as described, a sensor device typically comprises a substrate that includes a membrane into which one or more nanopores are embedded. The substrate is placed to facilitate contact with a fluid (optionally an electrolytic solution) which comprises an analyte. At least one, and optionally a plurality of, device(s) are positioned relative to the substrate, wherein a given device generates a signal (e.g. mechanical, electrical, and/or optical) in response to detecting binding to and/or passage through the nanopore(s) of one or one or more analytes. The plurality of devices can be greater than 2 and as many as 100, or as many as 20, or as many as 10, or between 2 and 8 devices. Each device may be selected from one or more of the group consisting of: a field effect sensor; a plasmonic sensor; a laser based sensor; an interferometric sensor; a wave-guide sensor; a cantilever sensor; an acoustic sensor; a quartz crystal microbalance (QCM) sensor; an ultrasonic sensor; a mechanical sensor; a thermal sensor; an optical dye based sensor; a fluorimetric sensor; a calorimetric sensor; a luminometric sensor; a graphene sensor; a quantum dot sensor; a quantum-well sensor; a photoelectric sensor; a 2D material sensor; a nanotube or nanowire sensor; an enzymatic sensor; an electrochemical sensor, including a FET or BioFET sensor; a potentiometric sensor; a conductometric sensor; a capacitive sensors; and an electron-spin sensor. The devices may cooperate in the form of arrays allowing for multiplexed testing of multiple analytes. The sensor devices may further comprise special purpose hardware and systems (e.g., circuitry, processors, memory, GUIs etc.) that perform the specified functions or acts, or combinations of special purpose hardware and computer instructions, in order to render a functioning sensor device capable of providing a meaningful readout to a user.

Hence, according to embodiments of the invention suitably configured nanopore devices may enable a variety of different types of sensor measurements to be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

The invention is further illustrated by the following non-limiting examples.

EXAMPLES

Example 1

Construction of Nucleic Acid Planar Ring Nanopore

Figure 1C:
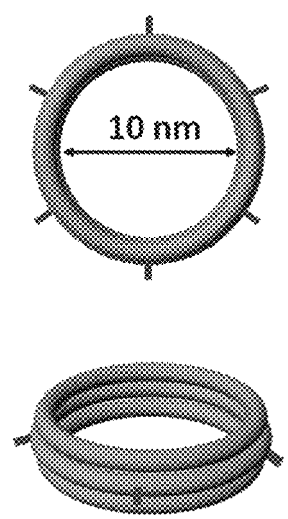
Figure 1D:
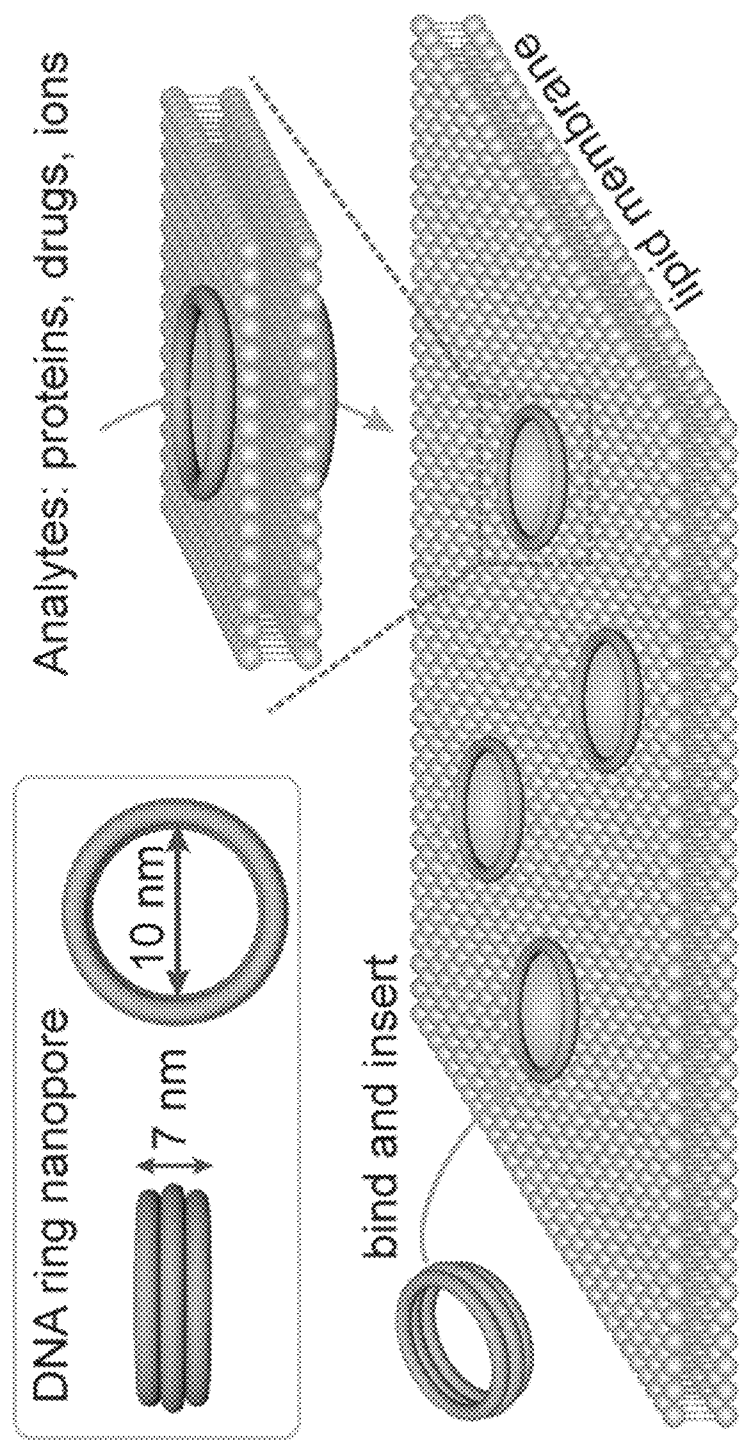

This nanostructure design was aimed at creating a novel large nanopore (FIG. 1*a*) that can embed in a semi-fluid lipid membrane and specifically permit the selective passage of analyte (FIG. 1*b*) and ions through the membrane barrier. To enable the insertion of the negatively charged DNA nanopore to the lipid bilayer, hydrophobic cholesterol tags were also incorporated at selected positions in the structure—in this case at six positions equally spaced around the periphery of the nanopore (FIG. 1*c*).

The main structure body was composed of DNA molecules which were designed with the aid of the caDNAno software (see above) and then rationally modified to fulfil both the structural and functional needs.

Figure 2:
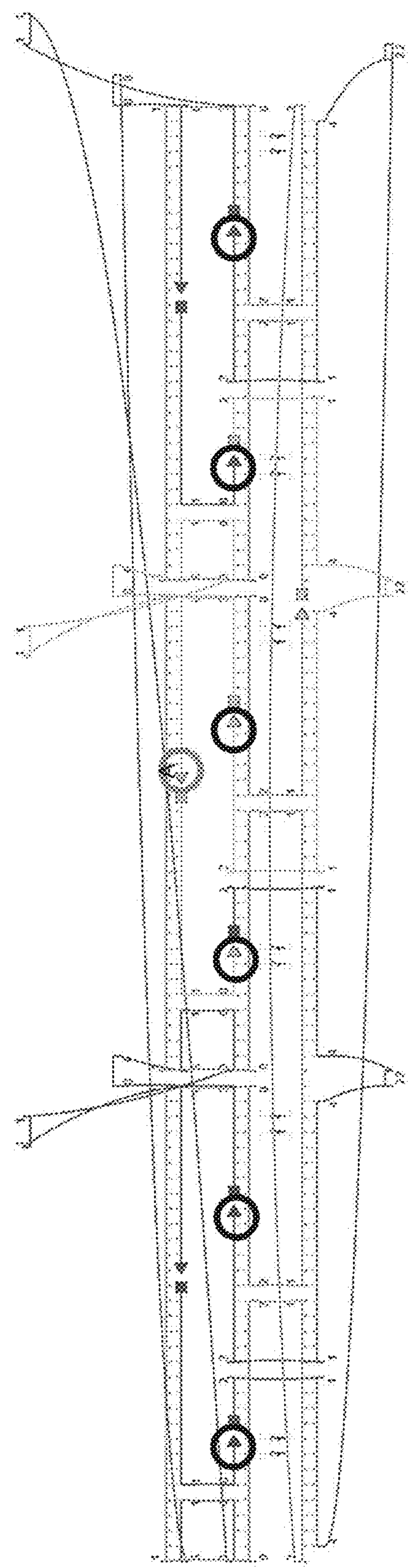
FIG. 2 shows a 2D DNA map of an r6c ring nanopore according to one embodiment of the present invention (the sequences of which are set out in Example 1). The scaffold strand is shown in medium grey and is a longer continuous strand, whereas the staple strands are in dark grey and are much shorter in length. 5' and 3' termini of DNA strands are represented as a squares and triangles, respectively. The circles around the 3' termini along the central axis indicate placement of the anchor molecules. The circle marked (A) identify the 3' terminus where a linker/analyte interacting molecule/functionalising molecule is attached.

As shown in FIG. 2, the structure was composed of one long scaffold and nine short staple strands. The long scaffold serves as a template for the assembly of the structure, and its laypath defines the overall shape and size of the nanopore. The short staples were modified with cholesterol tags, fluorophores and biotin moieties, with the functionalization achieved through the folding process.

As shown in FIGS. 1 and 2, the minimal design principle of the pore structure avoided extra parts, modifications or extraneous additions to the overall structure. Notably, the design of the pore was minimized to only have the 10 nm wide transmembrane portion and its 7 nm height defined by the three DNA duplexes was only slightly greater than the thickness of the lipid bilayer (5 nm). This novel design possesses many advantages over all the existing conventional pores based on large DNA capped origami structures. In particular, the current design enhances stability of the nanostructure by reducing electrostatic repulsion within the structure leading to considerably reduced folding times. In certain instances, folding times of a few hours are observed rather than the conventional expectation of several days.

TABLE 1

| Scaffold strands for nucleic acid planar ring nanopore: | |
|---|---|
| S1 (SEQ ID NO: 1) | TGATAGACGGTTTTTCGCCCTTTGACGTTGGAGTCCACGTTCTTTAATAGTGGACTCTTGTTCCAAACTGGAACAACACTCAACCCTATCTCGGGCTATTCTTTTGATTTATAAGGGATTTTGCCGATTTCGGAACCACCATCAAACAGGATTTTCGCCTG |
| S2 (SEQ ID NO: 2) | CTGGGGCAAACCAGCGTGGACCGCTTGCTGCAACTCTCTCAGGGCCAGGCGGTGAAGGGCAATCAGCTGTTGCCCGTCTCACTGGTGAAAAGAAAAACCACCCTGGCGCCCAATACGCAAACCGCCT |
| L (SEQ ID NO: 3) | GGTTTGCCCCAGCAGGCGAAAATCC |

Strand S2 was 5'-phosphorylated.

TABLE 2

| Staple strands for nucleic acid planar ring nanopore: | |
|---|---|
| R1 (SEQ ID NO: 4) | CACCAGTGAGACGGATTG |
| R2 (SEQ ID NO: 5) | AGTCCACTATTAAATCCA |
| R3 (SEQ ID NO: 6) | ATCCTGTTTGATGGATCG |
| R4 (SEQ ID NO: 7) | GCAAAAATCAAAAGAATTGCCCGAGATAGGGGGCGACAAAGTTGAGT |
| R5 (SEQ ID NO: 8) | ACGTAAAACCGTCTATTTAGGCGGTTTGCGTGCCTGTCACCATTGGG |
| R6 (SEQ ID NO: 9) | CCCTGCCCTGAGAGAGTTGCAGCAAGCGGTCCTTATAATCCCACGCT |
| R7 (SEQ ID NO: 10) | CGCCAGGGTTTTGGACGAACGTTTTGGTTTTTCTTTT |
| R8 (SEQ ID NO: 11) | GTTGTTCCTTTCCGAATGGTTTTTAGTTTGGAACAAG |
| R9 (SEQ ID NO: 12) | GGTTTGCCTTTAGCTGGCAACTTTCCAGCAGGCGAAA |

Strands R1-R6 were modified with 3'-cholesterol tags, and strand R7 was modified with 5'-Atto647N.

Example 2

Assembly and Membrane Insertion of Nucleic Acid Planar Ring Nanopore

The DNA ring structure was folded from ten DNA strands, i.e. one long scaffold strand S and nine short staple strands.

Firstly, the long scaffold strand S was prepared from the enzymatic ligation of two shorter strands S1 and S2 (SEQ ID NO: 1&2). In a typical reaction, 200 pmol of S1 and S2 (5'-phosphorylated) were mixed with 240 pmol of linking strand L (SEQ ID NO: 3), and annealed in a 1× T4 DNA ligase buffer from 65° C. to 25° C. in 2 hours. The T4 DNA ligase (NEB) was added, and incubated overnight at 16° C. and then heated at 65° C. for 20 min. The ligated product was purified by 2% agarose gel. The harvested strand S was then quantified by the UV absorption at 260 nm and was stored at −20° C. for the further use.

Next, to prepare DNA ring structures, with or without cholesterol-modified (Chl-DNA) and dye-labeled (Atto647N) strands, 10 pmol of scaffold strand S and 5× excess corresponding staples were mixed in the folding buffer (0.5× TAE with 12 mM MgCl2) and annealed with a 2-hour folding program (heating at 85° C. for 5 min, temperature ramping from 65° C. to 25° C. at 1° C./2.5 min, from 25° C. to 5° C. at 1° C./0.5 min) on a thermocycler. The folded structures were then characterized and purified with 1.5% agarose gel.

M-100 bp DNA ladder was used as the reference standard, lane 1—scaffold only, lane 2-linear structure (L, linearized ring), lane 3—ring structure (r0c, without cholesterol); lane 4 and 5—ring structure bearing four and six cholesterol tags (r4c and r6c), respectively; lane 6—cholesterol-DNA only. Gels were run at 65 V for 1 h at 8° C. DNA bands were visualized by staining with ethidium bromide solution and ultraviolet illumination (see FIG. 3*a*)

Figure 3:
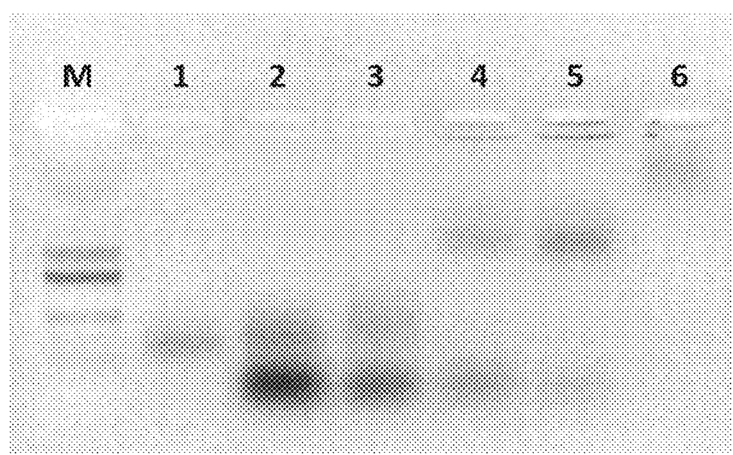
FIG. 3 (*a*) shows a photograph of an electrophoresis gel showing the results of an experiment in which: M-100 bp DNA ladder, lane 1—scaffold only, lane 2—linear structure (L, linearized ring), lane 3—ring structure (r0c, without cholesterol); lane 4 and 5—ring nanopore structure bearing four and six cholesterol tags (r4c and r6c), respectively; lane 6—cholesterol-DNA only; and (b) representative TEM images of the r0c ring (left) and a ring nanopore structure incubated with SUVs—(scale bar=20 nm).
Figure 3:
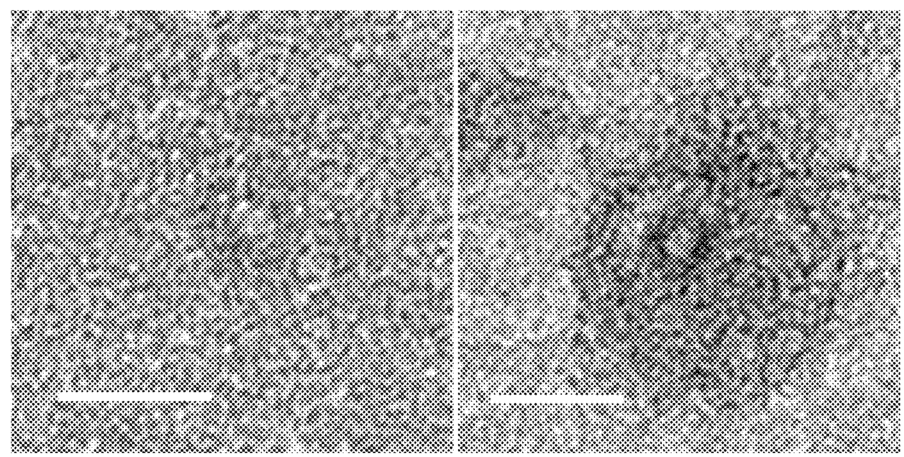

The nanostructures were further analysed by transmission electron microscopy (TEM) in order to verify their stability before and after insertion into a small unilamellar vesicle (SUV) membrane (see FIG. 3*b*).

To check the binding ability of the cholesterol-bearing DNA ring structures with the lipid membrane, two characterization methods, TEM and confocal microscope, were used.

For the TEM samples (see FIG. 3*b*), the DNA ring structures, carrying cholesterol-labeled staples, were incubated with 1-palmitoyl-2-oleoyl-sn-glycero-3-phosphocholine (POPC) SUVs 1× incubation buffer (0.5× TAE with 500 mM NaCl) for 20 min and then were used to prepare TEM grids and checked by TEM observation. The POPC SUVs solution was prepared by adding 50 μL of 20 mg/mL POPC (in chloroform) in a 2 mL glass vial and dried by argon airflow, and resuspended with 1× incubation buffer and sonicated for 30 min.

Figure 4:
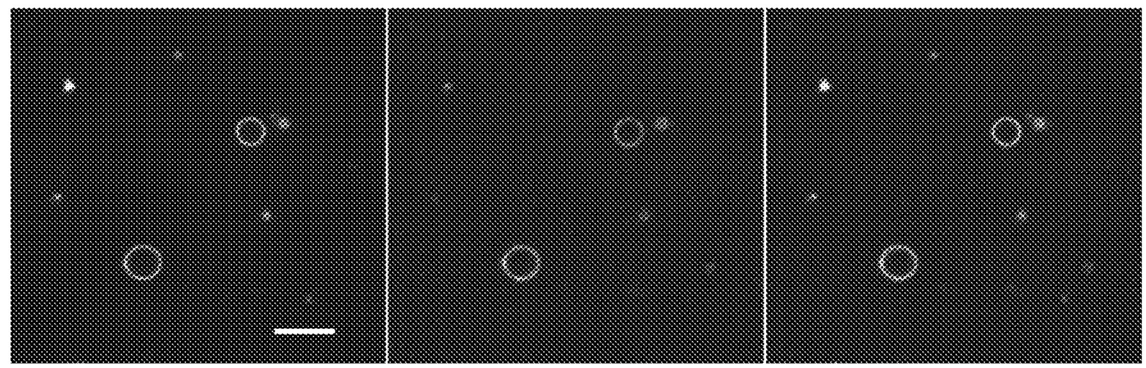
FIG. 4 shows confocal fluorescence images of GUV vesicles incubated with fluorophore-labelled DNA ring r6c. From left to right: Green channel-fluorophore-labelled lipid, Red channel-DNA ring, Merged image of the two channels. Scalebar=20 μm.

For the confocal samples (see FIG. 4), the DNA ring structures, carrying cholesterol-labeled staples and an Atto647N-labeled staple, were incubated with POPC GUVs in 1× incubation buffer for 30 min, and the incubated samples were then observed with an inverted confocal microscope (Leica). The POPC GUVs were prepared with the electroformation method. Briefly, two droplets of POPC solution (10 mg/mL in chloroform, 3 μL each) were added onto a ITO glass slide. After 5 min, the solvent was evaporated and two dried lipid film patches were formed. The glass slide was then applied on a Vesicle Prep device (Nanion). After adding 600 μL sucrose solution (1 M in water) to the lipid film patches confined by two O-rings, another ITO glass slide was applied from the top, and a sealed chamber was thus formed. An alternating electric field was applied between the two slides by running a programmed protocol, briefly, 3 V, at 5 Hz for 120 min. After the program was done, the solution was collected and then stored at 4° C. for the future use.

Example 3

Figure 5:
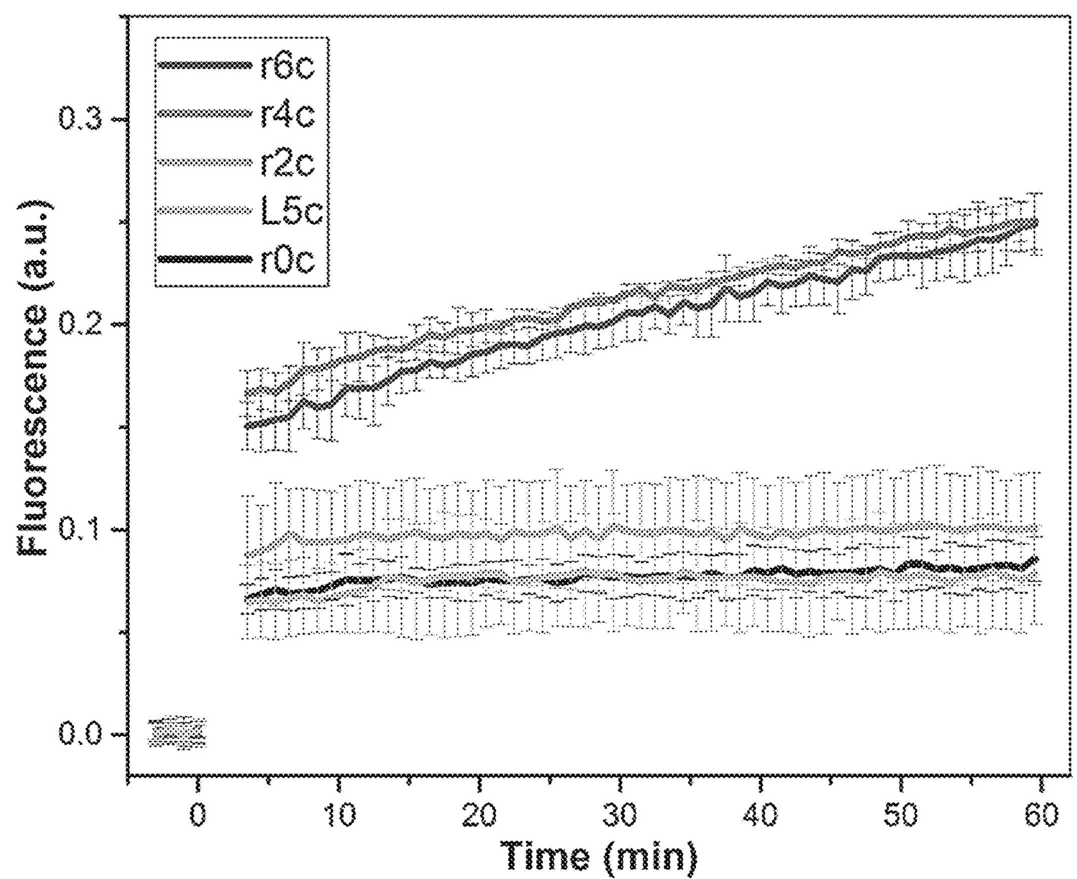
FIG. 5 shows a graph depicting time-dependent releasing of 6-Carboxyfluorescein (6-CF) from SUVs, after adding nanopore ring structures of one embodiment of the invention without or with various number of membrane anchors (cholesterol tags); r0c-ring structure without cholesterol tags; r2c, r4c and r6c-ring structures with two, four and six cholesterol tags, respectively; L5c-linear structure (control) with five cholesterol tags.) Release of 6-CF from SUVs is only observed for nanopore rings with 4 and 6 cholesterols, but not for the linearized ring with 5 cholesterol lipid anchors.

The DNA Ring Mediated Dye Releasing Tests with POPC SUVs (FIG. 5)

Firstly, the POPC SUVs was prepared with a modified method from the last section, not using the conventional 1× incubation buffer, but changing to 1× dye-containing buffer (0.5 TAE with 500 mM 6-Carboxyfluorescein (6-CF)), to resuspend the lipid film to form the dye-loaded SUVs. The excess dyes were then removed by G-25 gel filtration. The purified SUVs solution was diluted to 10 times volume in 1× incubation buffer for further use.

Next, the dye-loaded SUVs solution was used to incubate with different DNA ring structures, varying from the shapes of the structure or the number of cholesterol tags bearing on the structures. The dye-releasing tests were done on a fluorometer (Varian) by measuring the fluorescence intensity (λex=492 nm, λem=517 nm).

Example 4

Functional Nanopores Mediate the Influx of Dye into GUVs Vesicles in Size-Dependent Fashion The DNA ring structures, carrying cholesterol-labeled staples and an Atto647N-labeled staple, were added to POPC GUVs in 1× incubation buffer and mixed gently in a dish with a wait for 2 minutes for the GUVs to settle down for the confocal observation.

Figure 6:
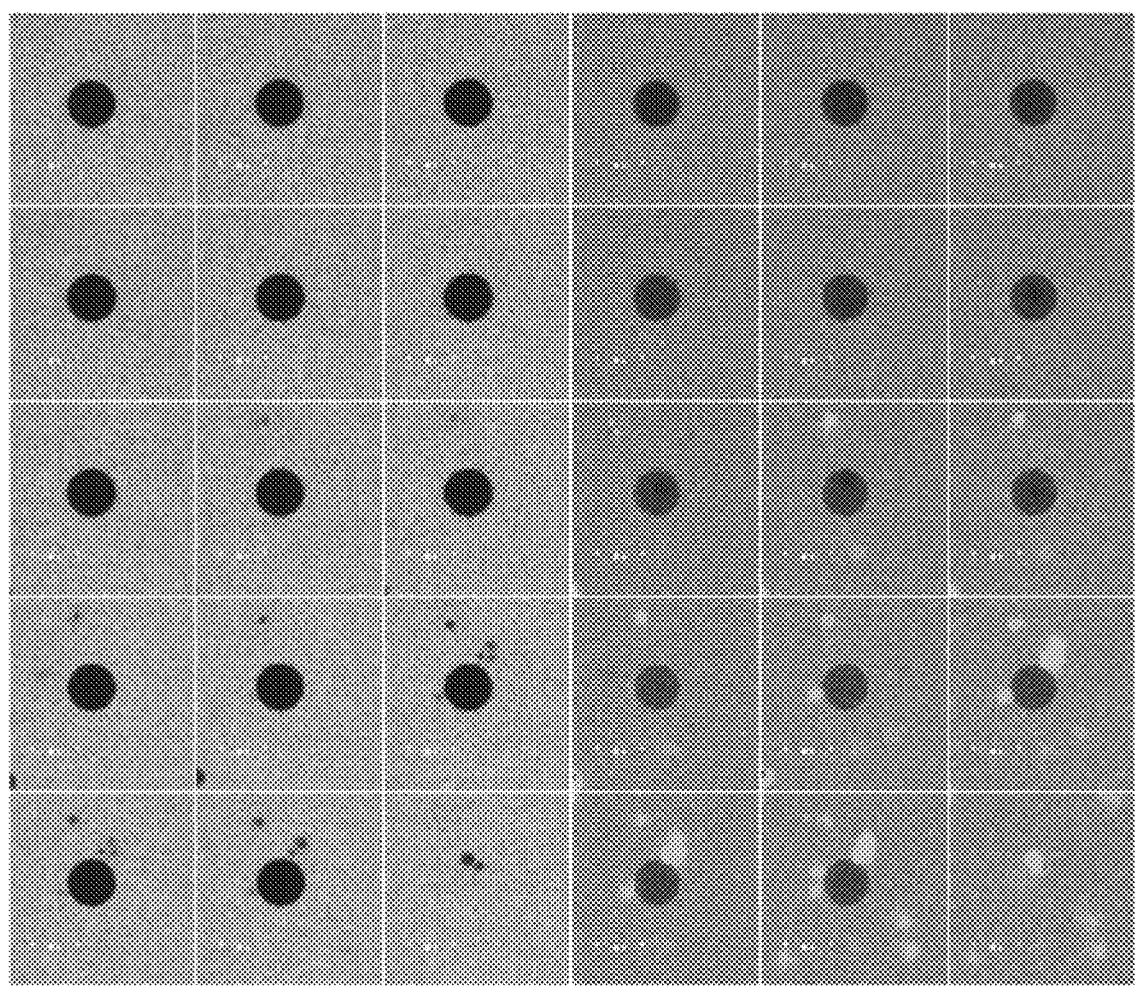
FIG. 6 shows a time-series of confocal images of dye influx mediated by nanopore rings (r6c) into GUVs. FITC-dextran (Left, hydrodynamic diameter of 15 nm) and Atto633 (Right, h.d diameter of 1 nm) were measured simultaneously.
Figure 7:
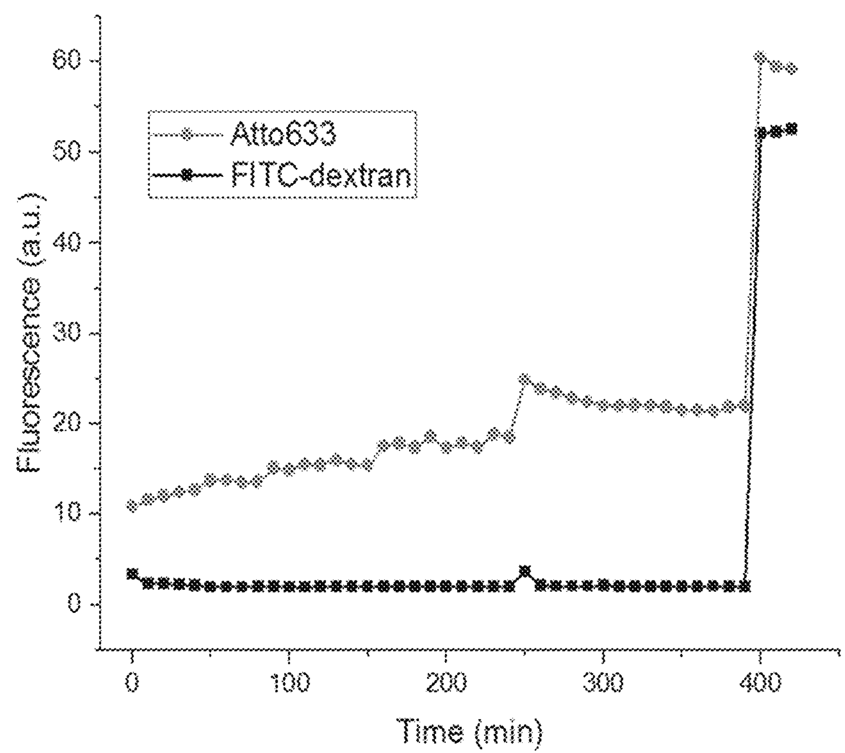
FIG. 7 shows a graph of the results shown in FIG. 6 based upon fluorescence intensity measurements of the two dyes in the GUV lumen.

To check whether the DNA ring structures can perforate the lipid membrane as transmembrane channels to transport molecular cargo, we used two kinds of dyes, FITC-dextran (green, MW=500 kD) and Atto633 (red), and checked with fluorescence intensity whether the dyes flow into the lumen of the GUVs. The dye Atto633 is a small molecule and expected to pass the ASUpore, while FITC-dextran (MW=500 kDa) with a nominal diameter of ~29.4 nm is not able to pass through the channel of DNA nanopore (nominal diameter ~10 nm). The fluorescence intensity of the two dyes was measured by examining the same microscopic region-of-interest within the GUV lumen. As shown in FIGS. 6 and 7, the intensity of the Atto633 increased with time, while the intensity of the FITC-dextran remained very low during the whole measurement over 5 hours.

Example 5

Construction of Nucleic Acid Polygonal Ring Nanopore

The design of generic polygonal pores is inspired by oligomeric protein pores and relies on a polygonal framework of multiple modular blocks. Referring to FIG. 8, the blocks or modules of the polygonal pores are suitably composed of DNA helix bundles that are arranged such a major portion of the scaffold polynucleotide chains run substantially parallel to the membrane once inserted. The polygonal nanopores of the present invention may have any suitable shape, including triangles, and quadrilaterals such as squares or rectangles, pentagons, hexagons, or trapezoid shape. The modules may have tuneable side length such as 10 or 20 nm as shown in FIG. 8. The modular blocks are composed of bundles of parallel aligned DNA duplexes. In FIG. 8A to D (triangle, square pore, pentagon and hexagon respectively), the units are made up of bundles of 3×2 duplexes having a side length of approximately 10 nm. By comparison, FIG. 8E to 8F (triangle and square respectively), the units are composed of 3×4 duplexes having a side length of approximately 20 nm. In this example, the frames enclose a channel area of about 43 to about 400 $nm^2$.

The modular blocks are connected via single stranded DNA linkers at innermost duplex layer of the blocks. To avoid instability and/or collapse of the pore and ensure the overall structure, rigid duplex stabilizers (sub-modules) are positioned between the blocks at the second duplex layer of square, pentagon and hexagon pores.

Figure 11:
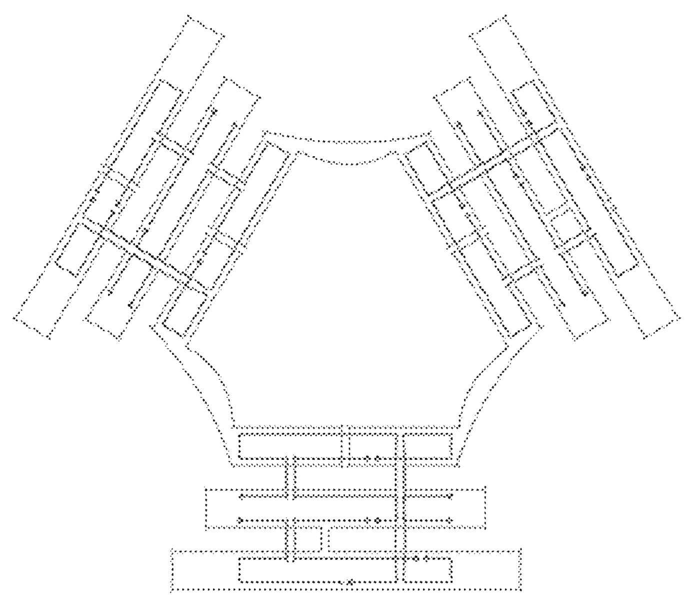
FIG. 11 shows a two-dimensional DNA map of a 10 nm frame of a triangular nanopore in accordance with an embodiment of the invention. Scaffold strands are depicted in light grey; staple strands are depicted in medium grey.
Figure 12:
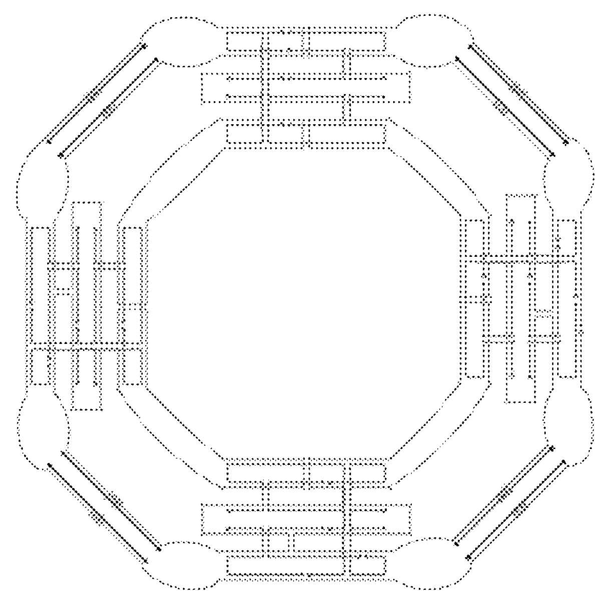
FIG. 12 shows a two-dimensional DNA map of a 10 nm frame of a square nanopore in accordance with an embodiment of the invention. Scaffold strands are depicted in light grey; staple strands are depicted in medium grey; and spacer strands are depicted in dark grey.

The two-dimensional DNA map of the 10 nm triangle and the 10 nm square pore frame are shown in FIGS. 11 and 12.

Figure 9:
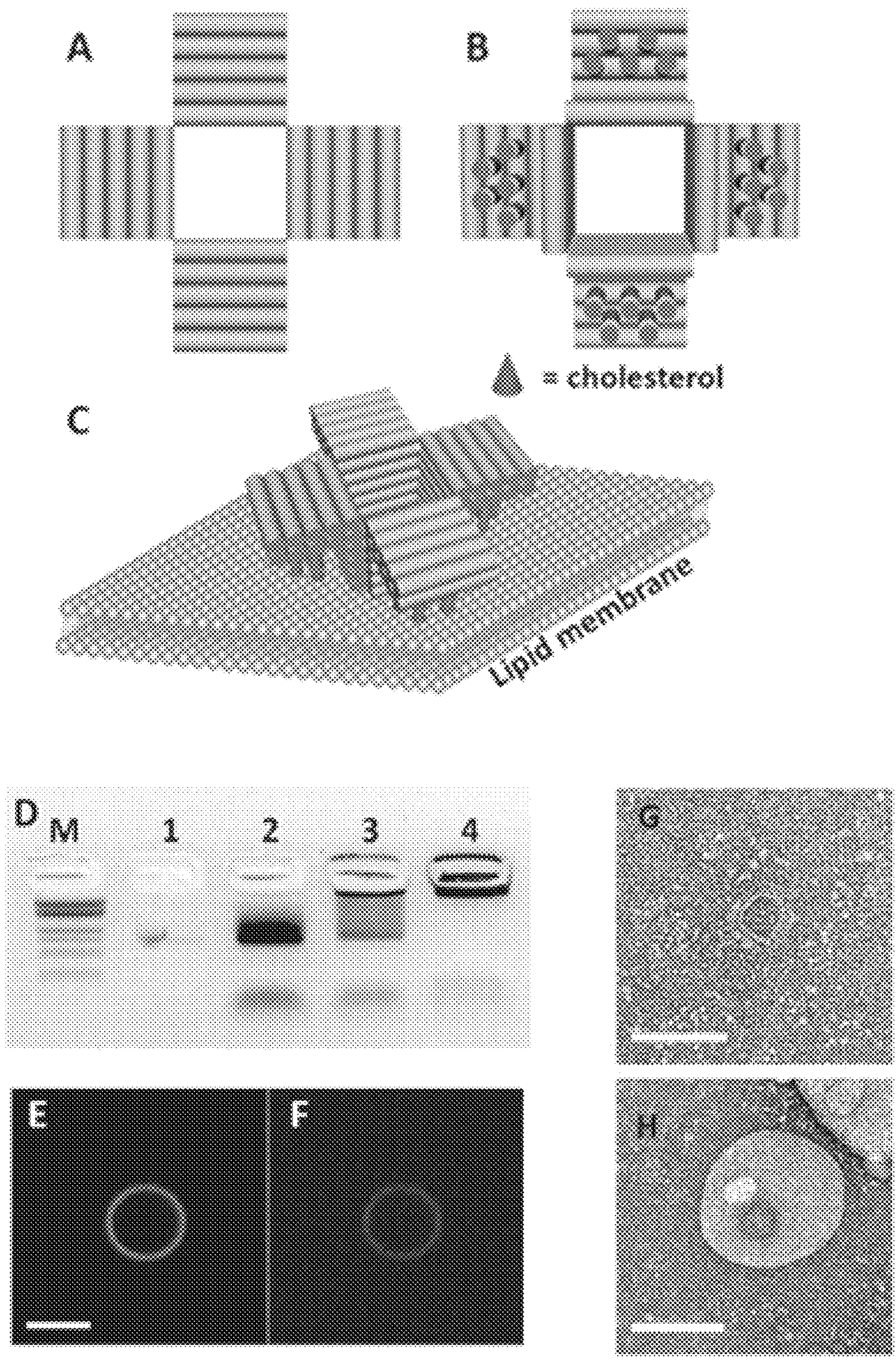
FIG. 9 shows (A) top view and (B) bottom view of the 10 nm wide DNA square-shaped pore structure binding with cholesterol strands (medium grey cone); (C) schematic representation of a membrane-bound 10 nm DNA nanopore; (D) 1.2% agarose gel analysis of the pore structure and its incubation with cholesterol strands and DPhPC SUVs: M-1 kb DNA ladder; lane 1-4: M13 scaffold, DNA pore, DNA pore bound with cholesterol strands, after incubating of the cholesterol-bound pore with DPhPC SUVs; (E)-(F) confocal images indicating the binding of DNA pore on the GUV [(E)—POPC with 0.5% Bodipy-C12-HPC; (F)—Atto647N-labelled DNA structure; scalebar=20 μm]; TEM analysis of the 20 nm wide nanopore (G) and membrane-bound nanopore (H). Scalebars in G and H are 50 nm.

As best seen in FIGS. 9B and 9C, as an additional component, the pores form a channel that punctures the membrane on insertion, as well as lipid membrane anchors.

TABLE 3

| Scaffold strands for nucleic acid polygonal nanopore: | |
|---|---|
| M13<br>(SEQ ID NO: 13) | AATGCTACTACTATTAGTAGAATTGATGCCACCTTTTCAGCTCGCGCCCCAAATGAAAA<br>TATAGCTAAACAGGTTATTGACCATTTGCGAAATGTATCTAATGGTCAAACTAAATCTAC<br>TCGTTCGCAGAATTGGGAATCAACTGTTATATGGAATGAAACTTCCAGACACCGTACTT<br>TAGTTGCATATTTAAAACATGTTGAGCTACAGCATTATATTCAGCAATTAAGCTCTAAGC<br>CATCCGCAAAAATGACCTCTTATCAAAAGGAGCAATTAAAGGTACTCTCTAATCCTGAC |

TABLE 3-continued

| Scaffold strands for nucleic acid polygonal nanopore: |
| --- |
| CTGTTGGAGTTTGCTTCCGGTCTGGTTCGCTTTGAAGCTCGAATTAAAACGCGATATTT |
| GAAGTCTTTCGGGCTTCCTCTTAATCTTTTTGATGCAATCCGCTTTGCTTCTGACTATAA |
| TAGTCAGGGTAAAGACCTGATTTTTGATTTATGGTCATTCTCGTTTTCTGAACTGTTTAA |
| AGCATTTGAGGGGGATTCAATGAATATTTATGACGATTCCGCAGTATTGGACGCTATCC |
| AGTCTAAACATTTTACTATTACCCCCTCTGGCAAAACTTCTTTTGCAAAAGCCTCTCGCT |
| ATTTTGGTTTTTATCGTCGTCTGGTAAACGAGGGTTATGATAGTGTTGCTCTTACTATGC |
| CTCGTAATTCCTTTTGGCGTTATGTATCTGCATTAGTTGAATGTGGTATTCCTAAATCTC |
| AACTGATGAATCTTTCTACCTGTAATAATGTTGTTCCGTTAGTTCGTTTTATTAACGTAGA |
| TTTTTCTTCCCAACGTCCTGACTGGTATAATGAGCCAGTTCTTAAAATCGCATAAGGTAA |
| TTCACAATGATTAAAGTTGAAATTAAACCATCTCAAGCCCAATTTACTACTCGTTCTGGT |
| GTTTCTCGTCAGGGCAAGCCTTATTCACTGAATGAGCAGCTTTGTTACGTTGATTTGGG |
| TAATGAATATCCGGTTCTTGTCAAGATTACTCTTGATGAAGGTCAGCCAGCCTATGCGC |
| CTGGTCTGTACACCGTTCATCTGTCCTCTTTCAAAGTTGGTCAGTTCGGTTCCCTTATG |
| ATTGACCGTCTGCGCCTCGTTCCGGCTAAGTAACATGGAGCAGGTCGCGGATTTCGAC |
| ACAATTTATCAGGCGATGATACAAATCTCCGTTGTACTTTGTTTCGCGCTTGGTATAATC |
| GCTGGGGGTCAAAGATGAGTGTTTTAGTGTATTCTTTTGCCTCTTTCGTTTTAGGTTGG |
| TGCCTTCGTAGTGGCATTACGTATTTTACCCGTTTAATGGAAACTTCCTCATGAAAAAGT |
| CTTTAGTCCTCAAAGCCTCTGTAGCCGTTGCTACCCTCGTTCCGATGCTGTCTTTCGCT |
| GCTGAGGGTGACGATCCCGCAAAAGCGGCCTTTAACTCCCTGCAAGCCTCAGCGACC |
| GAATATATCGGTTATGCGTGGGCGATGGTTGTTGTCATTGTCGGCGCAACTATCGGTAT |
| CAAGCTGTTTAAGAAATTCACCTCGAAAGCAAGCTGATAAACCGATACAATTAAAGGCT |
| CCTTTTGGAGCCTTTTTTTTGGAGATTTTCAACGTGAAAAAATTATTATTCGCAATTCCTT |
| TAGTTGTTCCTTTCTATTCTCACTCCGCTGAAACTGTTGAAAGTTGTTTAGCAAAATCCC |
| ATACAGAAAATTCATTTACTAACGTCTGGAAAGACGACAAAACTTTAGATCGTTACGCTA |
| ACTATGAGGGCTGTCTGTGGAATGCTACAGGCGTTGTAGTTTGTACTGGTGACGAAAC |
| TCAGTGTTACGGTACATGGGTTCCTATTGGGCTTGCTATCCCTGAAAATGAGGGTGGT |
| GGCTCTGAGGGTGGCGGTTCTGAGGGTGGCGGTTCTGAGGGTGGCGGTACTAAACCT |
| CCTGAGTACGGTGATACACCTATTCCGGGCTATACTTATATCAACCCTCTCGACGGCAC |
| TTATCCGCCTGGTACTGAGCAAAACCCCGCTAATCCTAATCCTTCTCTTGAGGAGTCTC |
| AGCCTCTTAATACTTTCATGTTTCAGAATAATAGGTTCCGAAATAGGCAGGGGGCATTA |
| ACTGTTTATACGGGCACTGTTACTCAAGGCACTGACCCCGTTAAAACTTATTACCAGTA |
| CACTCCTGTATCATCAAAAGCCATGTATGACGCTTACTGGAACGGTAAATTCAGAGACT |
| GCGCTTTCCATTCTGGCTTTAATGAGGATTTATTTGTTTGTGAATATCAAGGCCAATCGT |
| CTGACCTGCCTCAACCTCCTGTCAATGCTGGCGGCGGCTCTGGTGGTGGTTCTGGTG |
| GCGGCTCTGAGGGTGGTGGCTCTGAGGGTGGCGGTTCTGAGGGTGGCGGCTCTGAG |
| GGAGGCGGTTCCGGTGGTGGCTCTGGTTCCGGTGATTTTGATTATGAAAAGATGGCAA |
| ACGCTAATAAGGGGGCTATGACCGAAAATGCCGATGAAAACGCGCTACAGTCTGACGC |
| TAAAGGCAAACTTGATTCTGTCGCTACTGATTACGGTGCTGCTATCGATGGTTTCATTG |
| GTGACGTTTCCGGCCTTGCTAATGGTAATGGTGCTACTGGTGATTTTGCTGGCTCTAAT |
| TCCCAAATGGCTCAAGTCGGTGACGGTGATAATTCACCTTTAATGAATAATTTCCGTCA |
| ATATTTACCTTCCCTCCCTCAATCGGTTGAATGTCGCCCTTTTGTCTTTGGCGCTGGTA |
| AACCATATGAATTTTCTATTGATTGTGACAAAATAAACTTATTCCGTGGTGTCTTTGCGT |
| TTCTTTTATATGTTGCCACCTTTATGTATGTATTTTCTACGTTTGCTAACATACTGCGTAA |
| TAAGGAGTCTTAATCATGCCAGTTCTTTTGGGTATTCCGTTATTATTGCGTTTCCTCGGT |
| TTCCTTCTGGTAACTTTGTTCGGCTATCTGCTTACTTTTCTTAAAAAGGGCTTCGGTAAG |
| ATAGCTATTGCTATTTCATTGTTTCTTGCTCTTATTATTGGGCTTAACTCAATTCTTGTGG |
| GTTATCTCTCTGATATTAGCGCTCAATTACCCTCTGACTTTGTTCAGGGTGTTCAGTTAA |
| TTCTCCCGTCTAATGCGCTTCCCTGTTTTTATGTTATTCTCTCTGTAAAGGCTGCTATTT |
| TCATTTTTGACGTTAAACAAAAAATCGTTTCTTATTTGGATTGGGATAAATAATATGGCT |
| GTTTATTTTGTAACTGGCAAATTAGGCTCTGGAAAGACGCTCGTTAGCGTTGGTAAGAT |
| TCAGGATAAAATTGTAGCTGGGTGCAAAATAGCAACTAATCTTGATTTAAGGCTTCAAAA |
| CCTCCCGCAAGTCGGGAGGTTCGCTAAAACGCCTCGCGTTCTTAGAATACCGGATAAG |
| CCTTCTATATCTGATTTGCTTGCTATTGGGCGCGGTAATGATTCCTACGATGAAAATAAA |
| AACGGCTTGCTTGTTCTCGATGAGTGCGGTACTTGGTTTAATACCCGTTCTTGGAATGA |
| TAAGGAAAGACAGCCGATTATTGATTGGTTTCTACATGCTCGTAAATTAGGATGGGATA |
| TTATTTTTCTTGTTCAGGACTTATCTATTGTTGATAAACAGGCGCGTTCTGCATTAGCTG |
| AACATGTTGTTTATTGTCGTCGTCTGGACAGAATTACTTTACCTTTTGTCGGTACTTTAT |
| ATTCTCTTATTACTGGCTCGAAAATGCCTCTGCCTAAATTACATGTTGGCGTTGTTAAAT |
| ATGGCGATTCTCAATTAAGCCCTACTGTTGAGCGTTGGCTTTATACTGGTAAGAATTTG |
| TATAACGCATATGATACTAAACAGGCTTTTTCTAGTAATTATGATTCCGGTGTTTATTCTT |
| ATTTAACGCCTTATTTATCACACGGTCGGTATTTCAAACCATTAAATTTAGGTCAGAAGA |
| TGAAATTAACTAAAATATATTTGAAAAAGTTTTCTCGCGTTCTTTGTCTTGCGATTGGATT |
| TGCATCAGCATTTACATATAGTTATATAACCCAACCTAAGCCGGAGGTTAAAAAGGTAG |
| TCTCTCAGACCTATGATTTTGATAAATTCACTATTGACTCTTCTCAGCGTCTTAATCTAA |
| GCTATCGCTATGTTTTCAAGGATTCTAAGGGAAAATTAATTAATAGCGACGATTTACAGA |
| AGCAAGGTTATTCACTCACATATATTGATTTATGTACTGTTTCCATTAAAAAAGGTAATTC |
| AAATGAAATTGTTAAATGTAATTAATTTTGTTTTCTTGATGTTTGTTTCATCATCTTCTTTT |
| GCTCAGGTAATTGAAATGAATAATTCGCCTCTGCGCGATTTTGTAACTTGGTATTCAAA |
| GCAATCAGGCGAATCCGTTATTGTTTCTCCCGATGTAAAAGGTACTGTTACTGTATATTC |
| ATCTGACGTTAAACCTGAAAATCTACGCAATTTCTTTATTTCTGTTTTACGTGCAAATAAT |
| TTTGATATGGTAGGTTCTAACCCTTCCATTATTCAGAAGTATAATCCAAACAATCAGGAT |
| TATATTGATGAATTGCCATCATCTGATAATCAGGAATATGATGATAATTCCGCTCCTTCT |
| GGTGGTTTCTTTGTTCCGCAAAATGATAATGTTACTCAAACTTTTAAAATTAATAACGTTC |
| GGGCAAAGGATTTAATACGAGTTGTCGAATTGTTTGTAAAGTCTAATACTTCTAAATCCT |
| CAAATGTATTATCTATTGACGGCTCTAATCTATTAGTTGTTAGTGCTCCTAAAGATATTTT |
| AGATAACCTTCCTCAATTCCTTTCAACTGTTGATTTGCCAACTGACCAGATATTGATTGA |
| GGGTTTGATATTTGAGGTTCAGCAAGGTGATGCTTTAGATTTTTCATTTGCTGCTGGCT |
| CTCAGCGTGGCACTGTTGCAGGCGGTGTTAATACTGACCGCCTCACCTCTGTTTTATCT |

TABLE 3-continued

Scaffold strands for nucleic acid polygonal nanopore:

TCTGCTGGTGGTTCGTTCGGTATTTTTAATGGCGATGTTTTAGGGCTATCAGTTCGCGC
ATTAAAGACTAATAGCCATTCAAAAATATTGTCTGTGCCACGTATTCTTACGCTTTCAGG
TCAGAAGGGTTCTATCTCTGTTGGCCAGAATGTCCCTTTTATTACTGGTCGTGTGACTG
GTGAATCTGCCAATGTAAATAATCCATTTCAGACGATTGAGCGTCAAAATGTAGGTATTT
CCATGAGCGTTTTTCCTGTTGCAATGGCTGGCGGTAATATTGTTCTGGATATTACCAGC
AAGGCCGATAGTTTGAGTTCTTCTACTCAGGCAAGTGATGTTATTACTAATCAAAGAAG
TATTGCTACAACGGTTAATTTGCGTGATGGACAGACTCTTTTACTCGGTGGCCTCACTG
ATTATAAAAACACTTCTCAGGATTCTGGCGTACCGTTCCTGTCTAAAATCCCTTTAATCG
GCCTCCTGTTTAGCTCCCGCTCTGATTCTAACGAGGAAAGCACGTTATACGTGCTCGTC
AAAGCAACCATAGTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCTTTC
TTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTTG
GGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCT
ATCTCGGGCTATTCTTTTGATTTATAAGGGATTTTGCCGATTTCGGAACCACCATCAAAC
AGGATTTTCGCCTGCTGGGGCAAACCAGCGTGGACCGCTTGCTGCAACTCTCTCAGG
GCCAGGCGGTGAAGGGCAATCAGCTGTTGCCCGTCTCACTGGTGAAAAGAAAAACCA
CCCTGGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATG
TGAGTTAGCTCACTCATTAGGCACCCCAGGCTTTACACTTTATGCTTCCGGCTCGTATG
TTGTGTGGAATTGTGAGCGGATAACAATTTCACACAGGAAACAGCTATGACCATGATTA
CGAATTCGAGCTCGGTACCCGGGGATCCTCTAGAGTCGACCTGCAGGCATGCAAGCTT
GGCACTGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGGCCCGCA
CCGATCGCCCTTCCCAACAGTTGCGCAGCCTGAATGGCGAATGGCGCTTTGCCTGGTT
TCCGGCACCAGAAGCGGTGCCGGAAAGCTGGCTGGAGTGCGATCTTCCTGAGGCCGA
TACTGTCGTCGTCCCCTCAAACTGGCAGATGCACGGTTACGATGCGCCCATCTACACC
AACGTGACCTATCCCATTACGGTCAATCCGCCGTTTGTTCCCACGGAGAATCCGACGG
GTTGTTACTCGCTCACATTTAATGTTGATGAAAGCTGGCTACAGGAAGGCCAGACGCG
AATTATTTTTGATGGCGTTCCTATTGGTTAAAAAATGAGCTGATTTAACAAAAATTTAATG
CGAATTTTAACAAAATATTAACGTTTACAATTTAAATATTTGCTTATACAATCTTCCTGTTT
TTGGGGCTTTTCTGATTATCAACCGGGGTACATATGATTGACATGCTAGTTTTACGATTA
CCGTTCATCGATTCTCTTGTTTGCTCCAGACTCTCAGGCAATGACCTGATAGCCTTTGT
AGATCTCTCAAAAATAGCTACCCTCTCCGGCATTAATTTATCAGCTAGAACGGTTGAATA
TCATATTGATGGTGATTTGACTGTCTCCGGCCTTTCTCACCCTTTTGAATCTTTACCTAC
ACATTACTCAGGCATTGCATTTAAAATATATGAGGGTTCTAAAAATTTTTATCCTTGCGTT
GAAATAAAGGCTTCTCCCGCAAAAGTATTACAGGGTCATAATGTTTTTGGTACAACCGA
TTTAGCTTTATGCTCTGAGGCTTTATTGCTTAATTTTGCTAATTCTTTGCCTTGCCTGTAT
GATTTATTGGATGTT

PhiX174 (SEQ ID NO: 14)

GAGTTTTATCGCTTCCATGACGCAGAAGTTAACACTTTCGGATATTTCTGATGAGTCGA
AAAATTATCTTGATAAAGCAGGAATTACTACTGCTTGTTTACGAATTAAATCGAAGTGGA
CTGCTGGCGGAAAATGAGAAAATTCGACCTATCCTTGCGCAGCTCGAGAAGCTCTTAC
TTTGCGACCTTTCGCCATCAACTAACGATTCTGTCAAAAACTGACGCGTTGGATGAGGA
GAAGTGGCTTAATATGCTTGGCACGTTCGTCAAGGACTGGTTTAGATATGAGTCACATT
TTGTTCATGGTAGAGATTCTCTTGTTGACATTTTAAAAGAGCGTGGATTACTATCTGAGT
CCGATGCTGTTCAACCACTAATAGGTAAGAAATCATGAGTCAAGTTACTGAACAATCCG
TACGTTTCCAGACCGCTTTGGCCTCTATTAAGCTCATTCAGGCTTCTGCCGTTTTGGAT
TTAACCGAAGATGATTTCGATTTTCTGACGAGTAACAAAGTTTGGATTGCTACTGACCG
CTCTCGTGCTCGTCGCTGCGTTGAGGCTTGCGTTTATGGTACGCTGGACTTTGTAGGA
TACCCTCGCTTTCCTGCTCCTGTTGAGTTTATTGCTGCCGTCATTGCTTATTATGTTCAT
CCCGTCAACATTCAAACGGCCTGTCTCATCATGGAAGGCGCTGAATTTACGGAAAACAT
TATTAATGGCGTCGAGCGTCCGGTTAAAGCCGCTGAATTGTTCGCGTTTACCTTGCGT
GTACGCGCAGGAAACACTGACGTTCTTACTGACGCAGAAGAAAACGTGCGTCAAAAAT
TACGTGCAGAAGGAGTGATGTAATGTCTAAAGGTAAAAAACGTTCTGGCGCTCGCCCT
GGTCGTCCGCAGCCGTTGCGAGGTACTAAAGGCAAGCGTAAAGGCGCTCGTCTTTGG
TATGTAGGTGGTCAACAATTTTAATTGCAGGGGCTTCGGCCCCTTACTTGAGGATAAAT
TATGTCTAATATTCAAACTGGCGCCGAGCGTATGCCGCATGACCTTTCCCATCTTGGCT
TCCTTGCTGGTCAGATTGGTCGTCTTATTACCATTTCAACTACTCCGGTTATCGCTGGC
GACTCCTTCGAGATGGACGCCGTTGGCGCTCTCCGTCTTTCTCCATTGCGTCGTGGCC
TTGCTATTGACTCTACTGTAGACATTTTTACTTTTTATGTCCCTCATCGTCACGTTTATGG
TGAACAGTGGATTAAGTTCATGAAGGATGGTGTTAATGCCACTCCTCTCCCGACTGTTA
ACACTACTGGTTATATTGACCATGCCGCTTTTCTTGGCACGATTAACCCTGATACCAATA
AAATCCCTAAGCATTTGTTTCAGGGTTATTTGAATATCTATAACAACTATTTTAAAGCGC
CGTGGATGCCTGACCGTACCGAGGCTAACCCTAATGAGCTTAATCAAGATGATGCTCG
TTATGGTTTCCGTTGCTGCCATCTCAAAAACATTTGGACTGCTCCGCTTCCTCCTGAGA
CTGAGCTTTCTCGCCAAATGACGACTTCTACCACATCTATTGACATTATGGGTCTGCAA
GCTGCTTATGCTAATTTGCATACTGACCAAGAACGTGATTACTTCATGCAGCGTTACCA
TGATGTTATTTCTTCATTTGGAGGTAAAACCTCTTATGACGCTGACAACCGTCCTTTACT
TGTCATGCGCTCTAATCTCTGGGCATCTGGCTATGATGTTGATGGAACTGACCAAACGT
CGTTAGGCCAGTTTTCTGGTCGTGTTCAACAGACCTATAAACATTCTGTGCCGCGTTTC
TTTGTTCCTGAGCATGGCACTATGTTTACTCTTGCGCTTGTTCGTTTTCCGCCTACTGC
GACTAAAGAGATTCAGTACCTTAACGCTAAAGGTGCTTTGACTTATACCGATATTGCTG
GCGACCCTGTTTTGTATGGCAACTTGCCGCCGCGTGAAATTTCTATGAAGGATGTTTTC
CGTTCTGGTGATTCGTCTAAGAAGTTTAAGATTGCTGAGGGTCAGTGGTATCGTTATGC
GCCTTCGTATGTTTCTCCTGCTTATCACCTTCTTGAAGGCTTCCCATTCATTCAGGAACC
GCCTTCTGGTGATTTGCAAGAACGCGTACTTATTCGCCACCATGATTATGACCAGTGTT

TABLE 3-continued

| Scaffold strands for nucleic acid polygonal nanopore: |
|---|
| TCCAGTCCGTTCAGTTGTTGCAGTGGAATAGTCAGGTTAAATTTAATGTGACCGTTTAT |
| CGCAATCTGCCGACCACTCGCGATTCAATCATGACTTCGTGATAAAAGATTGAGTGTGA |
| GGTTATAACGCCGAAGCGGTAAAAATTTTAATTTTTGCCGCTGAGGGGTTGACCAAGC |
| GAAGCGCGGTAGGTTTTCTGCTTAGGAGTTTAATCATGTTTCAGACTTTTATTTCTCGCC |
| ATAATTCAAACTTTTTTTCTGATAAGCTGGTTCTCACTTCTGTTACTCCAGCTTCTTCGG |
| CACCTGTTTTACAGACACCTAAAGCTACATCGTCAACGTTATATTTTGATAGTTTGACGG |
| TTAATGCTGGTAATGGTGGTTTTCTTCATTGCATTCAGATGGATACATCTGTCAACGCC |
| GCTAATCAGGTTGTTTCTGTTGGTGCTGATATTGCTTTTGATGCCGACCCTAAATTTTTT |
| GCCTGTTTGGTTCGCTTTGAGTCTTCTTCGGTTCCGACTACCCTCCCGACTGCCTATGA |
| TGTTTATCCTTTGGATGGTCGCCATGATGGTGGTTATTATACCGTCAAGGACTGTGTGA |
| CTATTGACGTCCTTCCCCGTACGCCGGGCAATAATGTTTATGTTGGTTTCATGGTTTGG |
| TCTAACTTTACCGCTACTAAATGCCGCGGATTGGTTTCGCTGAATCAGGTTATTAAAGA |
| GATTATTTGTCTCCAGCCACTTAAGTGAGGTGATTTATGTTTGGTGCTATTGCTGGCGG |
| TATTGCTTCTGCTCTTGCTGGTGGCGCCATGTCTAAATTGTTTGGAGGCGGTCAAAAAG |
| CCGCCTCCGGTGGCATTCAAGGTGATGTGCTTGCTACCGATAACAATACTGTAGGCAT |
| GGGTGAGAGTTTTATCGCTTCCATGACGCAGAAGTTAACACTTTCGGATATTTCTGATG |
| AGTCGAAAAATTATCTTGATAAAGCAGGAATTACTACTGCTTGTTTACGAATTAAATCGA |
| AGTGGACTGCTGGCGGAAAATGAGAAAATTCGACCTATCCTTGCGCAGCTCGAGAAGC |
| TCTTACTTTGCGACCTTTCGCCATCAACTAACGATTCTGTCAAAAACTGACGCGTTGGA |
| TGAGGAGAAGTGGCTTAATATGCTTGGCACGTTCGTCAAGGACTGGTTTAGATATGAGT |
| CACATTTTGTTCATGGTAGAGATTCTCTTGTTGACATTTTAAAAGAGCGTGGATTACTAT |
| CTGAGTCCGATGCTGTTCAACCACTAATAGGTAAGAAATCATGAGTCAAGTTACTGAAC |
| AATCCGTACGTTTCCAGACCGCTTTGGCCTCTATTAAGCTCATTCAGGCTTCTGCCGTT |
| TTGGATTTAACCGAAGATGATTTCGATTTTCTGACGAGTAACAAAGTTTGGATTGCTACT |
| GACCGCTCTCGTGCTCGTCGCTGCGTTGAGGCTTGCGTTTATGGTACGCTGGACTTTG |
| TAGGATACCCTCGCTTTCCTGCTCCTGTTGAGTTTATTGCTGCCGTCATTGCTTATTATG |
| TTCATCCCGTCAACATTCAAACGGCCTGTCTCATCATGGAAGGCGCTGAATTTACGGAA |
| AACATTATTAATGGCGTCGAGCGTCCGGTTAAAGCCGCTGAATTGTTCGCGTTTACCTT |
| GCGTGTACGCGCAGGAAACACTGACGTTCTTACTGACGCAGAAGAAAACGTGCGTCAA |
| AAATTACGTGCAGAAGGAGTGATGTAATGTCTAAAGGTAAAAAACGTTCTGGCGCTCGC |
| CCTGGTCGTCCGCAGCCGTTGCGAGGTACTAAAGGCAAGCGTAAAGGCGCTCGTCTTT |
| GGTATGTAGGTGGTCAACAATTTTAATTGCAGGGGCTTCGGCCCCTTACTTGAGGATAA |
| ATTATGTCTAATATTCAAACTGGCGCCGAGCGTATGCCGCATGACCTTTCCCATCTTGG |
| CTTCCTTGCTGGTCAGATTGGTCGTCTTATTACCATTTCAACTACTCCGGTTATCGCTG |
| GCGACTCCTTCGAGATGGACGCCGTTGGCGCTCTCCGTCTTTCTCCATTGCGTCGTGG |
| CCTTGCTATTGACTCTACTGTAGACATTTTTACTTTTTATGTCCCTCATCGTCACGTTTAT |
| GGTGAACAGTGGATTAAGTTCATGAAGGATGGTGTTAATGCCACTCCTCTCCCGACTGT |
| TAACACTACTGGTTATATTGACCATGCCGCTTTTCTTGGCACGATTAACCCTGATACCAA |
| TAAAATCCCTAAGCATTTGTTTCAGGGTTATTTGAATATCTATAACAACTATTTTAAAGCG |
| CCGTGGATGCCTGACCGTACCGAGGCTAACCCTAATGAGCTTAATCAAGATGATGCTC |
| GTTATGGTTTCCGTTGCTGCCATCTCAAAAACATTTGGACTGCTCCGCTTCCTCCTGAG |
| ACTGAGCTTTCTCGCCAAATGACGACTTCTACCACATCTATTGACATTATGGGTCTGCA |
| AGCTGCTTATGCTAATTTGCATACTGACCAAGAACGTGATTACTTCATGCAGCGTTACC |
| ATGATGTTATTTCTTCATTTGGAGGTAAAACCTCTTATGACGCTGACAACCGTCCTTTAC |
| TTGTCATGCGCTCTAATCTCTGGGCATCTGGCTATGATGTTGATGGAACTGACCAAACG |
| TCGTTAGGCCAGTTTTCTGGTCGTGTTCAACAGACCTATAAACATTCTGTGCCGCGTTT |
| CTTTGTTCCTGAGCATGGCACTATGTTTACTCTTGCGCTTGTTCGTTTTCCGCCTACTG |
| CGACTAAAGAGATTCAGTACCTTAACGCTAAAGGTGCTTTGACTTATACCGATATTGCT |
| GGCGACCCTGTTTTGTATGGCAACTTGCCGCCGCGTGAAATTTCTATGAAGGATGTTTT |
| CCGTTCTGGTGATTCGTCTAAGAAGTTTAAGATTGCTGAGGGTCAGTGGTATCGTTATG |
| CGCCTTCGTATGTTTCTCCTGCTTATCACCTTCTTGAAGGCTTCCCATTCATTCAGGAAC |
| CGCCTTCTGGTGATTTGCAAGAACGCGTACTTATTCGCCACCATGATTATGACCAGTGT |
| TTCCAGTCCGTTCAGTTGTTGCAGTGGAATAGTCAGGTTAAATTTAATGTGACCGTTTAT |
| CGCAATCTGCCGACCACTCGCGATTCAATCATGACTTCGTGATAAAAGATTGAGTGTGA |
| GGTTATAACGCCGAAGCGGTAAAAATTTTAATTTTTGCCGCTGAGGGGTTGACCAAGC |
| GAAGCGCGGTAGGTTTTCTGCTTAGGAGTTTAATCATGTTTCAGACTTTTATTTCTCGCC |
| ATAATTCAAACTTTTTTTCTGATAAGCTGGTTCTCACTTCTGTTACTCCAGCTTCTTCGG |
| CACCTGTTTTACAGACACCTAAAGCTACATCGTCAACGTTATATTTTGATAGTTTGACGG |
| TTAATGCTGGTAATGGTGGTTTTCTTCATTGCATTCAGATGGATACATCTGTCAACGCC |
| GCTAATCAGGTTGTTTCTGTTGGTGCTGATATTGCTTTTGATGCCGACCCTAAATTTTTT |
| GCCTGTTTGGTTCGCTTTGAGTCTTCTTCGGTTCCGACTACCCTCCCGACTGCCTATGA |
| TGTTTATCCTTTGGATGGTCGCCATGATGGTGGTTATTATACCGTCAAGGACTGTGTGA |
| CTATTGACGTCCTTCCCCGTACGCCGGGCAATAATGTTTATGTTGGTTTCATGGTTTGG |
| TCTAACTTTACCGCTACTAAATGCCGCGGATTGGTTTCGCTGAATCAGGTTATTAAAGA |
| GATTATTTGTCTCCAGCCACTTAAGTGAGGTGATTTATGTTTGGTGCTATTGCTGGCGG |
| TATTGCTTCTGCTCTTGCTGGTGGCGCCATGTCTAAATTGTTTGGAGGCGGTCAAAAAG |
| CCGCCTCCGGTGGCATTCAAGGTGATGTGCTTGCTACCGATAACAATACTGTAGGCAT |
| GGGTGATGCTGGTATTAAATCTGCCATTCAAGGCTCTAATGTTCCTAACCCTGATGAGG |
| CCGTCCCTAGTTTTGTTTCTGGTGCTATGGCTAAAGCTGGTAAAGGACTTCTTGAAGGT |
| ACGTTGCAGGCTGGCACTTCTGCCGTTTCTGATAAGTTGCTTGATTTGGTTGGACTTGG |
| TGGCAAGTCTGCCGCTGATAAAGGAAAGGATACTCGTGATTATCTTGCTGCTGCATTTC |
| CTGAGCTTAATGCTTGGGAGCGTGCTGGTGCTGATGCTTCCTCTGCTGGTATGGTTGA |
| CGCCGGATTTGAGAATCAAAAAGAGCTTACTAAAATGCAACTGGACAATCAGAAAGAGA |
| TTGCCGAGATGCAAAATGAGACTCAAAAAGAGATTGCTGGCATTCAGTCGGCGACTTC |
| ACGCCAGAATACGAAAGACCAGGTATATGCACAAAATGAGATGCTTGCTTATCAACAGA |
| AGGAGTCTACTGCTCGCGTTGCGTCTATTATGGAAAACACCAATCTTTCCAAGCAACAG |
| CAGGTTTCCGAGATTATGCGCCAAATGCTTACTCAAGCTCAAACGGCTGGTCAGTATTT |
| TACCAATGACCAAATCAAAGAAATGACTCGCAAGGTTAGTGCTGAGGTTGACTTAGTTC |

TABLE 3-continued

| Scaffold strands for nucleic acid polygonal nanopore: |
|---|
| ATCAGCAAACGCAGAATCAGCGGTATGGCTCTTCTCATATTGGCGCTACTGCAAAGGA<br>TATTTCTAATGTCGTCACTGATGCTGCTTCTGGTGTGGTTGATATTTTTCATGGTATTGA<br>TAAAGCTGTTGCCGATACTTGGAACAATTTCTGGAAAGACGGTAAAGCTGATGGTATTG<br>GCTCTAATTTGTCTAGGAAATAACCGTCAGGATTGACACCCTCCCAATTGTATGTTTTCA<br>TGCCTCCAAATCTTGGAGGCTTTTTTATGGTTCGTTCTTATTACCCTTCTGAATGTCACG<br>CTGATTATTTTGACTTTGAGCGTATCGAGGCTCTTAAACCTGCTATTGAGGCTTGTGGC<br>ATTTCTACTCTTTCTCAATCCCCAATGCTTGGCTTCCATAAGCAGATGGATAACCGCATC<br>AAGCTCTTGGAAGAGATTCTGTCTTTTCGTATGCAGGGCGTTGAGTTCGATAATGGTGA<br>TATGTATGTTGACGGCCATAAGGCTGCTTCTGACGTTCGTGATGAGTTTGTATCTGTTA<br>CTGAGAAGTTAATGGATGAATTGGCACAATGCTACAATGTGCTCCCCCAACTTGATATT<br>AATAACACTATAGACCACCGCCCCGAAGGGGACGAAAAATGGTTTTTAGAGAACGAGA<br>AGACGGTTACGCAGTTTTGCCGCAAGCTGGCTGCTGAACGCCCTCTTAAGGATATTCG<br>CGATGAGTATAATTACCCCAAAAAGAAAGGTATTAAGGATGAGTGTTCAAGATTGCTGG<br>AGGCCTCCACTATGAAATCGCGTAGAGGCTTTGCTATTCAGCGTTTGATGAATGCAATG<br>CGACAGGCTCATGCTGATGGTTGGTTTATCGTTTTTGACACTCTCACGTTGGCTGACGA<br>CCGATTAGAGGCGTTTTATGATAATCCCAATGCTTTGCGTGACTATTTTCGTGATATTGG<br>TCGTATGGTTCTTGCTGCCGAGGGTCGCAAGGCTAATGATTCACACGCCGACTGCTAT<br>CAGTATTTTTGTGTGCCTGAGTATGGTACAGCTAATGGCCGTCTTCATTTCCATGCGGT<br>GCACTTTATGCGGACACTTCCTACAGGTAGCGTTGACCCTAATTTTGGTCGTCGGGTAC<br>GCAATCGCCGCCAGTTAAATAGCTTGCAAAATACGTGGCCTTATGGTTACAGTATGCCC<br>ATCGCAGTTCGCTACACGCAGGACGCTTTTTCACGTTCTGGTTGGTTGTGGCCTGTTG<br>ATGCTAAAGGTGAGCCGCTTAAAGCTACCAGTTATATGGCTGTTGGTTTCTATGTGGCT<br>AAATACGTTAACAAAAAGTCAGATATGGACCTTGCTGCTAAAGGTCTAGGAGCTAAAGA<br>ATGGAACAACTCACTAAAAACCAAGCTGTCGCTACTTCCCAAGAAGCTGTTCAGAATCA<br>GAATGAGCCGCAACTTCGGGATGAAAATGCTCACAATGACAAATCTGTCCACGGAGTG<br>CTTAATCCAACTTACCAAGCTGGGTTACGACGCGACGCCGTTCAACCAGATATTGAAG<br>CAGAACGCAAAAAGAGAGATGAGATTGAGGCTGGGAAAAGTTACTGTAGCCGACGTTT<br>TGGCGGCGCAACCTGTGACGACAAATCTGCTCAAATTTATGCGCGCTTCGATAAAAAT<br>GATTGGCGTATCCAACCTGCA |

TABLE 4

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nmTriangle01 | 15 | AGTAAGCAGATAGCTCAGAGCAGGCGAACAA |
| 10nmTriangle02 | 16 | GAAATAGCTAATAACGGAAGAGCCCACCATACCC |
| 10nmTriangle03 | 17 | AGTTTACATACATAAAGGTGGCAACATAAGAACCACGCCGCCAG |
| 10nmTriangle04 | 18 | AAACGCAAAATAGCTAAGAAA |
| 10nmTriangle05 | 19 | AGGTTGAGCGATTGGCAAATCCTCATAACAAT |
| 10nmTriangle06 | 20 | AAAAGAACTGGCATGTAGAAAAACCAGAAG |
| 10nmTriangle07 | 21 | TAGCGTTTCCCTCAGAGCCTAATCCACCGACCAC |
| 10nmTriangle08 | 22 | CCCTGCAAAGACACCACGGAATAAGTTTGATAGCAGAGTAGCGA |
| 10nmTriangle09 | 23 | CCTCAGAGCCGCCAAAAGAAACCAGAGCCG |
| 10nmTriangle10 | 24 | GAGCCACCACCGGATCAGATAGCGACCGCCT |
| 10nmTriangle11 | 25 | AACCGCCAGCCATCTTAACCA |
| 10nmTriangle12 | 26 | TTTGCCTTCTGTAGCGGTCATAGCCCCCTTAT |
| 10nmTriangle13 | 27 | ATTCTGAAACCATTTGTCACATTAGCAA |
| 10nmTriangle14 | 28 | TACCAATCAATACGCAGTATGTTAGCAATTAAGACTCCAAAGAC |
| 10nmTriangle15 | 29 | GTCACCAACACCGACTGCCAG |
| 10nmTriangle16 | 30 | CATTCAACAGGGAAGGTCATTAAAGGTGAATTATC |
| 10nmTriangle17 | 31 | CAAAATCACCAGTAGAGGGCGATTGCACCAT |
| 10nmTriangle18 | 32 | ACCGTATATGGTTTACCAGCGCCTTATTAGAAA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nmSquare01 | 33 | GACTTATAGCCCCCACAGACAGCCCTCACAACGCCTGGAGGTTT |
| 10nmSquare02 | 34 | CCCTCAGATCAGAACCGAACCGAACTTTTGAT |
| 10nmSquare03 | 35 | GATTAGCGAGTGTACTGAAAC |
| 10nmSquare04 | 36 | GATACAGGTGTATCACCGTACTCAGTAGCATTGGAA |
| 10nmSquare05 | 37 | ATGAAAGTATTAAGCACCCACCGCAGGCTGA |
| 10nmSquare06 | 38 | TAGGGGGTTTTGGATATAAGCCTCAAGA |
| 10nmSquare07 | 39 | TTTTGTACAAACGTTAGCGTTACCGTAA |
| 10nmSquare08 | 40 | ATAGCAAGCCCAATCTAAATTTTGAGGAACC |
| 10nmSquare09 | 41 | CCATGTTAGTCGTCTTTCCAGACGTTTAATTGAAAG |
| 10nmSquare10 | 42 | CATGAACGATCTTATCGGTTTATCAGCTAAGGAGCCTTAGTAAA |
| 10nmSquare11 | 43 | CGTCACCACTTAGCCGCAGGG |
| 10nmSquare12 | 44 | GTATGGGACAACTTTCAAATCCGCGACCTGCT |
| 10nmSquare13 | 45 | GCCACTACGTTAATGCTGAGTAACAGTGCCCGAGGC |
| 10nmSquare14 | 46 | CTCAGCAGGAATACACAAGGCCGCAACG |
| 10nmSquare15 | 47 | AAAAAGGAAGTTTCCATTAAGGCGGATATTTT |
| 10nmSquare16 | 48 | CTAATAAAGACTAGTGCCGTCGAGAGGGCAGTACCAACGGGTAA |
| 10nmSquare17 | 49 | AAAGTATAAACAGAAGGCACCAAC |
| 10nmSquare18 | 50 | CATGCGAAAGACTTGAGGACTTTTGCGG |
| 10nmSquare19 | 51 | AATTGTGAATTTGCAACGGCTACAGAGGCATCGGAATGCGCCGA |
| 10nmSquare20 | 52 | AACCATCGACCGATATTATACCAAGCGCGAAA |
| 10nmSquare21 | 53 | AACAAAGGCTCCCTTTCGAGTTTTCACG |
| 10nmSquare22 | 54 | CCAAAAAAAACGGAGAGAACA |
| 10nmSquare23 | 55 | ACTAAAGGAATTGCGCATACCCACGAATAAT |
| 10nmSquare24 | 56 | CAAAGTACGCTTGATACCGATAGTCGAGGGTACTTA |
| 10nmSquare-spacer01 | 57 | TGTATCATCGCCTGATAAATTGTGT |
| 10nmSquare-spacer02 | 58 | AAACACTCATCTTTGACCCCCAGCG |
| 10nmSquare-spacer03 | 59 | CACCCTCAGAGCCACCACCCTCATT |
| 10nmSquare-spacer04 | 60 | CCTGCCTATTTCGGAACCTATTATT |
| 10nmSquare-spacer05 | 61 | CAGTTTCAGCGGAGTGAGAATAGAA |
| 10nmSquare-spacer06 | 62 | TAATAAGTTTTAACGGGGTCAGTGC |
| 10nmSquare-spacer07 | 63 | ACGAGGCGCAGACGGTCAATCATAA |
| 10nmSquare-spacer08 | 64 | TCGGTCGCTGAGGCTTGCAGGGAGT |
| 10nmPentagon01 | 65 | CTTGCCCTACTAATGCAGATACATATAGCGTCCACA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nmPentagon02 | 66 | AATAAAACGACGAGAAAACTG |
| 10nmPentagon03 | 67 | TTCAGAACTAACTGAGATTTGGAAGAAA |
| 10nmPentagon04 | 68 | GAGGCATACACTATCAATATGTACCCATAAGG |
| 10nmPentagon05 | 69 | GTTGAGGAATACCAATACTGCGGAATCGTAGACTGGAACGCCAA |
| 10nmPentagon06 | 70 | GCTCATTATACCAGAGCAAGTAAGTCAGGAC |
| 10nmPentagon07 | 71 | GAGAATCGAAATGCTTTAAACAGTAACCAGACTCCC |
| 10nmPentagon08 | 72 | CATAAATCTCTTTACCAGTCTGGAGCAAACAA |
| 10nmPentagon09 | 73 | CCAAAATAGCGAGATCAGGAAAAAGGCTTTT |
| 10nmPentagon10 | 74 | CCTCGTAAAATGATAAATATAAGAAGTT |
| 10nmPentagon11 | 75 | GCAATCATTGAACGGAAGCAAACTCCAATCAAAGCGTCAGAAAA |
| 10nmPentagon12 | 76 | GGGTAATAATGAACGGAAAAA |
| 10nmPentagon13 | 77 | GGAGAGCCTCAGGACCCTGTAAAGAATT |
| 10nmPentagon14 | 78 | ATGTAAGCCTTTATTTCAACTATTACAGTGCG |
| 10nmPentagon15 | 79 | ATGCAATACTTTGTAGAAAGATTCATCAAACAACATGCAAGGAT |
| 10nmPentagon16 | 80 | AGCAATAAGTAGGTAAGGCAAGGCAATG |
| 10nmPentagon17 | 81 | AGAACCCTTAATCATTCTTGAGATGGTTTAATAGTA |
| 10nmPentagon18 | 82 | CCTGTTCAACTTCATATATTTTAA |
| 10nmPentagon19 | 83 | TGATTCCCTGATATTCATATG |
| 10nmPentagon20 | 84 | TGGCATCATAGTAGTAGAGACAGTCAAATCAC |
| 10nmPentagon21 | 85 | AAGTGTCAATAATTGTACCAAAAACATTCATAAAGCGGGCGCGA |
| 10nmPentagon22 | 86 | CAACTAAAGTACGGACTAAATTCTTGTCTGG |
| 10nmPentagon23 | 87 | TTTAAATTCTGCCGCAAATGTTCATTCC |
| 10nmPentagon24 | 88 | CATCAATAGCTATATTTTCATTTGTAAATCGGCCTG |
| 10nmPentagon25 | 89 | TTTTTGAGATTGCTCCTTTTGATAATTTAGTTTACC |
| 10nmPentagon26 | 90 | TTTAAATTCGAGGGTCAGGACCGAAAGA |
| 10nmPentagon27 | 91 | TGCATCAAAAAGATAATTGAGCTTTAAGAGG |
| 10nmPentagon28 | 92 | AAGCTTAGAGAGTGACCATTAGATACATACGAGTAGAGAGGTCA |
| 10nmPentagon29 | 93 | TGGCTTAGCTGAATATCCGGAGAGGGTAGCTA |
| 10nmPentagon30 | 94 | CGCGTTTTAGATCTACCGGAT |
| 10nmPentagon-spacer01 | 95 | ACCAGAACGAGTAGTAAATTG |
| 10nmPentagon-spacer02 | 96 | GACTATTATAGTCAGAAGCAA |
| 10nmPentagon-spacer03 | 97 | ATCGTAAAACTAGCATGTCAA |
| 10nmPentagon-spacer04 | 98 | TGCTGTAGCTCAACATGTTTT |
| 10nmPentagon-spacer05 | 99 | GAATTACCTTATGCGATTTTA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nmPentagon-spacer06 | 100 | ACCCTCGTTTACCAGACGACG |
| 10nmPentagon-spacer07 | 101 | ATTCAAAAGGGTGAGAAAGGC |
| 10nmPentagon-spacer08 | 102 | ATTAACATCCAATAAATCATA |
| 10nmPentagon-spacer09 | 103 | AGGCTATCAGGTCATTGCCTG |
| 10nmPentagon-spacer10 | 104 | CCGTTCTAGCTGATAAATTAA |
| 10nmHexagon01 | 105 | AATAGCGACAAAAGAACCGTGCATCTAACTTT |
| 10nmHexagon02 | 106 | AATCATTGTAACCCTCGTTTACCATTAAACAGCACT |
| 10nmHexagon03 | 107 | AAAGAAGAGCAATTCAGAAAACGAGAATCAAATGCTGACGACGA |
| 10nmHexagon04 | 108 | ATCACACATTCAGGCATAGTATTCATCA |
| 10nmHexagon05 | 109 | AGGAATACTGAATTACTAACG |
| 10nmHexagon06 | 110 | GAACAACATTATTATTTTGGAGGCCAGGTAG |
| 10nmHexagon07 | 111 | TATTCATTGTCACGTTTAAAA |
| 10nmHexagon08 | 112 | TGGGATAGACCCTGACTATTATAGCTCCTTTTAGGT |
| 10nmHexagon09 | 113 | AATACAAAAATCGATAAGAGGTCATTTTTTTAATTGTCAGAAGC |
| 10nmHexagon10 | 114 | CTTTGAATCCCCCCATAAATCTGCGGAA |
| 10nmHexagon11 | 115 | GCATCAAAGGAAGCCCGGCGGATTGACCGTAA |
| 10nmHexagon12 | 116 | TGTTTAGACTGGATTAAGAAAGATAGCGTCC |
| 10nmHexagon13 | 117 | TTATATGCAATGTTGCCTGAGAGTCTGGAAAGGCTATCAAAAGG |
| 10nmHexagon14 | 118 | CCGGAGACCCATCAATTATTTTGTTAAAATTC |
| 10nmHexagon15 | 119 | AGTAGCCTTTATTATTTTAAGACCCTGT |
| 10nmHexagon16 | 120 | AAATCGGTTGTACCAATCAAGTCAAAAAACA |
| 10nmHexagon17 | 121 | CGGGAGAATTTTTGTTAAGCT |
| 10nmHexagon18 | 122 | GCATTAAAATGTGTAGGTAAAGATTCAGGTCACCTG |
| 10nmHexagon19 | 123 | CAGGGGACGTTGAATCAGAAAAGC |
| 10nmHexagon20 | 124 | CGGTTGATGGAAGAAACTCATTATACCAGTCAAAGA |
| 10nmHexagon21 | 125 | CCCAAGAATCGACGCCAAAAGGAATTACTAATGCAGTGTCAATC |
| 10nmHexagon22 | 126 | TATTTTTGATAAGCAAGATAAATTAAAA |
| 10nmHexagon23 | 127 | CGGTAGAGATCTCAAACAAGAATGCCGG |
| 10nmHexagon24 | 128 | TTGTAATCGTAAAACTAGCAATACATAATGAA |
| 10nmHexagon25 | 129 | ACTAGGTCAATAGAAAAGGTTTGACCAT |
| 10nmHexagon26 | 130 | GGCAAGGCCAAAATTAATAGGAACGCCATCAA |
| 10nmHexagon27 | 131 | AAATAATTATAGTAGTAGCATTAAGGATAAAATTCT |
| 10nmHexagon28 | 132 | AATTCTGCGAACGAATTAGAAAGAGTAGATT |
| 10nmHexagon29 | 133 | TCGCAAATCGCGTCTGTTCCC |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nmHexagon30 | 134 | TAGTGGCATCAAATTTTTAGAACCCTCACAACGCAACATCCAAT |
| 10nmHexagon31 | 135 | TGCTAGAGAGTACGGATGGCGAAGCAAA |
| 10nmHexagon32 | 136 | ACCGTTAGAGCTTCATTTGGGGCGCGAGCTGTTTAGCTCAACAT |
| 10nmHexagon33 | 137 | TCAGGATTCAACCCGTTTAAT |
| 10nmHexagon34 | 138 | TCGAGCTTCAAAGCCGGTGAAGTAGAACCAG |
| 10nmHexagon35 | 139 | TGCAACTATCTGGAAGTCAACATTAAATGTGA |
| 10nmHexagon36 | 140 | GCGAGTAAGAATATAATGCTGTAGCTATATTTTAAT |
| 10nmHexagon-spacer01 | 141 | ATTTAAATTGTAAACGTT |
| 10nmHexagon-spacer02 | 142 | TCATTCCATATAACAGTT |
| 10nmHexagon-spacer03 | 143 | TGTAGATGGGCGCATCGT |
| 10nmHexagon-spacer04 | 144 | GATTCTCCGTGGGAACAA |
| 10nmHexagon-spacer05 | 145 | ATCAGCTCATTTTTTAAC |
| 10nmHexagon-spacer06 | 146 | CTTCCTGTAGCCAGCTTT |
| 10nmHexagon-spacer07 | 147 | TCTACGTTAATAAAACGA |
| 10nmHexagon-spacer08 | 148 | TTTGCCAGAGGGGGTAAT |
| 10nmHexagon-spacer09 | 149 | AAGACTTCAAATATCGCG |
| 10nmHexagon-spacer10 | 150 | TATGCGATTTTAAGAACT |
| 10nmHexagon-spacer11 | 151 | CAATAAAGCCTCAGAGCA |
| 10nmHexagon-spacer12 | 152 | GATATTCAACCGTTCTAG |
| 20nmTriangle01 | 153 | GTAGTCGTCGCTTAGCTTAGTGAGAAGAG |
| 20nmTriangle02 | 154 | CGTTAGAACGCGAAAAAAGCCTGTGCTAAGTTCATTAG |
| 20nmTriangle03 | 155 | AATAGTTTAACGTCAGATGAACCATATCATCATTTTATAT |
| 20nmTriangle04 | 156 | ATTATTTGCACGTAAAACAGATTGC |
| 20nmTriangle05 | 157 | AATAAATGATGAAACAAATTAATTACATTTAACAATTTCACTT |
| 20nmTriangle06 | 158 | CTTGAAAACGAATTATAGCAAAAGAAGAGAAA |
| 20nmTriangle07 | 159 | CGACAATAAACAACATTGCAGAACTGTTTTGA |
| 20nmTriangle08 | 160 | AAAAGAAAATTTTCAGCCAAGTTACAAAA |
| 20nmTriangle09 | 161 | GAACAATTACTAGGAAAACTTTTTCAAATAATAGATTCAATTCGA |
| 20nmTriangle10 | 162 | GAGCGGAATTGTTTGGGGAAGGGTTAGAACCTATA |
| 20nmTriangle11 | 163 | AACCATTAAATCTAACAGTAACAATAACGGAT |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nmTriangle12 | 164 | TCGCGCAGAGGCATAGCGAATT |
| 20nmTriangle13 | 165 | TCGCCTGATTGCTATTAGACGAA |
| 20nmTriangle14 | 166 | GCAATTCATCAATATAATCCTGATTATCATCGCG |
| 20nmTriangle15 | 167 | ATAATACATTAAGACAAATTAATTTTGTAACATTAAA |
| 20nmTriangle16 | 168 | ATTAAGGATTTAGAAGTTTG |
| 20nmTriangle17 | 169 | TACAGCTTTGCCCTTTACAAAAGAGCCGTCAATAG |
| 20nmTriangle18 | 170 | TGAGTGAATAACATGGAAACCCAGACGA |
| 20nmTriangle19 | 171 | TCAATAGTGAATTTACTATATGTATTTTCCCTATG |
| 20nmTriangle20 | 172 | AATTAAAATGCTGTTATCAACAATAGATAAATTCTGTAGTACATA |
| 20nmTriangle21 | 173 | TTTTACTTGCTTCGCGCCTGTATGCAAATCCAATCGCTGAGACGC |
| 20nmTriangle22 | 174 | TCCTGATTATCAGATATTACTTTGAGATG |
| 20nmTriangle23 | 175 | TATCATATGCGTTATACAAATTCGAATCATAAAGA |
| 20nmTriangle24 | 176 | TTGCTCACTTGCCTATCATTCC |
| 20nmTriangle25 | 177 | TAGAGTCTGTCCCTTCTGACACGTGGCACAGA |
| 20nmTriangle26 | 178 | AATAAAACCCTCAATTGAGGAAAATATCT |
| 20nmTriangle27 | 179 | TTAGGAGCACTAACATTTTAGTTTCTGGTCAAAAG |
| 20nmTriangle28 | 180 | TTTACCCGCCAGCCATTGCAACAGGAAAAGCC |
| 20nmTriangle29 | 181 | ATATAATCGCCATATTTAACAACGCCAATCTTTCCTTGAG |
| 20nmTriangle30 | 182 | CATCACCTTGCTGAGCCAGCAAGCCAAC |
| 20nmTriangle31 | 183 | AAGGTCTGAGAAGTGTATGG |
| 20nmTriangle32 | 184 | AATGGTTTGAAACGGGTATTAAACCAAGTACCAAAGGGATGCCACCGA |
| 20nmTriangle33 | 185 | CAATAAATTTCATTAAATAAGAATAAACACCAGTATAAGCAAATG |
| 20nmTriangle34 | 186 | GCTCAACAGTAGGGCTGTGATAAAAATTTCTT |
| 20nmTriangle35 | 187 | CAATATTTTTGATTTTATAAAAT |
| 20nmTriangle36 | 188 | GCTGAGAACCTCATAAGGCGTCTTCTGACCTAAATTTATCTATCT |
| 20nmTriangle37 | 189 | AAGAATACCGACCGTTAATTGAGCCAGAA |
| 20nmTriangle38 | 190 | GTCACCCACCAGCAGAAGGCGGTCAGTATTAACACCGCCTCAC |
| 20nmTriangle39 | 191 | ATCAACAGGCCCTAAATACCGAACGAAACGAC |
| 20nmTriangle40 | 192 | AATACATCAAAGGGACTAGTCTTTAATGC |
| 20nmTriangle41 | 193 | CAATAAGTGCGCAACTTAATTGGCAGATTCACCACAGT |
| 20nmTriangle42 | 194 | TAACCGTTGTAGCTGATTAGTTTA |
| 20nmTriangle43 | 195 | GCGAACTGATATTGAAAGGAAT |
| 20nmTriangle44 | 196 | CTATATTCTGGCCAACAGAGGAAATGGAAATAACATGGTA |
| 20nmTriangle45 | 197 | GAACCATCACGCATCAGTGAGTTTAGACAGGAACGGTACGCCAGA |
| 20nmTriangle46 | 198 | AACTATCGACGCTCATTGACGCTCAATCGTCTATA |
| 20nmTriangle47 | 199 | TGAACGCTACAGCTTTCCTCGAGCGGGAG |
| 20nmTriangle48 | 200 | TTTAAGGGGAAAGCCGAGGAAGGGAAGAAAGCGAAAGGAGGGC |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nmTriangle49 | 201 | CACCACACCCGCCAAGTGTAGGCAGAGG |
| 20nmTriangle50 | 202 | GTATAACAGGGAGAATTAACTGAACACCCAAGTTTTCAATAGCACGC |
| 20nmTriangle51 | 203 | GTTAGATTACCGCGCCTTGG |
| 20nmTriangle52 | 204 | GAGCACGTGAACCCTATAGAGCTTGACCGTCA |
| 20nmTriangle53 | 205 | CATTTTCGAGCCAGTATTACGAGCATGTCCCG |
| 20nmTriangle54 | 206 | ATTTATATAAAGTACCGACAAAAGGTAACCTGAACAAAATCAAGTCCG |
| 20nmTriangle55 | 207 | CTATTTTGGAGCCTAATAAACAGCCATATTATAACATAAATCTA |
| 20nmTriangle56 | 208 | GGTCCCTTTACAGAGAGAATTTATCCCAGAGGTTTTTACA |
| 20nmTriangle57 | 209 | GCACTAAATCGATAACGTGGGC |
| 20nmTriangle58 | 210 | CCTCCGGAATATCCCATCCTAATATAAGAGATATCCT |
| 20nmTriangle59 | 211 | GAACCCGCAATAGCAGGAGGTGCCGTAAA |
| 20nmTriangle60 | 212 | GCGTAGAACAAGCACCAATCAATAATCGGGTAATTTAGCGGTCAC |
| 20nmTriangle61 | 213 | AGAAAGCAAATCGGTCTGAGAGACTACCTTTTAGGACATCGTTAA |
| 20nmTriangle62 | 214 | CAAATCCAACGCTAACGAGCGTCTTTCCACACCCAGCGAA |
| 20nmTriangle63 | 215 | GAATCGCTAGCGGGCTTAAAGAAACGATTTTTTGAAAA |
| 20nmTriangle64 | 216 | GAGGCGTTTTAGCACTTGCGGATC |
| 20nmTriangle65 | 217 | GCCTTAGAAAAATCTTAGGTTGGGTTATAAAATCATAAGATATAG |
| 20nmTriangle66 | 218 | GCTGGCGCGCTTAATGTAGAAAAGCCGTTTTTATTTTATCAATCA |
| 20nmTriangle67 | 219 | CTAAACAGGAGGCCGCTCATCGACTATGGTTTAAC |
| 20nmsquare01 | 220 | TAGTACCAAAATAGCGAGAGGCTTTTGCCATAACGCTCATAAAT |
| 20nmsquare02 | 221 | CGAGTAGTAAGATTCATCAG |
| 20nmsquare03 | 222 | ATAGCGTCACCATAAAGGTAACGCCAGG |
| 20nmsquare04 | 223 | GTTTTCCCAGTCCAGAGGGGCGGA |
| 20nmsquare05 | 224 | GATAAAAAGGAAGATTTAGAAGTTTTGCACGACGTTTAAAC |
| 20nmsquare06 | 225 | ATTCATTGAAATGCTTGTAAAACGACGCAGAA |
| 20nmsquare07 | 226 | ATCGCAAAAGGAATTACGAGGCATAGTACGATAAAAAAAATGTT |
| 20nmsquare08 | 227 | TTGATACCACATAATATTTTGTTAAAATTTAAATTGCGGAACAA |
| 20nmsquare09 | 228 | AGTTCAGAAAACGAGAATGCAATACTGGTAA |
| 20nmsquare10 | 229 | CTAATAAACGTTTCAACTAATGCA |
| 20nmsquare11 | 230 | AATCTACGTTAATACCCTCAATCCAAACGAA |
| 20nmsquare12 | 231 | CAGGTAGAAAATTGGGAGAAA |
| 20nmsquare13 | 232 | ACGCCAGCCTTCAAATATCG |
| 20nmsquare14 | 233 | GAAGCTGTCGAGTTAATTAGCTCAACATATCGGTGCGACCA |
| 20nmsquare15 | 234 | CGTTCTTCAAAGCCCTCGTTTACCAGACAGCAACACAAGATTAA |
| 20nmsquare16 | 235 | CAGAAGCAAAGCGGGTAGAAACGAATTGCAT |
| 20nmsquare17 | 236 | CAACAGAGCTTAATTGCTGAATATAATGCAAACTCCGATTCCCA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nmsquare18 | 237 | CAAATATCATAACGAACCAGACCG |
| 20nmsquare19 | 238 | AGTTAACAGGTCAGGATTAGAGAGTACCGATGGCTTTAAAGTAC |
| 20nmsquare20 | 239 | GAAGTTTCGGTCAATAGCTGCGCAACTG |
| 20nmsquare21 | 240 | TTAGATACATTTCGCAAATATTCCATATATG |
| 20nmsquare22 | 241 | TTGGGAAGGGCGGTTTTAAATAAC |
| 20nmsquare23 | 242 | CCGAAAGATGGCGAAAATAGT |
| 20nmsquare24 | 243 | ATTCTGCGTTTAGTTTGGGCCTCTTCGCTATT |
| 20nmsquare25 | 244 | CAGCTCATTTTTGCCCCAAAATGTGAGC |
| 20nmsquare26 | 245 | TCAAAACATTAAAACAGGAAGATT |
| 20nmsquare27 | 246 | GATGGGCGTCGTAAAACTAG |
| 20nmsquare28 | 247 | GTATAAGCAAATGCATTAAACGCGTCTG |
| 20nmsquare29 | 248 | AGCACCTGTAATGTTGATAATCAG |
| 20nmsquare30 | 249 | AACGGTAACATCGTAATATCA |
| 20nmsquare31 | 250 | GAGTAACATTCTCCGTAGGTCACGTTGGTGTA |
| 20nmsquare32 | 251 | GTAGCCAGTAAGAACTATTGTGAATTACCTTATTGACCGTGCCA |
| 20nmsquare33 | 252 | CATGGTACCCCGACTTTTGCGGGAGAAGATTATGACAACAAGAG |
| 20nmsquare34 | 253 | AAAATAACATATTCAATCCAATAGGAACAATGGGATGGGA |
| 20nmsquare35 | 254 | ACAAACGGCGGATGCGATTTCTTT |
| 20nmsquare36 | 255 | CATCAAATAATTTTTTTGTTAAAT |
| 20nmsquare37 | 256 | GGTCATTGCCTGAGTCGGAACCCGAGTCTGG |
| 20nmsquare38 | 257 | GCCGAAAGCTAAATCGGTTGTACCAAAATTTATTTCGTAATGTG |
| 20nmsquare39 | 258 | GCAATAGCAAAATAAGAGGTCATTTTTGTAATTGCTAATAGTAG |
| 20nmsquare40 | 259 | CTGAAACGCAAGGATAAAAATTTTTAGACAGAGCATGAGACAGT |
| 20nmsquare41 | 260 | CTAGCTGATAAATTAATGCAGGGTGAGATGC |
| 20nmsquare42 | 261 | TACTCCTTTTGATTAAGCAATAAA |
| 20nmsquare43 | 262 | GCCTACCAGAATGGCAACTCATATATTTGCACTCCACCGTT |
| 20nmsquare44 | 263 | ACATCCAAGTGCCGGAGCGAG |
| 20nmsquare45 | 264 | CGCTTCTGTAAATCATACAG |
| 20nmsquare46 | 265 | CTCAGGAAGATCTAAATGCAAAAG |
| 20nmsquare47 | 266 | GATTCAAACGGAGAGGGACAGTATCGGC |
| 20nmsquare48 | 267 | CAAATCACATATTCAAGCCAGCTTTCCGGCAC |
| 20nmsquare49 | 268 | CTGAAAAGGTGGCAATATGCATCATCAATTC |
| 20nmsquare-spacer01 | 269 | AAAAATCAGGTCTTTACCCTGACTA |
| 20nmsquare-spacer02 | 270 | CTGTTTAGCTATATTTTCATTTGGG |
| 20nmsquare-spacer03 | 271 | TGAGATGGTTTAATTTCAACTTTAA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nmsquare-spacer04 | 272 | CCAGGCAAAGCGCCATTCGCCATTC |
| 20nmsquare-spacer05 | 273 | CTCATTATACCAGTCAGGACGTTGG |
| 20nmsquare-spacer06 | 274 | GTGCATCTGCCAGTTTGAGGGGACG |
| 20nmsquare-spacer07 | 275 | AGCTATTTTTGAGAGATCTACAAAG |
| 20nmsquare-spacer08 | 276 | GGGATGTGCTGCAAGGCGATTAAGT |
| 10nm3merTip-01 | 277 | AAACAGGTCGTCAAACTATCAAAACATTACCA |
| 10nm3merTip-02 | 278 | TCCTAAGCGCCGAAGAAGCTGGAGTGTCTGTA |
| 10nm3merTip-03 | 279 | GCGCACCTAAGAAAAAGAGTAAACAGATTAAAC |
| 10nm3merTip-04 | 280 | GACGGGAGTGGAGAATGTAGCTTTAACAGAAGT |
| 10nm3merTip-05 | 281 | GAGAACCAGCTTATCAGAAAAAAAGTAGTGTT |
| 10nm3merTip-06 | 282 | AACAGTCGGGGTTAATCGTGCCAAGATTTTAT |
| 10nm3merTip-07 | 283 | CTCAGGAAGTCGCAGTAGGCGGAAGTACTGAA |
| 10nm3merTip-08 | 284 | TGGCGAGAAATAAAAGTCTGAAACGTGCCATG |
| 10nm3merTip-09 | 285 | CATGAAACGCAAAGGTCAATATAACTTGAATTA |
| 10nm3merTip-10 | 286 | GCATTAACCGTTGACAGATGTATCACAACCTGAATTAAAA |
| 10nm3merTip-11 | 287 | TCTCTTTAGCCAGCAATATCGGTACATACAAACCAGAAAA |
| 10nm3merTip-12 | 288 | TGGTATCAGTTGTTATAGATATTCACGGCGCTTGTTCACC |
| 10nm3merTip-13 | 289 | CAGCAATCAAGAAGGTATACGAAGGGCGAATAAGTACGCGTGGTtcatcttcacactact |
| 10nm3merTip-14 | 290 | GACGGAAGGAGTGAGAGCGCCAACGGCGCATGAACTGTAAtcatcttcacactact |
| 10nm3merTip-15 | 291 | TGGGAAGCCTTCAATTTAACATCAtcatcttcacactact |
| 10nm3merTip-16 | 292 | TGGTATAGCCAGATGCCCAGCAGTtcatcttcacactact |
| 10nm3merTip-17 | 293 | CGGTACGGCAACGGAATCTTGATTGCGGAGCAtcatcttcacactact |
| 10nm3merTip-18 | 294 | CACGTCCAAATGGTCAGCGTCATAAGAGGGTCTGTTTCAAtcatcttcacactact |
| 10nm3merTip-19 | 295 | TATATCAGGCATATAACCCTAAGCTCATtcatcttcacactact |
| 10nm3merTip-20 | 296 | GTCAGGCAAGTTAGTCAAAGAACATCCTtcatcttcacactact |
| 10nm3merTip-21 | 297 | ACCGAAGACATCATGGAAACATCAGACCAGCAAGGAAGCCATAAtcatcttcacactact |
| 10nm3merTip-22 | 298 | GGTAGAAGTCGTGTTTTACCTTCTtcatcttcacactact |
| 10nm3merTip-23 | 299 | GATGGCAGCATTTGGCAGGAGGAACAGTATGCAAATTAGCTAATtcatcttcacactact |
| 10nm3merTip-24 | 300 | CACGCGGCTTAAACTTGAACGGAAGCGCATAAtcatcttcacactact |
| 10nm3merTip-25 | 301 | ATATCAGCAGACTCAAAAAAAATTTAGGCAGTtcatcttcacactact |
| 10nm3merTip-26 | 302 | ATCTGTCTACAGTAGAGTCACATAtcatcttcacactact |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nm3merTip-27 | 303 | CATACTGACTATATAAACGGTCACATTAACCCCTCACACTtcatcttcacacta ct |
| 10nm3merTip-28 | 304 | AGTTTGAACCACTCCATCTCACCAtcatcttcacactact |
| 10nm3merTip-29 | 305 | CCTTACCAACAGTCTGAATGTAGGGTCGtcatcttcacactact |
| 10nm3merTip-30 | 306 | TGGTCTTTTATCACGAAGTCTAACtcatcttcacactact |
| 10nm3merTip-31 | 307 | cctacgagtcagtcctTCCAGAACACGAACAGGGTCTGTT |
| 10nm3merTip-32 | 308 | cctacgagtcagtcctGCATGAAGATAAGCAGGTCAATAGATGT |
| 10nm3merTip-33 | 309 | cctacgagtcagtcctCTCAGCGGCAAAATTAGCGGCTTG |
| 10nm3merTip-34 | 310 | cctacgagtcagtcctAAATCAATAACAGGCATTGAAGAAAACCTAACGTT |
| 10nm3merTip-35 | 311 | cctacgagtcagtcctATGAGGGAATAGCAAGGAAAGACGCGCCAGCG |
| 10nm3merTip-36 | 312 | cctacgagtcagtcctCGTTTGGTAGATTAGAGGACGGTTAAGAAATA |
| 10nm3merTip-37 | 313 | cctacgagtcagtcctAAATGGTAAAGATGGGACGCTCGGCGCC |
| 10nm3merTip-38 | 314 | cctacgagtcagtcctCAATCACCTTCGCCGCGCTTTAGCGTTACGAACAA |
| 10nm3merTip-39 | 315 | cctacgagtcagtcctAAAATAATCCACTTAAAATACCAT |
| 10nm3merTip-40 | 316 | cctacgagtcagtcctCATCGAACAGAACGGCAACAAATGCTTAAAAGCGG |
| 10nm3merTip-41 | 317 | cctacgagtcagtcctCGGCGTTAATGATTGAAGATTGCGTCCACTGC |
| 10nm3merTip-42 | 318 | cctacgagtcagtcctGGAAACACTTCTTGCATTCCTGAATGAA |
| 10nm4merTip-01 | 319 | ACAGTATTGTTATCGGTAGCAAGCAACTTAAT |
| 10nm4merTip-02 | 320 | CCACTGTTTTAACAGTCGGGAGAGAATATAAC |
| 10nm4merTip-03 | 321 | CAGGTAAACCACCAGTTAGGAACATCCATGCCT |
| 10nm4merTip-04 | 322 | TAACAGGTCTTTATACCATCCTTCAATCACCTT |
| 10nm4merTip-05 | 323 | ACAGAATGCAAGCGCAAGAGTAAAGTAGGCGG |
| 10nm4merTip-06 | 324 | GAATGCCACCGGAGGCGGCTTTTTAACGCGGC |
| 10nm4merTip-07 | 325 | AGAACAGCAACCGCATAAAAGTCTGCAAGAGCA |
| 10nm4merTip-08 | 326 | AATGGCAGGAAACAAAACTAGGGATTTAGCCA |
| 10nm4merTip-09 | 327 | GAAGCAATATTTAATACCAGCATCGAGCCTTG |
| 10nm4merTip-10 | 328 | ATGCGAAAAAAGCATCAGGAACAAACCGCCTCC |
| 10nm4merTip-11 | 329 | AAACTCCTCAGAAAAAAAGTTTGAGTGAGAAC |
| 10nm4merTip-12 | 330 | AAACAATTTAGACATGGCGCCACCACATGATT |
| 10nm4merTip-13 | 331 | CATATCAAGCAAACCTTCAAGGCAGACTtcatcttcacactact |
| 10nm4merTip-14 | 332 | AAATCCGGTCGGCAATAGTTGCATGACCAGCAAGGAAGCCATAAtcatctt cacactact |
| 10nm4merTip-15 | 333 | CAACCAAACGTCAACCTTATCAGCTTTAGTAAtcatcttcacactact |
| 10nm4merTip-16 | 334 | GACGGAAGGAGTCATCATCTCAACGGCGAAAAGTAAGAAAtcatcttcacact act |
| 10nm4merTip-17 | 335 | AGTTTGTGCATCTCCATCTCACCAtcatcttcacactact |
| 10nm4merTip-18 | 336 | ATCTGAGAGCGCTGATTAAGGCAAtcatcttcacactact |
| 10nm4merTip-19 | 337 | AGAACCCTGAAACGTGCCAAAAAATAGTtcatcttcacactact |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nm4merTip-20 | 338 | AACGGAGCGCATTAAACTTCAGATtcatcttcacactact |
| 10nm4merTip-21 | 339 | ATCATTGTCAGCAGCAATCTGACAAGTAAACTGGCCAGAGtcatcttcacactact |
| 10nm4merTip-22 | 340 | AAGCGGAGATGTCAATGTCATTTGCTGCATGAAGTAATCATAACtcatcttcacactact |
| 10nm4merTip-23 | 341 | TGCAGACCCATAAAGGACGGTGGTtcatcttcacactact |
| 10nm4merTip-24 | 342 | TCAAATAACAGTCCAAGGCGCTTTGCGAGAAAtcatcttcacactact |
| 10nm4merTip-25 | 343 | AAGGATCCGCGGAGCTCAGGTGATtcatcttcacactact |
| 10nm4merTip-26 | 344 | AAACAGGCAAACATCATAGTCGGAACGTCAATAGTCACACCGGCtcatcttcacactact |
| 10nm4merTip-27 | 345 | GTACAGTTAGACAAGCATTACATTTAGTCACCTCACCGAAtcatcttcacactact |
| 10nm4merTip-28 | 346 | ACTATCAAAAAAAATTAACCACCAACCGAAGAtcatcttcacactact |
| 10nm4merTip-29 | 347 | CATCCAAAGGATAGCGGTAAGGGGtcatcttcacactact |
| 10nm4merTip-30 | 348 | AAATAATATAACGCCGAAGATTACCAGCtcatcttcacactact |
| 10nm4merTip-31 | 349 | CAAAACAGAGCAGGAGAAATTTCATGAATGAAtcatcttcacactact |
| 10nm4merTip-32 | 350 | GGCGAATAAGTAAGTCATGATAACtcatcttcacactact |
| 10nm4merTip-33 | 351 | AGGTGATACGCGTTCTGCGGTTCCCTATTCCACTGCAACAATTAtcatcttcacactact |
| 10nm4merTip-34 | 352 | CTTGGGTCGCCAAGGTACTGCGCGGCGGtcatcttcacactact |
| 10nm4merTip-35 | 353 | CTGACAATCTTTGATTAGCGGTTAtcatcttcacactact |
| 10nm4merTip-36 | 354 | AATTTTGAATCGAACAACCTTATCACGAGTCAACCCCTCAtcatcttcacactact |
| 10nm4merTip-37 | 355 | cctacgagtcagtcctGCCACGACCTCATTAGATAACGAGCGCCAGCG |
| 10nm4merTip-38 | 356 | cctacgagtcagtcctAAATGGTAAAGATGGGACGCTCGGCGCC |
| 10nm4merTip-39 | 357 | cctacgagtcagtcctTGGAAAATGTCTGGGATTTTGGGA |
| 10nm4merTip-40 | 358 | cctacgagtcagtcctGACGGAAGATGAGTGACGTCCTTTACCAGCCTCAT |
| 10nm4merTip-41 | 359 | cctacgagtcagtcctTGAAGAAACGTTCTTGGCATAAGCAGCT |
| 10nm4merTip-42 | 360 | cctacgagtcagtcctGCCCTAACGACGTATAAGTCGACC |
| 10nm4merTip-43 | 361 | cctacgagtcagtcctATTAGAAAACACTGTTGAAGCGGCATGGGTGGCAT |
| 10nm4merTip-44 | 362 | cctacgagtcagtcctTCATAGCCTTAGACGATGACCCTCGTCATAAG |
| 10nm4merTip-45 | 363 | cctacgagtcagtcctTCAGTTAAGTGGACGGCAGAACAT |
| 10nm4merTip-46 | 364 | cctacgagtcagtcctACCAAGCACCAAATAGCTGGAGTAACAGTATGGCG |
| 10nm4merTip-47 | 365 | cctacgagtcagtcctTTATTGCCAGTCCTTGCATCATGGCGAC |
| 10nm4merTip-48 | 366 | cctacgagtcagtcctTAATAACCAAATGCAGACGCTCCCCAAACCAT |
| 10nm4merTip-49 | 367 | cctacgagtcagtcctGCTTCGGCGCGTTGACCCAACAGACGAGTGGT |
| 10nm4merTip-50 | 368 | cctacgagtcagtcctTAACCTCAGCGGTAGCTTTATTCG |
| 10nm4merTip-51 | 369 | cctacgagtcagtcctCACTAATCGCGCCCTACCTCTTTAGTCGTAGTGCC |
| 10nm4merTip-52 | 370 | cctacgagtcagtcctACGGTCACACTGAACGCATAATCATGGT |
| 10nm4merTip-53 | 371 | TAGCACCAAGTGCCAGCCTGCAACTATCAGAACTGGAGAC |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 10nm4merTip-54 | 372 | CAGTAGTGATTGGTATCAGGGTTAAATGCTTAACAGTAGA |
| 10nm4merTip-55 | 373 | AAAACGAAAAAGCACCTTTAGCGTAATATCGGTTTGGTCA |
| 10nm4merTip-56 | 374 | CAGCTTATGGTGTCTGTAAAACAGTGACGATGCAAAAATT |
| 10nm4merTip-57 | 375 | TAGCACCAAGTGCCAGCCTGCAACtagctcactcagtctca |
| 10nm4merTip-58 | 376 | TATCAGAACTGGAGAC |
| 10nm4merTip-59 | 377 | CAGTAGTGATTGGTATCAGGGTTAtagctcactcagtctca |
| 10nm4merTip-60 | 378 | AATGOTTAACAGTAGA |
| 10nm4merTip-61 | 379 | AAAACGAAAAAGCACCTTTAGCGTtaacttcctatctcact |
| 10nm4merTip-62 | 380 | AATATCGGTTTGGTCA |
| 10nm4merTip-63 | 381 | CAGCTTATGGTGTCTGTAAAACAGtaacttcctatctcact |
| 10nm4merTip-64 | 382 | TGACGATGCAAAAATT |
| 10nm4mersp-01 | 383 | ACCAGCAGAGGAAGCATCAGCACCA |
| 10nm4mersp-02 | 384 | GTTTTTGAGATGGCAGCAACGGAAA |
| 10nm4mersp-03 | 385 | ACATACGAAGGCGCATAACGATACC |
| 10nm4mersp-04 | 386 | GGGTCGGCATCAAAAGCAATATCAG |
| 10nm4mersp-05 | 387 | GCAAGATAATCACGAGTATCCTTTC |
| 10nm4mersp-06 | 388 | TTAGCCTCGGTACGGTCAGGCATCC |
| 10nm4mersp-07 | 389 | CACCAGAACGGAAAACATCCTTCAT |
| 10nm4mersp-08 | 390 | ATGTATCCATCTGAATGCAATGAAG |
| 20nm3mertip-01 | 391 | GTTGACCACCTACATACCAAATACGCTCCTGA |
| 20nm3mertip-02 | 392 | CGAGAGTCAGGTACGGCGGTCAGTAGTTTGTTACTCGTCAGAAAATCG AA |
| 20nm3mertip-03 | 393 | TGCGCTGGTAATAAGACGACCAGGAATT |
| 20nm3mertip-04 | 394 | GTTAATCGAGCGGCATGGTCAATATTAACACCAAACGTGA |
| 20nm3mertip-05 | 395 | TCTCCTCACTACCATGAACAAAATGTAATCCACGCTCTTT |
| 20nm3mertip-06 | 396 | GGAAGACGGCAGCAATAAACAGTAGTTGAAAGTACA |
| 20nm3mertip-07 | 397 | TAAAAAGTGAGAGCGCGAAGGAGTCAAGGAAG |
| 20nm3mertip-08 | 398 | TAAAATGTCAACAAACCAATCCAAGAGAATCTTCCAAC |
| 20nm3mertip-09 | 399 | ATCATCTTATTAGGGTTAGCCTCGGCATCCACGGCGCTTTGTATCAGG |
| 20nm3mertip-10 | 400 | GCGTCAGCGAAACGCAGTTTTTGACATATCCTACAAAGTCCAAGCA |
| 20nm3mertip-11 | 401 | GTGGAGCTTGCAGACCCATATCGTTCTCTAACCCAG |
| 20nm3mertip-12 | 402 | AGATGAAACCATTTTTGAATCTCTCAGA |
| 20nm3mertip-13 | 403 | CGGTCGTCAGAGTGTCAAAAACGATCATCAAAAGTGGAGG |
| 20nm3mertip-14 | 404 | ATAACTCCAAAGCAGCCTGAAACAAAGTCATTTGGCGAGAAAAGAT |
| 20nm3mertip-15 | 405 | TTGAACACAGAGGGCGCGGCAAAAGTGGTCTA |
| 20nm3mertip-16 | 406 | AGCAGCCTTATGGCCGTCAAGGAGCACATCGG |
| 20nm3mertip-17 | 407 | CAGAAGCCTGAATGAGGGAAACCATAACGAGCATTCAA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nm3mertip-18 | 408 | TTGAGTTGCGTAGCCATGGCAGCAACCTTAATAGAGGCCAAAGCGGTCTG |
| 20nm3mertip-19 | 409 | TTATAGATATCATCTTGATTAAGCGTTAAATCCAAAACGG |
| 20nm3mertip-20 | 410 | GAAACGTATCGGCGTGTGAATCATACCCTCGGCAGCAAGACCTCTAAT |
| 20nm3mertip-21 | 411 | GACTCATGATTTCTTAACCATACTCAGGCACACGAAAA |
| 20nm3mertip-22 | 412 | CCAACTGCGCCGCCAAGGGAAGTACGTG |
| 20nm3mertip-23 | 413 | TAGTCATGGAACCGCACGCAAAGCATGGTCAACGCTACCTGTCGAC |
| 20nm3mertip-24 | 414 | CAATATCACAAAAATACTGATAGCGATTGTTCAGTAACTT |
| 20nm3mertip-25 | 415 | GACTCAGAGACTCATATCTAAACCGAACGTGCCAAGCATAGAAAGGTC |
| 20nm3mertip-26 | 416 | GACAGATTTGTCATTGTGAGTGCGTTCTCTAC |
| 20nm3mertip-27 | 417 | GACCTTTAACTGGCGGCGATTCGTCACAGGTAGCCA |
| 20nm3mertip-28 | 418 | ATCAGAAAATACGCCACGCGCATAACTTTTCC |
| 20nm3mertip-29 | 419 | GACGGTTGACAGTCCCCATTAGCTGTCCTATTAGTGGTTGAACAGCATCG |
| 20nm3mertip-30 | 420 | GCAAAGTAGAGCTGCGCAAGGATACGATTTAATCAAGATA |
| 20nm3mertip-31 | 421 | AAGCATGTCAATGCTCAGTCTCTTTTtcatcttcacactact |
| 20nm3mertip-32 | 422 | TTACCTCCAAATGAAGAATAATTATtcatcttcacactact |
| 20nm3mertip-33 | 423 | GACGGGATACAATTCAGCTCGACGTTTTTGACtcatcttcacactact |
| 20nm3mertip-34 | 424 | GGCGCTGCGTAACCGTCTTCCTCTACGCAATAtcatcttcacactact |
| 20nm3mertip-35 | 425 | TAAGGCCAAAGCGGCTAGGCCACAGCAAGGTCtcatcttcacactact |
| 20nm3mertip-36 | 426 | CAATGGCGCCAGGCAATGGAtcatcttcacactact |
| 20nm3mertip-37 | 427 | CCAGCGCCAGCGATAACCGGATCCACTGCTACtcatcttcacactact |
| 20nm3mertip-38 | 428 | TTAAGCGAGCGCCAGAACGTTTTTTACCGAACGTCACTCAAGTAtcatcttcacactact |
| 20nm3mertip-39 | 429 | ACTCGCGACAGCTTGGTTTTTAGTGAGTTTTAGCCATAACCCAGtcatcttcacactact |
| 20nm3mertip-40 | 430 | TATCGTGTTTCCCGCAAGGTAAACGCGAGAACATAACCATtcatcttcacactact |
| 20nm3mertip-41 | 431 | CTTATCAACAGGGCGTACCAGAGTCAtcatcttcacactact |
| 20nm3mertip-42 | 432 | ACGTTCCAAGAGCTCAAAGAAACGCGGCCATCAACACTCAGTAAtcatcttcacactact |
| 20nm3mertip-43 | 433 | AGTAAATTTGAGCAGATTTGAGTAATTCAGTGtcatcttcacactact |
| 20nm3mertip-44 | 434 | TTAATAATGTTTTCCGTAAAGGCCAtcatcttcacactact |
| 20nm3mertip-45 | 435 | ACTTTCATAGCCAGATTAGAGCGCATGAGCAAATTAAACGtcatcttcacactact |
| 20nm3mertip-46 | 436 | TCGGGCTTCAATAAACTCTGtcatcttcacactact |
| 20nm3mertip-47 | 437 | TTAACGTATGTTCCATCTTTAGCACTTGGTAAGTTGGATTTCGCtcatcttcacactact |
| 20nm3mertip-48 | 438 | GTCAGTTCACAGAATGACACGACCCAGATACAAACTCATCATTAtcatcttcacactact |
| 20nm3mertip-49 | 439 | GCTAAAAATTAGGAGCCTGTCGCATTGCAACCAACCCGATGGGCtcatcttcacactact |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nm3mertip-50 | 440 | GTCAGTAATTTAGACAGCACGTAAAGGGGCCGAAGCCCCTAATTtcatcttcacactact |
| 20nm3mertip-51 | 441 | CAATAGCGAGGGTCCGCCAGCAGTCCACTCGAATTTAGACAGGCtcatcttcacactact |
| 20nm3mertip-52 | 442 | CCCTTTGTAGCAATCGCGAAtcatcttcacactact |
| 20nm3mertip-53 | 443 | AAGCTAGAAGTCGTCGGGAGAGGAGTGGACCAGTAGATGAAGTAtcatcttcacactact |
| 20nm3mertip-54 | 444 | CAGTTGCGTACCAGGAAGTGCTTCTGtcatcttcacactact |
| 20nm3mertip-55 | 445 | AACCAGAACGTGAAAAAGTGGAAGCtcatcttcacactact |
| 20nm3mertip-56 | 446 | GTCAGTATCAAGTAAACATAAGAGAGAAAACTtcatcttcacactact |
| 20nm3mertip-57 | 447 | GTCGCATAGAAATATAACTGGTAGCTTTCGTATTTTGCGAtcatcttcacactaact |
| 20nm3mertip-58 | 448 | cctacgagtcagtcctTGGGGATAACATCATGGTGCAT |
| 20nm3mertip-59 | 449 | cctacgagtcagtcctCCTTTCAACGTGAGCCAGGAGGAAGCGGATGTTT |
| 20nm3mertip-60 | 450 | cctacgagtcagtcctGATAATCTGGTTGAACGGCGAAGC |
| 20nm3mertip-61 | 451 | cctacgagtcagtcctACTCTTGTGCCAATTCATCCACGA |
| 20nm3mertip-62 | 452 | cctacgagtcagtcctAGTATAAAGAAATGCCAACGCAAGCCTCCGAGCA |
| 20nm3mertip-63 | 453 | cctacgagtcagtcctTTAATCCTTCTCAGAGCGCATAAAGTGCAATGAA |
| 20nm3mertip-64 | 454 | cctacgagtcagtcctAAGTTGGGCATACATACAACGCCCTGCATACGAAAAGACACGTC |
| 20nm3mertip-65 | 455 | cctacgagtcagtcctCATGCGGCAGACGAGCTTAGTACCTCGCAACGGCTGCGGACGAC |
| 20nm3mertip-66 | 456 | cctacgagtcagtcctCGACTTTGAATATTAGACATGCAA |
| 20nm3mertip-67 | 457 | cctacgagtcagtcctTCTCTTTTCATTTTCACATTCTGATTCTGAACAGCTTCTTAACG |
| 20nm3mertip-68 | 458 | cctacgagtcagtcctACTGATCAGCATTGGGATTATCATAAAACATACGAC |
| 20nm3mertip-69 | 459 | cctacgagtcagtcctCGTCACGTCCTGCGTGTAGCAA |
| 20nm3mertip-70 | 460 | cctacgagtcagtcctTATCCTTATCATCCTTGATTTCATCGCTGAATAGCA |
| 20nm3mertip-71 | 461 | cctacgagtcagtcctGATGTCTCATTTGAATCGTTAGTTGATGAAGCCACT |
| 20nm3mertip-72 | 462 | cctacgagtcagtcctCAGGTTGGTATCCGAACTGCTTTATTCGTAAACAAG |
| 20nm3mertip-73 | 463 | cctacgagtcagtcctCTGCTGTTAACATGCTTAGGGATTTTATAATAGTTG |
| 20nm3mertip-74 | 464 | cctacgagtcagtcctGAAAGACGAAAAATGTTTCACCATATCCTTCATGAA |
| 20nm3mertip-75 | 465 | cctacgagtcagtcctATAGCAATTCAGCGCCTTTAAG |
| 20nm4mertip-01 | 466 | GTTCAGAAAACTGGCCTAACCACTGCAACAAGAAAA |
| 20nm4mertip-02 | 467 | GCGTCACCTGAAACAATAAGAGGTTTTGAAGAAATAACATCATGGTAACG |
| 20nm4mertip-03 | 468 | AAAGCGGCATAGATATTCAAATAAGTACGGTCAGGCATCC |
| 20nm4mertip-04 | 469 | AGGCGCTGAACGGACTTCATAGAAGCGC |
| 20nm4mertip-05 | 470 | TATAACGTGCTTTAGGTGTCTGTAGAACCAGCAATAAAAG |
| 20nm4mertip-06 | 471 | CTGCATGAATATCAGCACCAACAGATTAGCGGCGTTGACATATCAAAA |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nm4mertip-07 | 472 | ACGGCGCTTTACCAAATACCTAAATAGTTGTTATGGTC |
| 20nm4mertip-08 | 473 | TTAAACTCAAAATTTTACATTAAAATCATGGT |
| 20nm4mertip-09 | 474 | AATATGACGGTAAAGAACCAGTAGTGTCATAGCCAGATGCCCGTCA |
| 20nm4mertip-10 | 475 | ATAACGATACCACTGACCCTAATCACCATGGT |
| 20nm4mertip-11 | 476 | AGAAAAACCGGTCGGACCACCATTACCATCCAAAGGATAAACCCAC |
| 20nm4mertip-12 | 477 | TCTGAATGGGGTCGGCATCAAAAGTAATCACGTTCTTGGT |
| 20nm4mertip-13 | 478 | ACCAAAAACCATTTTTGAATCTCTCAGA |
| 20nm4mertip-14 | 479 | CAGCAAGACAATATCACGAAAATATAATCGGTAACCAACC |
| 20nm4mertip-15 | 480 | CAGTATGCAAATTAGCACAGGCAAAAAATTTACAATGA |
| 20nm4mertip-16 | 481 | CATCACACAGTCCTTGACGGTCGTTCTCTAATCCGC |
| 20nm4mertip-17 | 482 | CTGTCGCACCTCCAGCCGGCAAAAGTGGTCTA |
| 20nm4mertip-18 | 483 | ACTCAGAAGAGAAATAAGCGAACCAAATAAGCAGCTTGCAGACCCATA AT |
| 20nm4mertip-19 | 484 | AGCAGCCTTATGGCCGTCAAGGAGCACATCGG |
| 20nm4mertip-20 | 485 | GTCAATAGTAAAGTGCACCGCATGCGGCCATTAGCTGTACACCCTCGG |
| 20nm4mertip-21 | 486 | TACCCTTGAAAGTGGGACGACCAAAAAGTCTCAGGAGGAAGCGGAGC AGT |
| 20nm4mertip-22 | 487 | TGCGGTGAAAAAGCGTCCTGAGCGCGCATAAACGTA |
| 20nm4mertip-23 | 488 | CACACAAACTGTAGGAAGTGTCCGGTGGTAGAAGTCGTCA |
| 20nm4mertip-24 | 489 | GATAGGTCGTAGTAATGGATACGCGCGCCGCC |
| 20nm4mertip-25 | 490 | GATAGCGGCGACTGGCAGTCGGCGTGACTGTAACCATAAGGCGAAC |
| 20nm4mertip-26 | 491 | TCTAAACCGAACGTGCCAAGCATAGACAGAATAGCTTCTC |
| 20nm4mertip-27 | 492 | TGGTAAGTTGGATTAAGCACCCCAGCCTCACA |
| 20nm4mertip-28 | 493 | TTTGGCGAGAAAGCTCTTAGGGTCAACGCTACAATACT |
| 20nm4mertip-29 | 494 | TGTTAATTTGAGCAGACTCATTCTAGCT |
| 20nm4mertip-30 | 495 | CCAAATGTTGATTTCTTACCTATTCAGCATCGGACTCAGAGACTCATA |
| 20nm4mertip-31 | 496 | GTTAGCCTCTGAAACAAATGCTTATGGTATCAGGGTTAATGTGGCATT |
| 20nm4mertip-32 | 497 | GTCAAATGAGCCTGACAAGAGAATCTATCGAAATCATCTTCGTGTT |
| 20nm4mertip-33 | 498 | TTTCTTCTGCGTCAGTAAGAACCAGGGCCTTT |
| 20nm4mertip-34 | 499 | GGAAACCATAACGAGCTGGAAACGTACGGATTTAAAAT |
| 20nm4mertip-35 | 500 | ACGGCGTCACCAATCTGCCGAAGCTTGCCTTT |
| 20nm4mertip-36 | 501 | CGCTCTTTGTTCAGTAACTTGACTTTGAGATGGCAGCAAC |
| 20nm4mertip-37 | 502 | AGAGGTTTATGGGATCCAAAGCGGTCATCATCTTGATTAAGCTCATTAG G |
| 20nm4mertip-38 | 503 | AACACCATCTTAATCCACTGTTCAATGTCTACGAGAAAGA |
| 20nm4mertip-39 | 504 | CGGCAACATACCAAAGGCGGCTTTACGT |
| 20nm4mertip-40 | 505 | ACTCAGCGGTCAGTAGCAATGTTGACCACCTGCAAT |
| 20nm4mertip-41 | 506 | CAGCAAGGTAGCGACAGTTGTTCCTTGAACGGCGTCGCGTCTGC |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nm4mertip-42 | 507 | AGCACCAAACTTGTTAAATCCCAGCG |
| 20nm4mertip-43 | 508 | GTACTGAATACAAAACTCGGTATAGATAAGCAGGAGAAACAAGC |
| 20nm4mertip-44 | 509 | CAACAGGCGCGAATATCTTTTTGGATTCTTTA |
| 20nm4mertip-45 | 510 | GCGCGAGCGCCAAAATGGTA |
| 20nm4mertip-46 | 511 | TCTTTAATCCAGCAATCACCTCACCAGATACAAACTCATCATTA |
| 20nm4mertip-47 | 512 | GAACATGGGCATATTATCATAAAACGCCCACGCAAAAAGCGGCT |
| 20nm4mertip-48 | 513 | GAAGATTTCACGCGGCGGCAAGTTGCCATCTCTTTAAAGAAGGTCAT |
| 20nm4mertip-49 | 514 | GTACGGGGTGAATCGCAATCTTTTTTAAGTGG |
| 20nm4mertip-50 | 515 | AAGTGACGTTTGAGAGATTACCGCGC |
| 20nm4mertip-51 | 516 | ACGAAGTAGCGGTAAAGTAGCCTCT |
| 20nm4mertip-52 | 517 | CTTCGTCGCAGTCGAACAAGCGGCGCCATCTGTTGACAGG |
| 20nm4mertip-53 | 518 | TTTATAGGGTTTGAATTCATGCGGAGTCAAAG |
| 20nm4mertip-54 | 519 | AGTCATGGCGACCTGGAGTAACAGAAGTACAGGTGCCATAAACA |
| 20nm4mertip-55 | 520 | ACACGAAGGCGGCTCAGCGG |
| 20nm4mertip-56 | 521 | TCCGACAGGAGCAGGAAACGGAGTA |
| 20nm4mertip-57 | 522 | ACTTTCAGCGAAGGCATTTAGTCATGATAAGGACGTGAAA |
| 20nm4mertip-58 | 523 | TTCATGACTTTTTTTAGCCATACTCATCCACAACCAGTAG |
| 20nm4mertip-59 | 524 | CGGGATGAAATGTTTTTTCCATGACCTTCTGCACGTAATTTAGA |
| 20nm4mertip-60 | 525 | GCGACGTGTAGCCACGTATTCGCCAG |
| 20nm4mertip-61 | 526 | GGTTCAATCATTTTTATCGAAAGGTCGCTCAT |
| 20nm4mertip-62 | 527 | ACGCTCGCAAGAGTAAACTTGGTCA |
| 20nm4mertip-63 | 528 | AATTACATAGAAACCAACCACTTCG |
| 20nm4mertip-64 | 529 | GACCCATCAACAGGGACATAAAAAGTAAATAAACGTAAGAAACG |
| 20nm4mertip-65 | 530 | ACGCAACCGGACGCTCGACGCCATTAATACATAATAACATCACTATA |
| 20nm4mertip-66 | 531 | CCTCAACGACTTCTGCCATCAGAATGAGACAG |
| 20nm4mertip-67 | 532 | CGAGGTCAGAAATCCAACGCGTCAGTTTAAGCCACTCAGCGTAC |
| 20nm4mertip-68 | 533 | TGAGTATAATAAATCATAGGCTGAAT |
| 20nm4mertip-69 | 534 | ACCCGATTCTGAACAGCTTCTTGGGAAGTCCATATCATATCTGGGGT |
| 20nm4mertip-70 | 535 | CATTAGCAATGAAAACTCAAAAGTGTTACAGCGACGACAA |
| 20nm4mertip-71 | 536 | CCCTTTGTAGCAGATTTCAT |
| 20nm4mertip-72 | 537 | TCGTCAATCTCAAATTCGTA |
| 20nm4mertip-73 | 538 | GGCGCTGCGTAACCGTCTTCAGTGTCAAATCA |
| 20nm4mertip-74 | 539 | ACGTTCCAAGAGCTCAGAAGCAATACCGAACCTGATCTCAGTAAATC |
| 20nm4mertip-75 | 540 | CATATTTAACCTGACTATTCTTGAATTAAAAA |
| 20nm4mertip-76 | 541 | ACGCCCCTGCAATTAAAATTAGGCCACGAGGA |
| 20nm4mertip-77 | 542 | ACCCTTCCTGAATGAATGGGATAC |

TABLE 4-continued

Staple strands for nucleic acid polygonal nanopore: Staple sequences for the polygonal frames (folded with M13 scaffold) and other nanopores (folded with PhiX174 scaffold).

| Name | SEQ ID NO. | Sequence |
|---|---|---|
| 20nm4mertip-78 | 543 | ACGCTTGTGCCAATTCATCCACGA |
| 20nm4mertip-79 | 544 | CAGTCAGCCATATAACTGACCA |
| 20nm4mertip-80 | 545 | AGTGGAGGTTGCATTCAAACGATACGTCAGCCAACG |
| 20nm4mertip-81 | 546 | AGCAATAGACCAAACCATCAAT |
| 20nm4mertip-82 | 547 | TTCGCATAGTGCCATGCTACAC |
| 20nm4mertip-83 | 548 | GTCGCAAATGAACCTTCAACGGCAGAAGCTTAAT |
| 20nm4mertip-84 | 549 | AACGCAGACGACACCATTCGGGAGGGTAAAGAAG |
| 20nm4mertip-85 | 550 | AACAAGCAGAATTTTCAAAGTAAGCGTTAGTTGATG |
| 20nm4mertip-86 | 551 | AAGTTGGGCATACATACAACGCCCTGCATACGAAAAGACACGTC |
| 20nm4mertip-87 | 552 | TTTCTTGTTGACAGTCCCAAGCTATTTAATTGCG |
| 20nm4mertip-88 | 553 | CAAAAATTCTAAGCAGTGGCGAGATTATCAGAAAAA |
| 20nm4mertip-89 | 554 | TTCTTGCACAGCAATCAATCACCAGAACGGAAAACATCCTGGAA |
| 20nm4mertip-90 | 555 | CCTAGAGATGTATGACGCGCATGACAAGTTGTCA |
| 20nm4mertip-91 | 556 | CCAACGAAGAAGCAGCATTAACCGTCAATGTATCCA |
| 20nm4mertip-92 | 557 | CTTTGCATTGGGTGAATCATTAGCCTTGTACTCAGG |
| 20nm4mertip-93 | 558 | AGTCTCTCCTCACTACCATGAACAAAATGTAATCCA |
| 20nm4mertip-94 | 559 | ATTTTCTCTCTTTTTGCGTTCGTA |
| 20nm4mertip-95 | 560 | ATAAGACGCATCTCGAACGCAATGAGTAGAGTCAAT |
| 20nm4mertip-96 | 561 | TAACTTTTTCCGTGGAAGCATTTTCATCCCGAAGTTGCGGTTTG |
| 20nm4mertip-97 | 562 | TGCGGACGACGTCAGTCGCAAGGTAAACGCGAACAATTCAACGA |
| 20nm4mertip-98 | 563 | GTTGGAACGTTTTTTACCTTTTTG |
| 20nm4mertip-99 | 564 | ATAACGCGAGGGTATCCTAGCA |
| 20nm4mertip-100 | 565 | AACAGACGATGATTAACAGTCGGGAGAGTGCCAAGA |
| 20nm4mersp-01 | 566 | CCGCTTCGGCGTTATAACCTCACAC |
| 20nm4mersp-02 | 567 | CATGGAAGCGATAAAACTCTGCAGG |
| 20nm4mersp-03 | 568 | TCTTGAACACTCATCCTTAATACCT |
| 20nm4mersp-04 | 569 | CTGCTTTATCAAGATAATTTTTCGA |
| 20nm4mersp-05 | 570 | TTAAGAGGGCGTTCAGCAGCCAGCT |
| 20nm4mersp-06 | 571 | TAGACATAATTTATCCTCAAGTAAG |
| 20nm4mersp-07 | 572 | GTGGTCGGCAGATTGCGATAAACGG |
| 20nm4mersp-08 | 573 | CCAGCAAGGAAGCCAAGATGGGAAA |

TABLE 5

| Cholesterol-modified strands for nucleic acid polygonal nanopore: | | |
|---|---|---|
| Chl-1 | SEQ ID NO: 574 | GGACTGACTCGTAGG-chl |
| Chl-2 | SEQ ID NO: 575 | chl-AGTAGTGTGAAGATG |

chl—cholesterol tags

Example 6

Assembly and Membrane Insertion of Nucleic Acid Planar Ring Nanopore

The modules were individually prepared via the scaffold-and-staple approach. The design approach was validated by first preparing the surface portion of the polygonal frame (without the perpendicular channel forming tail). The DNA nanostructures were assembled by annealing and cooling.

To obtain membrane pores, the frames were equipped at their bottom with a membrane-spanning partial channel wall, as exemplified with a square pore (FIGS. 9A-9C). The channel wall has the same length as the frame and is composed of a vertical stack of single duplexed DNA duplexes (FIG. 9A). To facilitate the membrane-puncturing of the pores, the frame was also equipped with cholesterol anchors at the bottom of the frame (FIG. 9B). The high membrane affinity of the cholesterol anchors is designed to drive the tip through the membrane (FIG. 9C).

To fold the DNA origami structures, the M13 or PHIX174 (ΦX174) scaffold (Table 3) and 10× excess of corresponding staples (Table 4) were mixed with the 10× folding buffer to a final concentration of 0.5× TAE pH 8.3 supplemented with 16 mM $MgCl_2$. The solutions were then heated at 75° C. for 10 min to denature undesired DNA secondary structures and annealed slowly from 65° C. to 25° C. (1 h per ° C.), cooled down to 10° C. (5 min per ° C.) and kept at 4° C. until collection. After the folding process, the DNA origami structures were purified by excision from 1% agarose gel in 0.5× TBE buffer with 11 mM $MgCl_2$. Cholesterol-DNA strands (Table 5) were added to the DNA pores at a stoichiometry of 1.5 relative to the number of DNA cholesterol attachment sites prior to use in membrane binding and current recordings experiments.

Example 7

TEM Characterization of DNA Origami Pores

DNA nanopores in accordance with an embodiment of the invention were homogenously assembled as shown by single bands in gel electrophoresis as exemplified for square 10 nm pore (FIG. 9D). The designed dimensions and shapes of the polygonal DNA frames were confirmed with transmission electron microscopy and negative staining (FIG. 8).

The pore design was tested with 10 and 20 nm square of blocks featuring bundles of 5× duplexes, and a square tip 4 duplexes deep (FIG. 9A-9C). Each block featured 10 cholesterols for the 10 nm square pore and 15 cholesterols for the 20 nm square pore. The formation of 10 nm square nanopore variant free of cholesterol was confirmed by gel electrophoresis (FIG. 9D). A single band was found implying homogenous assembly. Additional analysis by TEM confirmed the dimensions and geometric shape of the 20 nm square pore (FIG. 9G).

TEM Characterisation was Conducted According to the Following Procedure:

6 μL of the purified DNA pores lacking cholesterol was added onto glow discharge-treated TEM grids (Agar Scientific) and stained with 2% uranyl formate solution. TEM analysis was performed on a JEM-2100 electron microscope (JEOL) operated at 200 kV, and the images were acquired with an Orius SC200 camera. Pores carrying cholesterol tags were incubated with POPC SUVs in 0.5× TAE supplemented with 500 mM NaCl for 20 min, followed by deposition onto EM grids, drying, negative staining, and TEM analysis. The preparation of SUVs involved drying a POPC solution (20 mg/mL 50 μL, in chloroform) in a 2 mL glass vial by argon airflow, resuspension of the dried film with 1× incubation buffer (0.5× TAE with 500 mM NaCl to 1 mL) and sonication for 30 min.

Example 8

Microscopic Analysis of DNA Pore Binding to GUVs

Membrane binding was validated using pores carrying cholesterols as prepared above. In the assay pores were incubated with small unilamellar vesicles (SUVs). Binding was indicated by an upshift of the of DNA pore's gel electrophoretic band (FIG. 9D) because SUVs are too large to enter the gel meshwork. The smeary pore band in the absence of SUVs (FIG. 9D) may indicate non-specific interaction of some pores by the hydrophobic lipidated faces. Pore binding to SUVs was directly visualized with TEM (FIG. 9H, 20 nm pore). To probe the extent of membrane binding, fluorescence microscopy was used. Pores carrying an Atto647N fluorophore were incubated with giant unilamellar vesicles (GUVs) tagged with Bodipy. Fluorescence microscopy images of GUVs yielded a homogenous fluorescence distribution of both signals suggesting that the pores bound well to membranes (FIG. 9G-9H).

Giant unilamellar vesicles (GUVs) composed of POPC phospholipid were prepared via electroformation. Briefly, two droplets of POPC solution (10 mg/mL in chloroform, 3 μL each) were added onto one ITO glass slide. Evaporation of the solvent in air for 5 min led to the formation of patches of dried lipid film. The glass slide was placed into a Vesicle Prep device (Nanion). The lipid film patches were confined by two O-rings, sucrose solution (1 M in water, 600 μL) was added, and another ITO glass slide was placed on top to form a sealed chamber. An alternating electric field was applied across the two slides (3 V, at 5 Hz) for 120 min, and the solution of vesicles was collected afterwards and stored at 4° C.. For DNA pore binding and visualization, 20 μL of 10 nm-wide square pore (~20 nM) was incubated with 500 μL POPC GUVs solution (fluorescence-labeled with 0.5% β-BODIPY 500/510 C12-HPC, D3793, ThermoFisher) in 1× incubation buffer 50 mM HEPES pH 7.6, 300 mM NaCl for 30 min, and the incubated samples were then imaged with an inverted confocal microscope (SPEinv, Leica).

Example 9

Nanopore Recordings

Figure 10:
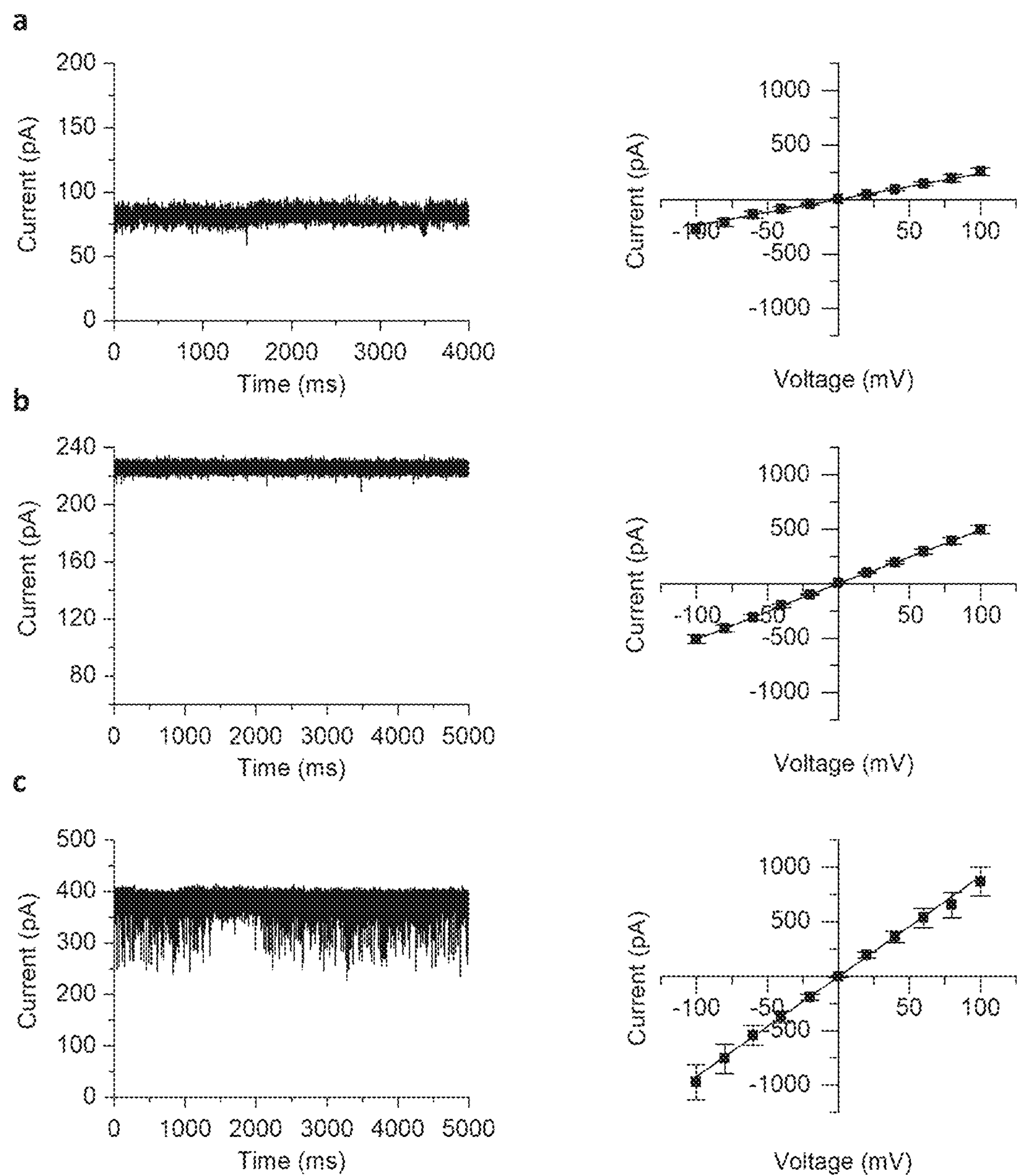
FIG. 10 shows a comparison of single-channel current recordings of different polygonal DNA nanopores inserted into planar lipid bilayers. Example trace and IV curve of A—10 nm×10 nm triangle DNA nanopore, B—10 nm×10 nm square DNA nanopore and C—20 nm×20 nm square DNA nanopore. Experiments were carried out using membranes formed of DPhPC, and electrophysiological buffers composed of 1 M KCl, 10 mM HEPES pH 8.

To show that DNA pores puncture the lipid bilayer with a water-filled hole, single-channel current recordings were used. Traces and IV curve of 10 nm triangle DNA nanopore, 10 nm×10 nm square DNA nanopore, 20 nm×20 nm square DNA nanopore are shown in FIG. 10. The conductance of 80 pA, 232 pA and 395 pA are in agreement with the calculated cross-sectional pore area values of 43 nm$^2$, 100 nm$^2$, and 400 nm$^2$.

For planar lipid bilayer electrophysiological current measurements, integrated chip-based, parallel bilayer recording setups (Orbit 16 and Orbit Mini, Nanion Technologies, Munich, Germany) with multielectrode-cavity-array (MECA) chips (IONERA, Freiburg, Germany) were used. Bilayers were formed by painting of DPhPC dissolved in octane (10 mg mL$^{-1}$). The electrolyte solution was 1 M KCl and 10 mM HEPES, pH 8.0. For pore insertion, a 2:1 mixture of cholesterol-anchored DNA nanopores and 0.5% OPOE (n-octyloligooxyethylene, in 1 M KCl, 10 mM HEPES, pH 8.0) was added to the cis side of the bilayer. Successful incorporation was observed by detecting current steps. The Orbit 16 current traces were Bessel-filtered at 2.873 kHz and acquired at 10 kHz with an EPC-10 patch-clamp amplifier (HEKA Elektronik, Lambrecht/Pfalz, Germany) applying the PATCHMASTER software (HEKA Elektronik). The Orbit Mini current traces were not Bessel-filtered and acquired at 10 kHz, using Element Data Recorder software (Element s.r.I., Italy). Single-channel analysis was performed using Clampfit (Molecular Devices, Sunnyvale, CA, USA).

The nanopore structures of the present invention provided the following advantages:

1) Large Lumen.

It allows the passage of bigger analytes like proteins, while the existing origami pores only have smaller width.

2) Efficient Use of Materials.

For a conventional origami pore, it usually consumes hundreds of staples (~8000 bp), while in this design, only ten strands (300 bp) were needed to form the structure.

3) Simple and Fast Preparation Conditions.

For a conventional origami pore, it takes several days to fold the origami structure, while folding was shortened to 2 hours in this design.

4) Easy and Precise Functionalization.

The well-defined formation of the pore structure conferred upon it atom-level accuracy, this allows for further engineering to acquire a wide range of functionalities.

Although particular embodiments of the invention have been disclosed herein in detail, this has been done by way of example and for the purposes of illustration only. The aforementioned embodiments are not intended to be limiting with respect to the scope of the appended claims, which follow. The choice of nucleic acid sequence(s) is believed to be a routine matter for the person of skill in the art with knowledge of the presently described embodiments. It is contemplated by the inventors that various substitutions, alterations, and modifications may be made to the invention without departing from the spirit and scope of the invention as defined by the claims.

The invention claimed is:

1. A membrane-spanning nanopore, the nanopore comprising:

a) one or more polynucleotide strands that provide a scaffold component; and b) a plurality of polynucleotide strands that provide a plurality of staple components;

wherein each of the plurality of staple components hybridise to the scaffold component;

wherein the orientation of a major portion of at least one polynucleotide strand comprised within the scaffold component is substantially parallel to a planar surface of a membrane as well as embedded within and substantially coplanar with the membrane;

wherein the nanopore defines a channel that is suitable for perforating the membrane;

the channel having a longitudinal axis extending along the centre thereof and a minimum internal dimension perpendicular to the longitudinal axis of at least about 3 nm.

2. The membrane-spanning nanopore of claim 1, wherein either or both of the one or more polynucleotide strands that provide a scaffold component and at least one of the plurality of staple components further comprise at least one hydrophobic anchor that facilitates insertion of the nanopore into the membrane.

3. The membrane-spanning nanopore of claim 1, wherein the channel has a shape perpendicular to the longitudinal axis selected from the group consisting of: annular; elliptical; and polygonal.

4. The membrane-spanning nanopore of claim 1, wherein the nanopore comprises one or more modules.

5. The membrane-spanning nanopore of claim 4, wherein the nanopore further comprises at least one sub-module connected between the one or more modules.

6. The membrane-spanning nanopore of claim 5, wherein the or each module are the same such that the nanopore has rotational symmetry about the longitudinal axis of the channel.

7. The membrane-spanning nanopore of claim 4, wherein the or each module is connected to at least one other module.

8. The membrane-spanning nanopore of claim 7, wherein the connection between modules is provided by structures selected from the group consisting of: a staple strand or portion thereof of one of the modules; a scaffold strand or portion thereof of one of the modules; and one or more polynucleotide strands that provide a spacer component.

9. The membrane-spanning nanopore of claim 1, wherein at least one polynucleotide strand comprised within the scaffold component, the plurality of staple components, and/or the spacer component, when present, comprises DNA.

10. The membrane-spanning nanopore of claim 1, wherein assembly of the nanopore and/or components thereof is via DNA origami techniques.

11. The membrane-spanning nanopore of claim 2, wherein the at least one hydrophobic anchor is comprised of a hydrophobic portion of a polynucleotide strand comprised within the scaffold component.

12. The membrane-spanning nanopore of claim 2, wherein the at least one hydrophobic anchor is comprised of at least one of the plurality of staple components or a hydrophobic portion thereof.

13. The membrane-spanning nanopore of claim 2, wherein the at least one hydrophobic anchor comprises a plurality of hydrophobic anchor molecules.

14. The membrane-spanning nanopore of claim 13, wherein the plurality of hydrophobic anchor molecules are:

a) attached to and spaced substantially equidistantly about the periphery of the nanopore, and wherein the plurality of hydrophobic anchor molecules are orientated radially outwardly from the longitudinal axis of the channel of the nanopore; and/or b) attached to a membrane-facing side of the nanopore or a portion thereof such that the plurality of hydrophobic anchor molecules are orientated to interact with and/or extend into the membrane once inserted.

15. The membrane-spanning nanopore of claim 2, wherein the at least one hydrophobic anchor molecule is selected from the group consisting of: a lipid; and a porphyrin.

16. The membrane-spanning nanopore of claim 15, wherein the lipid is selected from the group consisting of: sterols; alkylated phenols; flavones; saturated and unsaturated fatty acids; and synthetic lipid molecules.

17. The membrane-spanning nanopore of claim 1, wherein the nanopore is in the form of a polygon selected from the group consisting of: a triangle; a square; a quadrilateral; a pentagon; a hexagon; a heptagon; and an octagon.

18. The membrane-spanning nanopore of claim 1, wherein the minimum internal width of the channel of the nanopore is less than about 20 nm.

19. The membrane-spanning nanopore of claim 1, wherein the scaffold component comprises a polynucleotide having a sequence selected from the group consisting of: SEQ ID NO: 1; SEQ ID NO: 2; SEQ ID NO: 13 and SEQ ID NO: 14.

20. The membrane-spanning nanopore of claim 1, wherein the plurality of staple components comprise at least one polynucleotide having a sequence selected from one or more of the group consisting of: SEQ ID NOs: 3 to 12; SEQ ID NOs: 15 to 56; SEQ ID NOs: 65 to 94; SEQ ID NOs: 105 to 140; and SEQ ID NOs: 153 to 268.

21. A membrane into which is inserted at least one membrane-spanning nanopore as described in claim 1.

22. The membrane-spanning nanopore of claim 16, wherein the synthetic lipid molecule is dodecyl-beta-D-glucoside.

23. The membrane-spanning nanopore of claim 1, wherein the scaffold component comprises a plurality of scaffold components comprising polynucleotides having the sequences of each of SEQ ID NOs: 1 and 2 and the plurality of staple components comprise polynucleotides having the sequences of each of SEQ ID NOs: 4-12.

24. The membrane-spanning nanopore of claim 1, wherein the scaffold component comprises polynucleotide having the sequence of SEQ ID NO: 13 and the plurality of staple components comprise polynucleotides having the sequences of one or more of SEQ ID NOs: 15-56, 65-94, 105-140, and 153-268.

25. The membrane-spanning nanopore of claim 1, wherein the scaffold component comprises a polynucleotide having the sequence of SEQ ID NOs: 14 and the plurality of staple components comprise polynucleotides having the sequences of one or more of SEQ ID NOs: 15-56, 65-94, 105-140, and 153-268.

* * * * *

SEQUENCE LISTING

```
<160> NUMBER OF SEQ ID NOS: 575

<210> SEQ ID NO 1
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

tgatagacgg tttttcgccc tttgacgttg gagtccacgt tctttaatag tggactcttg     60

ttccaaactg gaacaacact caaccctatc tcgggctatt cttttgattt ataagggatt    120

ttgccgattt cggaaccacc atcaaacagg attttcgcct g                        161


<210> SEQ ID NO 2
<211> LENGTH: 127
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

ctggggcaaa ccagcgtgga ccgcttgctg caactctctc agggccaggc ggtgaagggc     60

aatcagctgt tgcccgtctc actggtgaaa agaaaaacca ccctggcgcc caatacgcaa    120

accgcct                                                              127


<210> SEQ ID NO 3
<211> LENGTH: 25
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic oligonucleotide"

<400> SEQUENCE: 3
ggtttgcccc agcaggcgaa aatcc 25

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
caccagtgag acggattg 18

<210> SEQ ID NO 5
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
agtccactat taaatcca 18

<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
atcctgtttg atggatcg 18

<210> SEQ ID NO 7
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
gcaaaaatca aaagaattgc ccgagatagg gggcgacaaa gttgagt 47

<210> SEQ ID NO 8
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
acgtaaaacc gtctatttag gcggtttgcg tgcctgtcac cattggg 47

<210> SEQ ID NO 9

<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
ccctgccctg agagagttgc agcaagcggt ccttataatc ccacgct 47

<210> SEQ ID NO 10
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
cgccagggtt ttggacgaac gttttggttt ttctttt 37

<210> SEQ ID NO 11
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
gttgttcctt tccgaatggt ttttagtttg gaacaag 37

<210> SEQ ID NO 12
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
ggtttgcctt tagctggcaa ctttccagca ggcgaaa 37

<210> SEQ ID NO 13
<211> LENGTH: 7249
<212> TYPE: DNA
<213> ORGANISM: M13 bacteriophage

<400> SEQUENCE: 13
aatgctacta ctattagtag aattgatgcc accttttcag ctcgcgcccc aaatgaaaat 60
atagctaaac aggttattga ccatttgcga aatgtatcta atggtcaaac taaatctact 120
cgttcgcaga attgggaatc aactgttata tggaatgaaa cttccagaca ccgtacttta 180
gttgcatatt taaaacatgt tgagctacag cattatattc agcaattaag ctctaagcca 240
tccgcaaaaa tgacctctta tcaaaaggag caattaaagg tactctctaa tcctgacctg 300
ttggagtttg cttccggtct ggttcgcttt gaagctcgaa ttaaaacgcg atatttgaag 360
tctttcgggc ttcctcttaa tctttttgat gcaatccgct ttgcttctga ctataatagt 420
cagggtaaag acctgatttt tgatttatgg tcattctcgt tttctgaact gtttaaagca 480
tttgaggggg attcaatgaa tatttatgac gattccgcag tattggacgc tatccagtct 540

```
aaacatttta ctattacccc ctctggcaaa acttcttttg caaaagcctc tcgctatttt    600

ggtttttatc gtcgtctggt aaacgagggt tatgatagtg ttgctcttac tatgcctcgt    660

aattcctttt ggcgttatgt atctgcatta gttgaatgtg gtattcctaa atctcaactg    720

atgaatcttt ctacctgtaa taatgttgtt ccgttagttc gttttattaa cgtagatttt    780

tcttcccaac gtcctgactg gtataatgag ccagttctta aaatcgcata aggtaattca    840

caatgattaa agttgaaatt aaaccatctc aagcccaatt tactactcgt tctggtgttt    900

ctcgtcaggg caagccttat tcactgaatg agcagctttg ttacgttgat ttgggtaatg    960

aatatccggt tcttgtcaag attactcttg atgaaggtca gccagcctat gcgcctggtc   1020

tgtacaccgt tcatctgtcc tctttcaaag ttggtcagtt cggttccctt atgattgacc   1080

gtctgcgcct cgttccggct aagtaacatg gagcaggtcg cggatttcga cacaatttat   1140

caggcgatga tacaaatctc cgttgtactt tgtttcgcgc ttggtataat cgctgggggt   1200

caaagatgag tgttttagtg tattcttttg cctctttcgt tttaggttgg tgccttcgta   1260

gtggcattac gtattttacc cgtttaatgg aaacttcctc atgaaaaagt ctttagtcct   1320

caaagcctct gtagccgttg ctaccctcgt tccgatgctg tctttcgctg ctgagggtga   1380

cgatcccgca aaagcggcct ttaactccct gcaagcctca gcgaccgaat atatcggtta   1440

tgcgtgggcg atggttgttg tcattgtcgg cgcaactatc ggtatcaagc tgtttaagaa   1500

attcacctcg aaagcaagct gataaaccga tacaattaaa ggctcctttt ggagcctttt   1560

ttttggagat tttcaacgtg aaaaaattat tattcgcaat tcctttagtt gttcctttct   1620

attctcactc cgctgaaact gttgaaagtt gtttagcaaa atcccataca gaaaattcat   1680

ttactaacgt ctggaaagac gacaaaactt tagatcgtta cgctaactat gagggctgtc   1740

tgtggaatgc tacaggcgtt gtagtttgta ctggtgacga aactcagtgt tacggtacat   1800

gggttcctat tgggcttgct atccctgaaa atgagggtgg tggctctgag ggtggcggtt   1860

ctgagggtgg cggttctgag ggtggcggta ctaaacctcc tgagtacggt gatacaccta   1920

ttccgggcta tacttatatc aaccctctcg acggcactta tccgcctggt actgagcaaa   1980

accccgctaa tcctaatcct tctcttgagg agtctcagcc tcttaatact ttcatgtttc   2040

agaataatag gttccgaaat aggcaggggg cattaactgt ttatacgggc actgttactc   2100

aaggcactga ccccgttaaa acttattacc agtacactcc tgtatcatca aaagccatgt   2160

atgacgctta ctggaacggt aaattcagag actgcgcttt ccattctggc tttaatgagg   2220

atttatttgt ttgtgaatat caaggccaat cgtctgacct gcctcaacct cctgtcaatg   2280

ctggcggcgg ctctggtggt ggttctggtg gcggctctga gggtggtggc tctgagggtg   2340

gcggttctga gggtggcggc tctgagggag gcggttccgg tggtggctct ggttccggtg   2400

attttgatta tgaaaagatg gcaaacgcta ataagggggc tatgaccgaa aatgccgatg   2460

aaaacgcgct acagtctgac gctaaaggca aacttgattc tgtcgctact gattacggtg   2520

ctgctatcga tggtttcatt ggtgacgttt ccggccttgc taatggtaat ggtgctactg   2580

gtgattttgc tggctctaat tcccaaatgg ctcaagtcgg tgacggtgat aattcacctt   2640

taatgaataa tttccgtcaa tatttacctt ccctccctca atcggttgaa tgtcgccctt   2700

ttgtctttgg cgctggtaaa ccatatgaat tttctattga ttgtgacaaa ataaacttat   2760

tccgtggtgt ctttgcgttt cttttatatg ttgccacctt tatgtatgta ttttctacgt   2820

ttgctaacat actgcgtaat aaggagtctt aatcatgcca gttcttttgg gtattccgtt   2880
```

```
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcatttttga cgttaaacaa aaaatcgttt cttatttgga   3180
ttgggataaa taatatggct gtttattttg taactggcaa attaggctct ggaaagacgc   3240
tcgttagcgt tggtaagatt caggataaaa ttgtagctgg gtgcaaaata gcaactaatc   3300
ttgatttaag gcttcaaaac ctcccgcaag tcgggaggtt cgctaaaacg cctcgcgttc   3360
ttagaatacc ggataagcct tctatatctg atttgcttgc tattgggcgc ggtaatgatt   3420
cctacgatga aaataaaaac ggcttgcttg ttctcgatga gtgcggtact tggtttaata   3480
cccgttcttg gaatgataag gaaagacagc cgattattga ttggtttcta catgctcgta   3540
aattaggatg ggatattatt tttcttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt taaatatggc gattctcaat taagccctac tgttgagcgt tggctttata   3780
ctggtaagaa tttgtataac gcatatgata ctaaacaggc tttttctagt aattatgatt   3840
ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catatagtta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta aatgtaatta attttgtttt cttgatgttt   4260
gtttcatcat cttcttttgc tcaggtaatt gaaatgaata attcgcctct gcgcgatttt   4320
gtaacttggt attcaaagca atcaggcgaa tccgttattg tttctcccga tgtaaaaggt   4380
actgttactg tatattcatc tgacgttaaa cctgaaaatc tacgcaattt ctttatttct   4440
gttttacgtg caaataattt tgatatggta ggttctaacc cttccattat tcagaagtat   4500
aatccaaaca atcaggatta tattgatgaa ttgccatcat ctgataatca ggaatatgat   4560
gataattccg ctccttctgg tggtttcttt gttccgcaaa atgataatgt tactcaaact   4620
tttaaaatta ataacgttcg ggcaaaggat ttaatacgag ttgtcgaatt gtttgtaaag   4680
tctaatactt ctaaatcctc aaatgtatta tctattgacg gctctaatct attagttgtt   4740
agtgctccta aagatatttt agataacctt cctcaattcc tttcaactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aaatattgtc tgtgccacgt   5040
attcttacgc tttcaggtca gaagggttct atctctgttg gccagaatgt cccttttatt   5100
actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
```

```
actaatcaaa gaagtattgc tacaacggtt aatttgcgtg atggacagac tcttttactc   5340
ggtggcctca ctgattataa aaacacttct caggattctg gcgtaccgtt cctgtctaaa   5400
atccctttaa tcggcctcct gtttagctcc cgctctgatt ctaacgagga aagcacgtta   5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgacccca aaaaacttga   5700
tttgggtgat ggttcacgta gtgggccatc gccctgatag acggtttttc gccctttgac   5760
gttggagtcc acgttcttta atagtggact cttgttccaa actggaacaa cactcaaccc   5820
tatctcgggc tattcttttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcactgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg ctttacactt tatgcttccg gctcgtatgt tgtgtggaat   6180
tgtgagcgga taacaatttc acacaggaaa cagctatgac catgattacg aattcgagct   6240
cggtacccgg ggatcctcta gagtcgacct gcaggcatgc aagcttggca ctggccgtcg   6300
ttttacaacg tcgtgactgg gaaaaccctg gcgttaccca acttaatcgc cttgcagcac   6360
atccccctttt cgccagctgg cgtaatagcg aagaggcccg caccgatcgc ccttcccaac   6420
agttgcgcag cctgaatggc gaatggcgct ttgcctggtt tccggcacca gaagcggtgc   6480
cggaaagctg gctggagtgc gatcttcctg aggccgatac tgtcgtcgtc ccctcaaact   6540
ggcagatgca cggttacgat gcgcccatct acaccaacgt gacctatccc attacggtca   6600
atccgccgtt tgttcccacg gagaatccga cgggttgtta ctcgctcaca tttaatgttg   6660
atgaaagctg gctacaggaa ggccagacgc gaattatttt tgatggcgtt cctattggtt   6720
aaaaaatgag ctgatttaac aaaaatttaa tgcgaatttt aacaaaatat taacgtttac   6780
aatttaaata tttgcttata caatcttcct gtttttgggg cttttctgat tatcaaccgg   6840
ggtacatatg attgacatgc tagttttacg attaccgttc atcgattctc ttgtttgctc   6900
cagactctca ggcaatgacc tgatagcctt tgtagatctc tcaaaaatag ctaccctctc   6960
cggcattaat ttatcagcta gaacggttga atatcatatt gatggtgatt tgactgtctc   7020
cggcctttct caccctttttg aatctttacc tacacattac tcaggcattg catttaaaat   7080
atatgagggt tctaaaaatt tttatccttg cgttgaaata aaggcttctc ccgcaaaagt   7140
attacagggt cataatgttt ttggtacaac cgatttagct ttatgctctg aggctttatt   7200
gcttaatttt gctaattctt tgccttgcct gtatgattta ttggatgtt               7249
```

<210> SEQ ID NO 14
<211> LENGTH: 8462
<212> TYPE: DNA
<213> ORGANISM: PhiX174 bacteriophage

<400> SEQUENCE: 14

```
gagttttatc gcttccatga cgcagaagtt aacactttcg gatatttctg atgagtcgaa     60
aaattatctt gataaagcag gaattactac tgcttgttta cgaattaaat cgaagtggac    120
```

-continued

```
tgctggcgga aaatgagaaa attcgaccta tccttgcgca gctcgagaag ctcttacttt    180
gcgacctttc gccatcaact aacgattctg tcaaaaactg acgcgttgga tgaggagaag    240
tggcttaata tgcttggcac gttcgtcaag gactggttta gatatgagtc acattttgtt    300
catggtagag attctcttgt tgacatttta aaagagcgtg gattactatc tgagtccgat    360
gctgttcaac cactaatagg taagaaatca tgagtcaagt tactgaacaa tccgtacgtt    420
tccagaccgc tttggcctct attaagctca ttcaggcttc tgccgttttg gatttaaccg    480
aagatgattt cgattttctg acgagtaaca aagtttggat tgctactgac cgctctcgtg    540
ctcgtcgctg cgttgaggct tgcgtttatg gtacgctgga ctttgtagga taccctcgct    600
ttcctgctcc tgttgagttt attgctgccg tcattgctta ttatgttcat cccgtcaaca    660
ttcaaacggc ctgtctcatc atggaaggcg ctgaatttac ggaaaacatt attaatggcg    720
tcgagcgtcc ggttaaagcc gctgaattgt tcgcgtttac cttgcgtgta cgcgcaggaa    780
acactgacgt tcttactgac gcagaagaaa acgtgcgtca aaaattacgt gcagaaggag    840
tgatgtaatg tctaaaggta aaaaacgttc tggcgctcgc cctggtcgtc cgcagccgtt    900
gcgaggtact aaaggcaagc gtaaaggcgc tcgtctttgg tatgtaggtg gtcaacaatt    960
ttaattgcag gggcttcggc cccttacttg aggataaatt atgtctaata ttcaaactgg   1020
cgccgagcgt atgccgcatg acctttccca tcttggcttc cttgctggtc agattggtcg   1080
tcttattacc atttcaacta ctccggttat cgctggcgac tccttcgaga tggacgccgt   1140
tggcgctctc cgtctttctc cattgcgtcg tggccttgct attgactcta ctgtagacat   1200
ttttactttt tatgtccctc atcgtcacgt ttatggtgaa cagtggatta agttcatgaa   1260
ggatggtgtt aatgccactc ctctcccgac tgttaacact actggttata ttgaccatgc   1320
cgcttttctt ggcacgatta accctgatac caataaaatc cctaagcatt tgtttcaggg   1380
ttatttgaat atctataaca actattttaa agcgccgtgg atgcctgacc gtaccgaggc   1440
taaccctaat gagcttaatc aagatgatgc tcgttatggt ttccgttgct gccatctcaa   1500
aaacatttgg actgctccgc ttcctcctga gactgagctt tctcgccaaa tgacgacttc   1560
taccacatct attgacatta tgggtctgca agctgcttat gctaatttgc atactgacca   1620
agaacgtgat tacttcatgc agcgttacca tgatgttatt tcttcatttg gaggtaaaac   1680
ctcttatgac gctgacaacc gtcctttact tgtcatgcgc tctaatctct gggcatctgg   1740
ctatgatgtt gatggaactg accaaacgtc gttaggccag ttttctggtc gtgttcaaca   1800
gacctataaa cattctgtgc cgcgtttctt tgttcctgag catggcacta tgtttactct   1860
tgcgcttgtt cgttttccgc ctactgcgac taaagagatt cagtacctta acgctaaagg   1920
tgctttgact tataccgata ttgctggcga ccctgttttg tatggcaact tgccgccgcg   1980
tgaaatttct atgaaggatg ttttccgttc tggtgattcg tctaagaagt ttaagattgc   2040
tgagggtcag tggtatcgtt atgcgccttc gtatgtttct cctgcttatc accttcttga   2100
aggcttccca ttcattcagg aaccgccttc tggtgatttg caagaacgcg tacttattcg   2160
ccaccatgat tatgaccagt gtttccagtc cgttcagttg ttgcagtgga atagtcaggt   2220
taaatttaat gtgaccgttt atcgcaatct gccgaccact cgcgattcaa tcatgacttc   2280
gtgataaaag attgagtgtg aggttataac gccgaagcgg taaaaatttt aatttttgcc   2340
gctgaggggt tgaccaagcg aagcgcggta ggttttctgc ttaggagttt aatcatgttt   2400
cagactttta tttctcgcca taattcaaac tttttttctg ataagctggt tctcacttct   2460
gttactccag cttcttcggc acctgtttta cagacaccta aagctacatc gtcaacgtta   2520
```

```
tattttgata gtttgacggt taatgctggt aatggtggtt ttcttcattg cattcagatg   2580
gatacatctg tcaacgccgc taatcaggtt gtttctgttg gtgctgatat tgcttttgat   2640
gccgacccta aatttttgc ctgtttggtt cgctttgagt cttcttcggt tccgactacc   2700
ctcccgactg cctatgatgt ttatcctttg gatggtcgcc atgatggtgg ttattatacc   2760
gtcaaggact gtgtgactat tgacgtcctt ccccgtacgc cgggcaataa tgtttatgtt   2820
ggtttcatgg tttggtctaa ctttaccgct actaaatgcc gcggattggt ttcgctgaat   2880
caggttatta aagagattat ttgtctccag ccacttaagt gaggtgattt atgtttggtg   2940
ctattgctgg cggtattgct tctgctcttg ctggtggcgc catgtctaaa ttgtttggag   3000
gcggtcaaaa agccgcctcc ggtggcattc aaggtgatgt gcttgctacc gataacaata   3060
ctgtaggcat gggtgagagt tttatcgctt ccatgacgca gaagttaaca ctttcggata   3120
tttctgatga gtcgaaaaat tatcttgata aagcaggaat tactactgct tgtttacgaa   3180
ttaaatcgaa gtggactgct ggcggaaaat gagaaaattc gacctatcct tgcgcagctc   3240
gagaagctct tactttgcga cctttcgcca tcaactaacg attctgtcaa aaactgacgc   3300
gttggatgag gagaagtggc ttaatatgct tggcacgttc gtcaaggact ggtttagata   3360
tgagtcacat tttgttcatg gtagagattc tcttgttgac attttaaaag agcgtggatt   3420
actatctgag tccgatgctg ttcaaccact aataggtaag aaatcatgag tcaagttact   3480
gaacaatccg tacgtttcca gaccgctttg gcctctatta agctcattca ggcttctgcc   3540
gttttggatt taaccgaaga tgatttcgat tttctgacga gtaacaaagt ttggattgct   3600
actgaccgct ctcgtgctcg tcgctgcgtt gaggcttgcg tttatggtac gctggacttt   3660
gtaggatacc ctcgctttcc tgctcctgtt gagtttattg ctgccgtcat tgcttattat   3720
gttcatcccg tcaacattca aacggcctgt ctcatcatgg aaggcgctga atttacggaa   3780
aacattatta atggcgtcga gcgtccggtt aaagccgctg aattgttcgc gtttaccttg   3840
cgtgtacgcg caggaaacac tgacgttctt actgacgcag aagaaaacgt gcgtcaaaaa   3900
ttacgtgcag aaggagtgat gtaatgtcta aaggtaaaaa acgttctggc gctcgccctg   3960
gtcgtccgca gccgttgcga ggtactaaag gcaagcgtaa aggcgctcgt ctttggtatg   4020
taggtggtca acaattttaa ttgcaggggc ttcggcccct tacttgagga taaattatgt   4080
ctaatattca aactggcgcc gagcgtatgc cgcatgacct ttcccatctt ggcttccttg   4140
ctggtcagat tggtcgtctt attaccattt caactactcc ggttatcgct ggcgactcct   4200
tcgagatgga cgccgttggc gctctccgtc tttctccatt gcgtcgtggc cttgctattg   4260
actctactgt agacattttt actttttatg tccctcatcg tcacgtttat ggtgaacagt   4320
ggattaagtt catgaaggat ggtgttaatg ccactcctct cccgactgtt aacactactg   4380
gttatattga ccatgccgct tttcttggca cgattaaccc tgataccaat aaaatcccta   4440
agcatttgtt tcagggttat ttgaatatct ataacaacta ttttaaagcg ccgtggatgc   4500
ctgaccgtac cgaggctaac cctaatgagc ttaatcaaga tgatgctcgt tatggtttcc   4560
gttgctgcca tctcaaaaac atttggactg ctccgcttcc tcctgagact gagctttctc   4620
gccaaatgac gacttctacc acatctattg acattatggg tctgcaagct gcttatgcta   4680
atttgcatac tgaccaagaa cgtgattact tcatgcagcg ttaccatgat gttatttctt   4740
catttggagg taaaacctct tatgacgctg acaaccgtcc tttacttgtc atgcgctcta   4800
atctctgggc atctggctat gatgttgatg gaactgacca aacgtcgtta ggccagtttt   4860
```

-continued

```
ctggtcgtgt tcaacagacc tataaacatt ctgtgccgcg tttctttgtt cctgagcatg   4920
gcactatgtt tactcttgcg cttgttcgtt ttccgcctac tgcgactaaa gagattcagt   4980
accttaacgc taaaggtgct ttgacttata ccgatattgc tggcgaccct gttttgtatg   5040
gcaacttgcc gccgcgtgaa atttctatga aggatgtttt ccgttctggt gattcgtcta   5100
agaagtttaa gattgctgag ggtcagtggt atcgttatgc gccttcgtat gtttctcctg   5160
cttatcacct tcttgaaggc ttcccattca ttcaggaacc gccttctggt gatttgcaag   5220
aacgcgtact tattcgccac catgattatg accagtgttt ccagtccgtt cagttgttgc   5280
agtggaatag tcaggttaaa tttaatgtga ccgtttatcg caatctgccg accactcgcg   5340
attcaatcat gacttcgtga taaaagattg agtgtgaggt tataacgccg aagcggtaaa   5400
aattttaatt tttgccgctg aggggttgac caagcgaagc gcggtaggtt ttctgcttag   5460
gagtttaatc atgtttcaga cttttatttc tcgccataat tcaaactttt tttctgataa   5520
gctggttctc acttctgtta ctccagcttc ttcggcacct gttttacaga cacctaaagc   5580
tacatcgtca acgttatatt ttgatagttt gacggttaat gctggtaatg gtggttttct   5640
tcattgcatt cagatggata catctgtcaa cgccgctaat caggttgttt ctgttggtgc   5700
tgatattgct tttgatgccg accctaaatt ttttgcctgt ttggttcgct ttgagtcttc   5760
ttcggttccg actaccctcc cgactgccta tgatgtttat cctttggatg gtcgccatga   5820
tggtggttat tataccgtca aggactgtgt gactattgac gtccttcccc gtacgccggg   5880
caataatgtt tatgttggtt tcatggtttg gtctaacttt accgctacta aatgccgcgg   5940
attggtttcg ctgaatcagg ttattaaaga gattatttgt ctccagccac ttaagtgagg   6000
tgatttatgt ttggtgctat tgctggcggt attgcttctg ctcttgctgg tggcgccatg   6060
tctaaattgt ttggaggcgg tcaaaaagcc gcctccggtg gcattcaagg tgatgtgctt   6120
gctaccgata acaatactgt aggcatgggt gatgctggta ttaaatctgc cattcaaggc   6180
tctaatgttc ctaaccctga tgaggccgtc cctagttttg tttctggtgc tatggctaaa   6240
gctggtaaag gacttcttga aggtacgttg caggctggca cttctgccgt ttctgataag   6300
ttgcttgatt tggttggact tggtggcaag tctgccgctg ataaaggaaa ggatactcgt   6360
gattatcttg ctgctgcatt tcctgagctt aatgcttggg agcgtgctgg tgctgatgct   6420
tcctctgctg gtatggttga cgccggattt gagaatcaaa aagagcttac taaaatgcaa   6480
ctggacaatc agaaagagat tgccgagatg caaaatgaga ctcaaaaaga gattgctggc   6540
attcagtcgg cgacttcacg ccagaatacg aaagaccagg tatatgcaca aaatgagatg   6600
cttgcttatc aacagaagga gtctactgct cgcgttgcgt ctattatgga aaacaccaat   6660
ctttccaagc aacagcaggt ttccgagatt atgcgccaaa tgcttactca agctcaaacg   6720
gctggtcagt attttaccaa tgaccaaatc aaagaaatga ctcgcaaggt tagtgctgag   6780
gttgacttag ttcatcagca aacgcagaat cagcggtatg gctcttctca tattggcgct   6840
actgcaaagg atatttctaa tgtcgtcact gatgctgctt ctggtgtggt tgatattttt   6900
catggtattg ataaagctgt tgccgatact tggaacaatt tctggaaaga cggtaaagct   6960
gatggtattg gctctaattt gtctaggaaa taaccgtcag gattgacacc ctcccaattg   7020
tatgttttca tgcctccaaa tcttggaggc tttttatgg ttcgttctta ttacccttct    7080
gaatgtcacg ctgattattt tgactttgag cgtatcgagg ctcttaaacc tgctattgag   7140
gcttgtggca tttctactct ttctcaatcc ccaatgcttg gcttccataa gcagatggat   7200
aaccgcatca agctcttgga agagattctg tcttttcgta tgcagggcgt tgagttcgat   7260
```

```
aatggtgata tgtatgttga cggccataag gctgcttctg acgttcgtga tgagtttgta   7320

tctgttactg agaagttaat ggatgaattg gcacaatgct acaatgtgct cccccaactt   7380

gatattaata acactataga ccaccgcccc gaaggggacg aaaaatggtt tttagagaac   7440

gagaagacgg ttacgcagtt ttgccgcaag ctggctgctg aacgccctct taaggatatt   7500

cgcgatgagt ataattaccc caaaaagaaa ggtattaagg atgagtgttc aagattgctg   7560

gaggcctcca ctatgaaatc gcgtagaggc tttgctattc agcgtttgat gaatgcaatg   7620

cgacaggctc atgctgatgg ttggtttatc gtttttgaca ctctcacgtt ggctgacgac   7680

cgattagagg cgttttatga taatcccaat gctttgcgtg actattttcg tgatattggt   7740

cgtatggttc ttgctgccga gggtcgcaag gctaatgatt cacacgccga ctgctatcag   7800

tatttttgtg tgcctgagta tggtacagct aatggccgtc ttcatttcca tgcggtgcac   7860

tttatgcgga cacttcctac aggtagcgtt gaccctaatt ttggtcgtcg ggtacgcaat   7920

cgccgccagt taaatagctt gcaaaatacg tggccttatg gttacagtat gcccatcgca   7980

gttcgctaca cgcaggacgc tttttcacgt tctggttggt tgtggcctgt tgatgctaaa   8040

ggtgagccgc ttaaagctac cagttatatg gctgttggtt tctatgtggc taaatacgtt   8100

aacaaaaagt cagatatgga ccttgctgct aaaggtctag gagctaaaga atggaacaac   8160

tcactaaaaa ccaagctgtc gctacttccc aagaagctgt tcagaatcag aatgagccgc   8220

aacttcggga tgaaaatgct cacaatgaca aatctgtcca cggagtgctt aatccaactt   8280

accaagctgg gttacgacgc gacgccgttc aaccagatat tgaagcagaa cgcaaaaaga   8340

gagatgagat tgaggctggg aaaagttact gtagccgacg ttttggcggc gcaacctgtg   8400

acgacaaatc tgctcaaatt tatgcgcgct tcgataaaaa tgattggcgt atccaacctg   8460

ca                                                                  8462
```

```
<210> SEQ ID NO 15
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15

agtaagcaga tagctcagag caggcgaaca a                                    31


<210> SEQ ID NO 16
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16

gaaatagcta ataacggaag agcccaccat accc                                 34


<210> SEQ ID NO 17
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 17
agtttacata cataaaggtg gcaacataag aaccacgccg ccag 44

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18
aaacgcaaaa tagctaagaa a 21

<210> SEQ ID NO 19
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
aggttgagcg attggcaaat cctcataaca at 32

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
aaaagaactg gcatgtagaa aaaccagaag 30

<210> SEQ ID NO 21
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
tagcgtttcc ctcagagcct aatccaccga ccac 34

<210> SEQ ID NO 22
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
ccctgcaaag acaccacgga ataagtttga tagcagagta gcga 44

<210> SEQ ID NO 23
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23

cctcagagcc gccaaaagaa accagagccg                                   30


<210> SEQ ID NO 24
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24

gagccaccac cggatcagat agcgaccgcc t                                 31


<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25

aaccgccagc catcttaacc a                                            21


<210> SEQ ID NO 26
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26

tttgccttct gtagcggtca tagccccctt at                                32


<210> SEQ ID NO 27
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27

attctgaaac catttgtcac attagcaa                                     28


<210> SEQ ID NO 28
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
```

taccaatcaa tacgcagtat gttagcaatt aagactccaa agac 44

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 29
gtcaccaaca ccgactgcca g 21

<210> SEQ ID NO 30
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30
cattcaacag ggaaggtcat taaaggtgaa ttatc 35

<210> SEQ ID NO 31
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 31
caaaatcacc agtagagggc gattgcacca t 31

<210> SEQ ID NO 32
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 32
accgtatatg gtttaccagc gccttattag aaa 33

<210> SEQ ID NO 33
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 33
gacttatagc ccccacagac agccctcaca acgcctggag gttt 44

<210> SEQ ID NO 34
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
ccctcagatc agaaccgaac cgaacttttg at 32

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
gattagcgag tgtactgaaa c 21

<210> SEQ ID NO 36
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
gatacaggtg tatcaccgta ctcagtagca ttggaa 36

<210> SEQ ID NO 37
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
atgaaagtat taagcaccca ccgcaggctg a 31

<210> SEQ ID NO 38
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
taggggtttt tggatataag cctcaaga 28

<210> SEQ ID NO 39
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 39
ttttgtacaa acgttagcgt taccgtaa 28

<210> SEQ ID NO 40

```
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40

atagcaagcc caatctaaat tttgaggaac c                                    31


<210> SEQ ID NO 41
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41

ccatgttagt cgtctttcca gacgtttaat tgaaag                               36


<210> SEQ ID NO 42
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42

catgaacgat cttatcggtt tatcagctaa ggagccttag taaa                      44


<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43

cgtcaccact tagccgcagg g                                               21


<210> SEQ ID NO 44
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44

gtatgggaca actttcaaat ccgcgacctg ct                                   32


<210> SEQ ID NO 45
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
```

gccactacgt taatgctgag taacagtgcc cgaggc 36

<210> SEQ ID NO 46
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 46
ctcagcagga atacacaagg ccgcaacg 28

<210> SEQ ID NO 47
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
aaaaaggaag tttccattaa ggcggatatt tt 32

<210> SEQ ID NO 48
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
ctaataaaga ctagtgccgt cgagagggca gtaccaacgg gtaa 44

<210> SEQ ID NO 49
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 49
aaagtataaa cagaaggcac caac 24

<210> SEQ ID NO 50
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
catgcgaaag acttgaggac ttttgcgg 28

<210> SEQ ID NO 51
<211> LENGTH: 44
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 51

aattgtgaat ttgcaacggc tacagaggca tcggaatgcg ccga                    44


<210> SEQ ID NO 52
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52

aaccatcgac cgatattata ccaagcgcga aa                                  32


<210> SEQ ID NO 53
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53

aacaaaggct ccctttcgag ttttcacg                                      28


<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54

ccaaaaaaaa cggagagaac a                                             21


<210> SEQ ID NO 55
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55

actaaaggaa ttgcgcatac ccacgaataa t                                  31


<210> SEQ ID NO 56
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56

caaagtacgc ttgataccga tagtcgaggg tactta                             36
```

<210> SEQ ID NO 57
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
tgtatcatcg cctgataaat tgtgt 25

<210> SEQ ID NO 58
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
aaacactcat ctttgacccc cagcg 25

<210> SEQ ID NO 59
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59
caccctcaga gccaccaccc tcatt 25

<210> SEQ ID NO 60
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 60
cctgcctatt tcggaaccta ttatt 25

<210> SEQ ID NO 61
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 61
cagtttcagc ggagtgagaa tagaa 25

<210> SEQ ID NO 62
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 62
taataagttt taacggggtc agtgc 25

<210> SEQ ID NO 63
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 63
acgaggcgca gacggtcaat cataa 25

<210> SEQ ID NO 64
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
tcggtcgctg aggcttgcag ggagt 25

<210> SEQ ID NO 65
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
cttgccctac taatgcagat acatatagcg tccaca 36

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
aataaaacga cgagaaaact g 21

<210> SEQ ID NO 67
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
ttcagaacta actgagattt ggaagaaa 28

<210> SEQ ID NO 68
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
gaggcataca ctatcaatat gtacccataa gg 32

<210> SEQ ID NO 69
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gttgaggaat accaatactg cggaatcgta gactggaacg ccaa 44

<210> SEQ ID NO 70
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gctcattata ccagagcaag taagtcagga c 31

<210> SEQ ID NO 71
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gagaatcgaa atgctttaaa cagtaaccag actccc 36

<210> SEQ ID NO 72
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
cataaatctc tttaccagtc tggagcaaac aa 32

<210> SEQ ID NO 73
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
ccaaaatagc gagatcagga aaaaggcttt t 31

<210> SEQ ID NO 74
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
cctcgtaaaa tgataaatat aagaagtt 28

<210> SEQ ID NO 75
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 75
gcaatcattg aacggaagca aactccaatc aaagcgtcag aaaa 44

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
gggtaataat gaacggaaaa a 21

<210> SEQ ID NO 77
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 77
ggagagcctc aggaccctgt aaagaatt 28

<210> SEQ ID NO 78
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 78
atgtaagcct ttatttcaac tattacagtg cg 32

<210> SEQ ID NO 79
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 79
atgcaatact ttgtagaaag attcatcaaa caacatgcaa ggat 44

<210> SEQ ID NO 80
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 80
agcaataagt aggtaaggca aggcaatg 28

<210> SEQ ID NO 81
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
agaaccctta atcattcttg agatggttta atagta 36

<210> SEQ ID NO 82
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 82
cctgttcaac ttcatatatt ttaa 24

<210> SEQ ID NO 83
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
tgattccctg atattcatat g 21

<210> SEQ ID NO 84
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
tggcatcata gtagtagaga cagtcaaatc ac 32

<210> SEQ ID NO 85
<211> LENGTH: 44
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
aagtgtcaat aattgtacca aaaacattca taaagcgggc gcga 44

<210> SEQ ID NO 86
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 86
caactaaagt acggactaaa ttcttgtctg g 31

<210> SEQ ID NO 87
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 87
tttaaattct gccgcaaatg ttcattcc 28

<210> SEQ ID NO 88
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88
catcaatagc tatattttca tttgtaaatc ggcctg 36

<210> SEQ ID NO 89
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 89
tttttgagat tgctcctttt gataatttag tttacc 36

<210> SEQ ID NO 90
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
tttaaattcg agggtcagga ccgaaaga 28

<210> SEQ ID NO 91
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91
tgcatcaaaa agataattga gctttaagag g 31

<210> SEQ ID NO 92
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 92
aagcttagag agtgaccatt agatacatac gagtagagag gtca 44

<210> SEQ ID NO 93
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 93
tggcttagct gaatatccgg agagggtagc ta 32

<210> SEQ ID NO 94
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 94
cgcgttttag atctaccgga t 21

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
accagaacga gtagtaaatt g 21

<210> SEQ ID NO 96
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 96
gactattata gtcagaagca a 21

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 97
atcgtaaaac tagcatgtca a 21

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 98
tgctgtagct caacatgttt t 21

<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 99
gaattacctt atgcgatttt a 21

<210> SEQ ID NO 100
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
accctcgttt accagacgac g 21

<210> SEQ ID NO 101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
attcaaaagg gtgagaaagg c 21

<210> SEQ ID NO 102
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102

attaacatcc aataaatcat a                                            21


<210> SEQ ID NO 103
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103

aggctatcag gtcattgcct g                                            21


<210> SEQ ID NO 104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104

ccgttctagc tgataaatta a                                            21


<210> SEQ ID NO 105
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105

aatagcgaca aaagaaccgt gcatctaact tt                                32


<210> SEQ ID NO 106
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106

aatcattgta accctcgttt accattaaac agcact                            36


<210> SEQ ID NO 107
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
```

```
aaagaagagc aattcagaaa acgagaatca aatgctgacg acga                44


<210> SEQ ID NO 108
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108

atcacacatt caggcatagt attcatca                                  28


<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109

aggaatactg aattactaac g                                         21


<210> SEQ ID NO 110
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110

gaacaacatt attattttgg aggccaggta g                              31


<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111

tattcattgt cacgtttaaa a                                         21


<210> SEQ ID NO 112
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112

tgggatagac cctgactatt atagctcctt ttaggt                         36


<210> SEQ ID NO 113
<211> LENGTH: 44
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 113

aatacaaaaa tcgataagag gtcatttttt taattgtcag aagc                        44


<210> SEQ ID NO 114
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114

ctttgaatcc ccccataaat ctgcggaa                                          28


<210> SEQ ID NO 115
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115

gcatcaaagg aagcccggcg gattgaccgt aa                                     32


<210> SEQ ID NO 116
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116

tgtttagact ggattaagaa agatagcgtc c                                      31


<210> SEQ ID NO 117
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117

ttatatgcaa tgttgcctga gagtctggaa aggctatcaa aagg                        44


<210> SEQ ID NO 118
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118

ccggagaccc atcaattatt ttgttaaaat tc                                     32


<210> SEQ ID NO 119
```

<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
agtagccttt attattttaa gaccctgt 28

<210> SEQ ID NO 120
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 120
aaatcggttg taccaatcaa gtcaaaaaac a 31

<210> SEQ ID NO 121
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
cgggagaatt tttgttaagc t 21

<210> SEQ ID NO 122
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
gcattaaaat gtgtaggtaa agattcaggt cacctg 36

<210> SEQ ID NO 123
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
caggggacgt tgaatcagaa aagc 24

<210> SEQ ID NO 124
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124
cggttgatgg aagaaactca ttataccagt caaaga 36

<210> SEQ ID NO 125
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125
cccaagaatc gacgccaaaa ggaattacta atgcagtgtc aatc 44

<210> SEQ ID NO 126
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126
tatttttgat aagcaagata aattaaaa 28

<210> SEQ ID NO 127
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 127
cggtagagat ctcaaacaag aatgccgg 28

<210> SEQ ID NO 128
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 128
ttgtaatcgt aaaactagca atacataatg aa 32

<210> SEQ ID NO 129
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
actaggtcaa tagaaaaggt ttgaccat 28

<210> SEQ ID NO 130
<211> LENGTH: 32
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 130
ggcaaggcca aaattaatag gaacgccatc aa 32

<210> SEQ ID NO 131
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 131
aaataattat agtagtagca ttaaggataa aattct 36

<210> SEQ ID NO 132
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 132
aattctgcga acgaattaga aagagtagat t 31

<210> SEQ ID NO 133
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 133
tcgcaaatcg cgtctgttcc c 21

<210> SEQ ID NO 134
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 134
tagtggcatc aaatttttag aaccctcaca acgcaacatc caat 44

<210> SEQ ID NO 135
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
tgctagagag tacggatggc gaagcaaa 28

<210> SEQ ID NO 136
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
accgttagag cttcatttgg ggcgcgagct gtttagctca acat 44

<210> SEQ ID NO 137
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
tcaggattca acccgtttaa t 21

<210> SEQ ID NO 138
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
tcgagcttca aagccggtga agtagaacca g 31

<210> SEQ ID NO 139
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
tgcaactatc tggaagtcaa cattaaatgt ga 32

<210> SEQ ID NO 140
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
gcgagtaaga atataatgct gtagctatat tttaat 36

<210> SEQ ID NO 141
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 141
atttaaattg taaacgtt 18

<210> SEQ ID NO 142
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
tcattccata taacagtt 18

<210> SEQ ID NO 143
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
tgtagatggg cgcatcgt 18

<210> SEQ ID NO 144
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 144
gattctccgt gggaacaa 18

<210> SEQ ID NO 145
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
atcagctcat tttttaac 18

<210> SEQ ID NO 146
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
cttcctgtag ccagcttt 18

<210> SEQ ID NO 147
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
tctacgttaa taaaacga 18

<210> SEQ ID NO 148
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
tttgccagag ggggtaat 18

<210> SEQ ID NO 149
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
aagacttcaa atatcgcg 18

<210> SEQ ID NO 150
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 150
tatgcgattt taagaact 18

<210> SEQ ID NO 151
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
caataaagcc tcagagca 18

<210> SEQ ID NO 152
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
gatattcaac cgttctag 18

<210> SEQ ID NO 153
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
gtagtcgtcg cttagcttag tgagaagag 29

<210> SEQ ID NO 154
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
cgttagaacg cgaaaaaagc ctgtgctaag ttcattag 38

<210> SEQ ID NO 155
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
aatagtttaa cgtcagatga accatatcat cattttatat 40

<210> SEQ ID NO 156
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
attatttgca cgtaaaacag attgc 25

<210> SEQ ID NO 157
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
aataaatgat gaaacaaatt aattacattt aacaatttca ctt 43

<210> SEQ ID NO 158
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
cttgaaaacg aattatagca aaagaagaga aa 32

<210> SEQ ID NO 159
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
cgacaataaa caacattgca gaactgtttt ga 32

<210> SEQ ID NO 160
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
aaaagaaaat tttcagccaa gttacaaaa 29

<210> SEQ ID NO 161
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
gaacaattac taggaaaact ttttcaaata atagattcaa ttcga 45

<210> SEQ ID NO 162
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
gagcggaatt gtttggggaa gggttagaac ctata 35

<210> SEQ ID NO 163
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
aaccattaaa tctaacagta acaataacgg at 32

<210> SEQ ID NO 164
<211> LENGTH: 22
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164

tcgcgcagag gcatagcgaa tt                                              22


<210> SEQ ID NO 165
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165

tcgcctgatt gctattagac gaa                                             23


<210> SEQ ID NO 166
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166

gcaattcatc aatataatcc tgattatcat cgcg                                 34


<210> SEQ ID NO 167
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167

ataatacatt aagacaaatt aattttgtaa cattaaa                              37


<210> SEQ ID NO 168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168

attaaggatt tagaagtttg                                                 20


<210> SEQ ID NO 169
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169

tacagctttg ccctttacaa aagagccgtc aatag                                35
```

<210> SEQ ID NO 170
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
tgagtgaata acatggaaac ccagacga 28

<210> SEQ ID NO 171
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
tcaatagtga atttactata tgtattttcc ctatg 35

<210> SEQ ID NO 172
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
aattaaaatg ctgttatcaa caatagataa attctgtagt acata 45

<210> SEQ ID NO 173
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
ttttacttgc ttcgcgcctg tatgcaaatc caatcgctga gacgc 45

<210> SEQ ID NO 174
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 174
tcctgattat cagatattac tttgagatg 29

<210> SEQ ID NO 175
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 175
tatcatatgc gttatacaaa ttcgaatcat aaaga 35

<210> SEQ ID NO 176
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
ttgctcactt gcctatcatt cc 22

<210> SEQ ID NO 177
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
tagagtctgt cccttctgac acgtggcaca ga 32

<210> SEQ ID NO 178
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
aataaaaccc tcaattgagg aaaatatct 29

<210> SEQ ID NO 179
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
ttaggagcac taacatttta gtttctggtc aaaag 35

<210> SEQ ID NO 180
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
tttacccgcc agccattgca acaggaaaag cc 32

<210> SEQ ID NO 181
<211> LENGTH: 40

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
atataatcgc catatttaac aacgccaatc tttccttgag 40

<210> SEQ ID NO 182
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
catcaccttg ctgagccagc aagccaac 28

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
aaggtctgag aagtgtatgg 20

<210> SEQ ID NO 184
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
aatggtttga aacgggtatt aaaccaagta ccaaagggat gccaccga 48

<210> SEQ ID NO 185
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
caataaattt cattaaataa gaataaacac cagtataagc aaatg 45

<210> SEQ ID NO 186
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 186
gctcaacagt agggctgtga taaaaatttc tt 32

<210> SEQ ID NO 187
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 187
caatattttt gattttataa aat 23

<210> SEQ ID NO 188
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 188
gctgagaacc tcataaggcg tcttctgacc taaatttatc tatct 45

<210> SEQ ID NO 189
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 189
aagaataccg accgttaatt gagccagaa 29

<210> SEQ ID NO 190
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 190
gtcacccacc agcagaaggc ggtcagtatt aacaccgcct cac 43

<210> SEQ ID NO 191
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 191
atcaacaggc cctaaatacc gaacgaaacg ac 32

<210> SEQ ID NO 192
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 192
aatacatcaa agggactagt ctttaatgc 29

<210> SEQ ID NO 193
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193
caataagtgc gcaacttaat tggcagattc accacagt 38

<210> SEQ ID NO 194
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 194
taaccgttgt agctgattag ttta 24

<210> SEQ ID NO 195
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
gcgaactgat attgaaagga at 22

<210> SEQ ID NO 196
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
ctatattctg gccaacagag gaaatggaaa taacatggta 40

<210> SEQ ID NO 197
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
gaaccatcac gcatcagtga gtttagacag gaacggtacg ccaga 45

<210> SEQ ID NO 198

<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
aactatcgac gctcattgac gctcaatcgt ctata 35

<210> SEQ ID NO 199
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 199
tgaacgctac agctttcctc gagcgggag 29

<210> SEQ ID NO 200
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
tttaagggga aagccgagga agggaagaaa gcgaaaggag ggc 43

<210> SEQ ID NO 201
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
caccacaccc gccaagtgta ggcagagg 28

<210> SEQ ID NO 202
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 202
gtataacagg gagaattaac tgaacaccca agttttcaat agcacgc 47

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 203
gttagattac cgcgccttgg 20

<210> SEQ ID NO 204
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
gagcacgtga accctataga gcttgaccgt ca 32

<210> SEQ ID NO 205
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205
cattttcgag ccagtattac gagcatgtcc cg 32

<210> SEQ ID NO 206
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
atttatataa agtaccgaca aaaggtaacc tgaacaaaat caagtccg 48

<210> SEQ ID NO 207
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 207
ctattttgga gcctaataaa cagccatatt ataacataaa tcta 44

<210> SEQ ID NO 208
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 208
ggtcccttta cagagagaat ttatcccaga ggtttttaca 40

<210> SEQ ID NO 209
<211> LENGTH: 22
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 209
gcactaaatc gataacgtgg gc 22

<210> SEQ ID NO 210
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 210
cctccggaat atcccatcct aatataagag atatcct 37

<210> SEQ ID NO 211
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 211
gaacccgcaa tagcaggagg tgccgtaaa 29

<210> SEQ ID NO 212
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 212
gcgtagaaca agcaccaatc aataatcggg taatttagcg gtcac 45

<210> SEQ ID NO 213
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 213
agaaagcaaa tcggtctgag agactacctt ttaggacatc gttaa 45

<210> SEQ ID NO 214
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 214
caaatccaac gctaacgagc gtctttccac acccagcgaa 40

```
<210> SEQ ID NO 215
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215

gaatcgctag cgggcttaaa gaaacgattt tttgaaaa                              38


<210> SEQ ID NO 216
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216

gaggcgtttt agcacttgcg gatc                                             24


<210> SEQ ID NO 217
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217

gccttagaaa aatcttaggt tgggttataa aatcataaga tatag                      45


<210> SEQ ID NO 218
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218

gctggcgcgc ttaatgtaga aaagccgttt ttattttatc aatca                      45


<210> SEQ ID NO 219
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219

ctaaacagga ggccgctcat cgactatggt ttaac                                 35


<210> SEQ ID NO 220
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 220
tagtaccaaa atagcgagag gcttttgcca taacgctcat aaat 44

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
cgagtagtaa gattcatcag 20

<210> SEQ ID NO 222
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
atagcgtcac cataaaggta acgccagg 28

<210> SEQ ID NO 223
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
gttttcccag tccagagggg cgga 24

<210> SEQ ID NO 224
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
gataaaaagg aagatttaga agttttgcac gacgtttaaa c 41

<210> SEQ ID NO 225
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
attcattgaa atgcttgtaa aacgacgcag aa 32

<210> SEQ ID NO 226
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
atcgcaaaag gaattacgag gcatagtacg ataaaaaaaa tgtt 44

<210> SEQ ID NO 227
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
ttgataccac ataatatttt gttaaaattt aaattgcgga acaa 44

<210> SEQ ID NO 228
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
agttcagaaa acgagaatgc aatactggta a 31

<210> SEQ ID NO 229
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 229
ctaataaacg tttcaactaa tgca 24

<210> SEQ ID NO 230
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
aatctacgtt aataccctca atccaaacga a 31

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
caggtagaaa attgggagaa a 21

<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
acgccagcct tcaaatatcg 20

<210> SEQ ID NO 233
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
gaagctgtcg agttaattag ctcaacatat cggtgcgacc a 41

<210> SEQ ID NO 234
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
cgttcttcaa agccctcgtt taccagacag caacacaaga ttaa 44

<210> SEQ ID NO 235
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
cagaagcaaa gcgggtagaa acgaattgca t 31

<210> SEQ ID NO 236
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 236
caacagagct taattgctga atataatgca aactccgatt ccca 44

<210> SEQ ID NO 237
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 237
caaatatcat aacgaaccag accg 24

<210> SEQ ID NO 238
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 238
agttaacagg tcaggattag agagtaccga tggctttaaa gtac 44

<210> SEQ ID NO 239
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
gaagtttcgg tcaatagctg cgcaactg 28

<210> SEQ ID NO 240
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
ttagatacat ttcgcaaata ttccatatat g 31

<210> SEQ ID NO 241
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 241
ttgggaaggg cggttttaaa taac 24

<210> SEQ ID NO 242
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 242
ccgaaagatg gcgaaaatag t 21

<210> SEQ ID NO 243
<211> LENGTH: 32
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 243
attctgcgtt tagtttgggc ctcttcgcta tt 32

<210> SEQ ID NO 244
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 244
cagctcattt ttgccccaaa atgtgagc 28

<210> SEQ ID NO 245
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 245
tcaaaacatt aaaacaggaa gatt 24

<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 246
gatgggcgtc gtaaaactag 20

<210> SEQ ID NO 247
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 247
gtataagcaa atgcattaaa cgcgtctg 28

<210> SEQ ID NO 248
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
agcacctgta atgttgataa tcag 24

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
aacggtaaca tcgtaatatc a 21

<210> SEQ ID NO 250
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
gagtaacatt ctccgtaggt cacgttggtg ta 32

<210> SEQ ID NO 251
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
gtagccagta agaactattg tgaattacct tattgaccgt gcca 44

<210> SEQ ID NO 252
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
catggtaccc cgacttttgc gggagaagat tatgacaaca agag 44

<210> SEQ ID NO 253
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
aaaataacat attcaatcca ataggaacaa tgggatggga 40

<210> SEQ ID NO 254
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 254
acaaacggcg gatgcgattt cttt 24

<210> SEQ ID NO 255
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
catcaaataa ttttttgtt aaat 24

<210> SEQ ID NO 256
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
ggtcattgcc tgagtcggaa cccgagtctg g 31

<210> SEQ ID NO 257
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
gccgaaagct aaatcggttg taccaaaatt tatttcgtaa tgtg 44

<210> SEQ ID NO 258
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
gcaatagcaa aataagaggt catttttgta attgctaata gtag 44

<210> SEQ ID NO 259
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
ctgaaacgca aggataaaaa tttttagaca gagcatgaga cagt 44

<210> SEQ ID NO 260
<211> LENGTH: 31

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260

ctagctgata aattaatgca gggtgagatg c                              31


<210> SEQ ID NO 261
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261

tactcctttt gattaagcaa taaa                                      24


<210> SEQ ID NO 262
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262

gcctaccaga atggcaactc atatatttgc actccaccgt t                   41


<210> SEQ ID NO 263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263

acatccaagt gccggagcga g                                         21


<210> SEQ ID NO 264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264

cgcttctgta aatcatacag                                           20


<210> SEQ ID NO 265
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
```

ctcaggaaga tctaaatgca aaag 24

<210> SEQ ID NO 266
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
gattcaaacg gagagggaca gtatcggc 28

<210> SEQ ID NO 267
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
caaatcacat attcaagcca gctttccggc ac 32

<210> SEQ ID NO 268
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
ctgaaaaggt ggcaatatgc atcatcaatt c 31

<210> SEQ ID NO 269
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
aaaaatcagg tctttaccct gacta 25

<210> SEQ ID NO 270
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 270
ctgtttagct atattttcat ttggg 25

<210> SEQ ID NO 271
<211> LENGTH: 25
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 271

tgagatggtt taatttcaac tttaa                                             25


<210> SEQ ID NO 272
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272

ccaggcaaag cgccattcgc cattc                                             25


<210> SEQ ID NO 273
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273

ctcattatac cagtcaggac gttgg                                             25


<210> SEQ ID NO 274
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274

gtgcatctgc cagtttgagg ggacg                                             25


<210> SEQ ID NO 275
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275

agctattttt gagagatcta caaag                                             25


<210> SEQ ID NO 276
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276

gggatgtgct gcaaggcgat taagt                                             25


<210> SEQ ID NO 277
```

<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
aaacaggtcg tcaaactatc aaaacattac ca 32

<210> SEQ ID NO 278
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
tcctaagcgc cgaagaagct ggagtgtctg ta 32

<210> SEQ ID NO 279
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
gcgcacctaa gaaaaagagt aaacagatta aac 33

<210> SEQ ID NO 280
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
gacgggagtg gagaatgtag ctttaacaga agt 33

<210> SEQ ID NO 281
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
gagaaccagc ttatcagaaa aaaagtagtg tt 32

<210> SEQ ID NO 282
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 282
aacagtcggg gttaatcgtg ccaagatttt at 32

<210> SEQ ID NO 283
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 283
ctcaggaagt cgcagtaggc ggaagtactg aa 32

<210> SEQ ID NO 284
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 284
tggcgagaaa taaaagtctg aaacgtgcca tg 32

<210> SEQ ID NO 285
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 285
catgaaacgc aaaggtcaat ataacttgaa tta 33

<210> SEQ ID NO 286
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 286
gcattaaccg ttgacagatg tatcacaacc tgaattaaaa 40

<210> SEQ ID NO 287
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
tctctttagc cagcaatatc ggtacataca aaccagaaaa 40

<210> SEQ ID NO 288
<211> LENGTH: 40
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 288
tggtatcagt tgttatagat attcacggcg cttgttcacc 40

<210> SEQ ID NO 289
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
cagcaatcaa gaaggtatac gaagggcgaa taagtacgcg tggttcatct tcacactact 60

<210> SEQ ID NO 290
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
gacggaagga gtgagagcgc caacggcgca tgaactgtaa tcatcttcac actact 56

<210> SEQ ID NO 291
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
tgggaagcct tcaatttaac atcatcatct tcacactact 40

<210> SEQ ID NO 292
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
tggtatagcc agatgcccag cagttcatct tcacactact 40

<210> SEQ ID NO 293
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 293
cggtacggca acggaatctt gattgcggag catcatcttc acactact 48

<210> SEQ ID NO 294
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 294
cacgtccaaa tggtcagcgt cataagaggg tctgtttcaa tcatcttcac actact 56

<210> SEQ ID NO 295
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 295
tatatcaggc atataaccct aagctcattc atcttcacac tact 44

<210> SEQ ID NO 296
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 296
gtcaggcaag ttagtcaaag aacatccttc atcttcacac tact 44

<210> SEQ ID NO 297
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 297
accgaagaca tcatggaaac atcagaccag caaggaagcc ataatcatct tcacactact 60

<210> SEQ ID NO 298
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
ggtagaagtc gtgttttacc ttcttcatct tcacactact 40

<210> SEQ ID NO 299
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
gatggcagca tttggcagga ggaacagtat gcaaattagc taattcatct tcacactact 60

<210> SEQ ID NO 300
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
cacgcggctt aaacttgaac ggaagcgcat aatcatcttc acactact 48

<210> SEQ ID NO 301
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
atatcagcag actcaaaaaa aatttaggca gttcatcttc acactact 48

<210> SEQ ID NO 302
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
atctgtctac agtagagtca catatcatct tcacactact 40

<210> SEQ ID NO 303
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
catactgact atataaacgg tcacattaac ccctcacact tcatcttcac actact 56

<210> SEQ ID NO 304
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 304
agtttgaacc actccatctc accatcatct tcacactact 40

<210> SEQ ID NO 305
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 305
ccttaccaac agtctgaatg tagggtcgtc atcttcacac tact 44

<210> SEQ ID NO 306
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 306
tggtctttta tcacgaagtc taactcatct tcacactact 40

<210> SEQ ID NO 307
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 307
cctacgagtc agtccttcca gaacacgaac agggtctgtt 40

<210> SEQ ID NO 308
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 308
cctacgagtc agtcctgcat gaagataagc aggtcaatag atgt 44

<210> SEQ ID NO 309
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 309
cctacgagtc agtcctctca gcggcaaaat tagcggcttg 40

<210> SEQ ID NO 310
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 310
cctacgagtc agtcctaaat caataacagg cattgaagaa aacctaacgt t 51

```
<210> SEQ ID NO 311
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311

cctacgagtc agtcctatga gggaatagca aggaaagacg cgccagcg                48


<210> SEQ ID NO 312
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312

cctacgagtc agtcctcgtt tggtagatta gaggacggtt aagaaata                48


<210> SEQ ID NO 313
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313

cctacgagtc agtcctaaat ggtaaagatg ggacgctcgg cgcc                    44


<210> SEQ ID NO 314
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314

cctacgagtc agtcctcaat caccttcgcc gcgctttagc gttacgaaca a            51


<210> SEQ ID NO 315
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315

cctacgagtc agtcctaaaa taatccactt aaaataccat                        40


<210> SEQ ID NO 316
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 316
cctacgagtc agtcctcatc gaacagaacg gcaacaaatg cttaaaagcg g 51

<210> SEQ ID NO 317
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 317
cctacgagtc agtcctcggc gttaatgatt gaagattgcg tccactgc 48

<210> SEQ ID NO 318
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
cctacgagtc agtcctggaa acacttcttg cattcctgaa tgaa 44

<210> SEQ ID NO 319
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
acagtattgt tatcggtagc aagcaactta at 32

<210> SEQ ID NO 320
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 320
ccactgtttt aacagtcggg agagaatata ac 32

<210> SEQ ID NO 321
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 321
caggtaaacc accagttagg aacatccatg cct 33

<210> SEQ ID NO 322
<211> LENGTH: 33
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 322
taacaggtct ttataccatc cttcaatcac ctt 33

<210> SEQ ID NO 323
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 323
acagaatgca agcgcaagag taaagtaggc gg 32

<210> SEQ ID NO 324
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 324
gaatgccacc ggaggcggct ttttaacgcg gc 32

<210> SEQ ID NO 325
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 325
agaacagcaa ccgcataaaa gtctgcaaga gca 33

<210> SEQ ID NO 326
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 326
aatggcagga aacaaaacta gggatttagc ca 32

<210> SEQ ID NO 327
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 327
gaagcaatat ttaataccag catcgagcct tg 32

<210> SEQ ID NO 328
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 328
atgcgaaaaa agcatcagga acaaaccgcc tcc 33

<210> SEQ ID NO 329
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 329
aaactcctca gaaaaaaagt ttgagtgaga ac 32

<210> SEQ ID NO 330
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 330
aaacaattta gacatggcgc caccacatga tt 32

<210> SEQ ID NO 331
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 331
catatcaagc aaaccttcaa ggcagacttc atcttcacac tact 44

<210> SEQ ID NO 332
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
aaatccggtc ggcaatagtt gcatgaccag caaggaagcc ataatcatct tcacactact 60

<210> SEQ ID NO 333
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 333
caaccaaacg tcaaccttat cagctttagt aatcatcttc acactact 48

<210> SEQ ID NO 334
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
gacggaagga gtcatcatct caacggcgaa aagtaagaaa tcatcttcac actact 56

<210> SEQ ID NO 335
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 335
agtttgtgca tctccatctc accatcatct tcacactact 40

<210> SEQ ID NO 336
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 336
atctgagagc gctgattaag gcaatcatct tcacactact 40

<210> SEQ ID NO 337
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
agaaccctga aacgtgccaa aaaatagttc atcttcacac tact 44

<210> SEQ ID NO 338
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
aacggagcgc attaaacttc agattcatct tcacactact 40

<210> SEQ ID NO 339
<211> LENGTH: 56

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339

atcattgtca gcagcaatct gacaagtaaa ctggccagag tcatcttcac actact        56


<210> SEQ ID NO 340
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340

aagcggagat gtcaatgtca tttgctgcat gaagtaatca taactcatct tcacactact    60


<210> SEQ ID NO 341
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341

tgcagaccca taaaggacgg tggttcatct tcacactact                          40


<210> SEQ ID NO 342
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342

tcaaataaca gtccaaggcg ctttgcgaga aatcatcttc acactact                  48


<210> SEQ ID NO 343
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343

aaggatccgc ggagctcagg tgattcatct tcacactact                          40


<210> SEQ ID NO 344
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
```

aaacaggcaa acatcatagt cggaacgtca atagtcacac cggctcatct tcacactact 60

<210> SEQ ID NO 345
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 345
gtacagttag acaagcatta catttagtca cctcaccgaa tcatcttcac actact 56

<210> SEQ ID NO 346
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 346
actatcaaaa aaaattaacc accaaccgaa gatcatcttc acactact 48

<210> SEQ ID NO 347
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 347
catccaaagg atagcggtaa ggggtcatct tcacactact 40

<210> SEQ ID NO 348
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 348
aaataatata acgccgaaga ttaccagctc atcttcacac tact 44

<210> SEQ ID NO 349
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 349
caaaacagag caggagaaat ttcatgaatg aatcatcttc acactact 48

<210> SEQ ID NO 350
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 350
ggcgaataag taagtcatga taactcatct tcacactact 40

<210> SEQ ID NO 351
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 351
aggtgatacg cgttctgcgg ttccctattc cactgcaaca attatcatct tcacactact 60

<210> SEQ ID NO 352
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 352
cttgggtcgc caaggtactg cgcggcggtc atcttcacac tact 44

<210> SEQ ID NO 353
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 353
ctgacaatct ttgattagcg gttatcatct tcacactact 40

<210> SEQ ID NO 354
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 354
aattttgaat cgaacaacct tatcacgagt caacccctca tcatcttcac actact 56

<210> SEQ ID NO 355
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 355
cctacgagtc agtcctgcca cgacctcatt agataacgag cgccagcg 48

<210> SEQ ID NO 356

<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 356
cctacgagtc agtcctaaat ggtaaagatg ggacgctcgg cgcc 44

<210> SEQ ID NO 357
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 357
cctacgagtc agtccttgga aaatgtctgg gattttggga 40

<210> SEQ ID NO 358
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 358
cctacgagtc agtcctgacg gaagatgagt gacgtccttt accagcctca t 51

<210> SEQ ID NO 359
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 359
cctacgagtc agtccttgaa gaaacgttct tggcataagc agct 44

<210> SEQ ID NO 360
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 360
cctacgagtc agtcctgccc taacgacgta taagtcgacc 40

<210> SEQ ID NO 361
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 361
cctacgagtc agtcctatta gaaaacactg ttgaagcggc atgggtggca t 51

<210> SEQ ID NO 362
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 362
cctacgagtc agtccttcat agccttagac gatgaccctc gtcataag 48

<210> SEQ ID NO 363
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 363
cctacgagtc agtccttcag ttaagtggac ggcagaacat 40

<210> SEQ ID NO 364
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 364
cctacgagtc agtcctacca agcaccaaat agctggagta acagtatggc g 51

<210> SEQ ID NO 365
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
cctacgagtc agtcctttat tgccagtcct tgcatcatgg cgac 44

<210> SEQ ID NO 366
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
cctacgagtc agtccttaat aaccaaatgc agacgctccc caaaccat 48

<210> SEQ ID NO 367
<211> LENGTH: 48
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 367
cctacgagtc agtcctgctt cggcgcgttg acccaacaga cgagtggt 48

<210> SEQ ID NO 368
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
cctacgagtc agtccttaac ctcagcggta gctttattcg 40

<210> SEQ ID NO 369
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 369
cctacgagtc agtcctcact aatcgcgccc tacctcttta gtcgtagtgc c 51

<210> SEQ ID NO 370
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 370
cctacgagtc agtcctacgg tcacactgaa cgcataatca tggt 44

<210> SEQ ID NO 371
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371
tagcaccaag tgccagcctg caactatcag aactggagac 40

<210> SEQ ID NO 372
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
cagtagtgat tggtatcagg gttaaatgct taacagtaga 40

<210> SEQ ID NO 373
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
aaaacgaaaa agcaccttta gcgtaatatc ggtttggtca 40

<210> SEQ ID NO 374
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
cagcttatgg tgtctgtaaa acagtgacga tgcaaaaatt 40

<210> SEQ ID NO 375
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 375
tagcaccaag tgccagcctg caactagctc actcagtctc a 41

<210> SEQ ID NO 376
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 376
tatcagaact ggagac 16

<210> SEQ ID NO 377
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
cagtagtgat tggtatcagg gttatagctc actcagtctc a 41

<210> SEQ ID NO 378
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 378
aatgcttaac agtaga 16

<210> SEQ ID NO 379
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 379
aaaacgaaaa agcaccttta gcgttaactt cctatctcac t 41

<210> SEQ ID NO 380
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
aatatcggtt tggtca 16

<210> SEQ ID NO 381
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
cagcttatgg tgtctgtaaa acagtaactt cctatctcac t 41

<210> SEQ ID NO 382
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
tgacgatgca aaaatt 16

<210> SEQ ID NO 383
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
accagcagag gaagcatcag cacca 25

<210> SEQ ID NO 384
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
gtttttgaga tggcagcaac ggaaa 25

<210> SEQ ID NO 385
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 385
acatacgaag gcgcataacg atacc 25

<210> SEQ ID NO 386
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 386
gggtcggcat caaaagcaat atcag 25

<210> SEQ ID NO 387
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 387
gcaagataat cacgagtatc ctttc 25

<210> SEQ ID NO 388
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 388
ttagcctcgg tacggtcagg catcc 25

<210> SEQ ID NO 389
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 389
caccagaacg gaaaacatcc ttcat 25

<210> SEQ ID NO 390
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 390
atgtatccat ctgaatgcaa tgaag 25

<210> SEQ ID NO 391
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 391
gttgaccacc tacataccaa atacgctcct ga 32

<210> SEQ ID NO 392
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
cgagagtcag gtacggcggt cagtagtttg ttactcgtca gaaaatcgaa 50

<210> SEQ ID NO 393
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
tgcgctggta ataagacgac caggaatt 28

<210> SEQ ID NO 394
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
gttaatcgag cggcatggtc aatattaaca ccaaacgtga 40

<210> SEQ ID NO 395
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
tctcctcact accatgaaca aaatgtaatc cacgctcttt 40

<210> SEQ ID NO 396
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
ggaagacggc agcaataaac agtagttgaa agtaca 36

<210> SEQ ID NO 397
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
taaaaagtga gagcgcgaag gagtcaagga ag 32

<210> SEQ ID NO 398
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
taaaatgtca acaaaccaat ccaagagaat cttccaac 38

<210> SEQ ID NO 399
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
atcatcttat tagggttagc ctcggcatcc acggcgcttt gtatcagg 48

<210> SEQ ID NO 400
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
gcgtcagcga aacgcagttt ttgacatatc ctacaaagtc caagca 46

<210> SEQ ID NO 401
<211> LENGTH: 36
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401

gtggagcttg cagacccata tcgttctcta acccag                          36


<210> SEQ ID NO 402
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402

agatgaaacc atttttgaat ctctcaga                                   28


<210> SEQ ID NO 403
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403

cggtcgtcag agtgtcaaaa acgatcatca aaagtggagg                      40


<210> SEQ ID NO 404
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404

ataactccaa agcagcctga aacaaagtca tttggcgaga aaagat               46


<210> SEQ ID NO 405
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405

ttgaacacag agggcgcggc aaaagtggtc ta                              32


<210> SEQ ID NO 406
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406

agcagcctta tggccgtcaa ggagcacatc gg                              32
```

<210> SEQ ID NO 407
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 407
cagaagcctg aatgagggaa accataacga gcattcaa 38

<210> SEQ ID NO 408
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 408
ttgagttgcg tagccatggc agcaacctta atagaggcca aagcggtctg 50

<210> SEQ ID NO 409
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 409
ttatagatat catcttgatt aagcgttaaa tccaaaacgg 40

<210> SEQ ID NO 410
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 410
gaaacgtatc ggcgtgtgaa tcataccctc ggcagcaaga cctctaat 48

<210> SEQ ID NO 411
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
gactcatgat ttcttaacca tactcaggca cacgaaaa 38

<210> SEQ ID NO 412
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 412
ccaactgcgc cgccaaggga agtacgtg 28

<210> SEQ ID NO 413
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 413
tagtcatgga accgcacgca aagcatggtc aacgctacct gtcgac 46

<210> SEQ ID NO 414
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 414
caatatcaca aaaatactga tagcgattgt tcagtaactt 40

<210> SEQ ID NO 415
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 415
gactcagaga ctcatatcta aaccgaacgt gccaagcata gaaaggtc 48

<210> SEQ ID NO 416
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
gacagatttg tcattgtgag tgcgttctct ac 32

<210> SEQ ID NO 417
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
gacctttaac tggcggcgat tcgtcacagg tagcca 36

<210> SEQ ID NO 418
<211> LENGTH: 32

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 418
atcagaaaat acgccacgcg cataactttt cc 32

<210> SEQ ID NO 419
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
gacggttgac agtccccatt agctgtccta ttagtggttg aacagcatcg 50

<210> SEQ ID NO 420
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
gcaaagtaga gctgcgcaag gatacgattt aatcaagata 40

<210> SEQ ID NO 421
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
aagcatgtca atgctcagtc tctttttcat cttcacacta ct 42

<210> SEQ ID NO 422
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
ttacctccaa atgaagaata attattcatc ttcacactac t 41

<210> SEQ ID NO 423
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
gacgggatac aattcagctc gacgtttttg actcatcttc acactact 48

<210> SEQ ID NO 424
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
ggcgctgcgt aaccgtcttc ctctacgcaa tatcatcttc acactact 48

<210> SEQ ID NO 425
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 425
taaggccaaa gcggctaggc cacagcaagg tctcatcttc acactact 48

<210> SEQ ID NO 426
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 426
caatggcgcc aggcaatgga tcatcttcac actact 36

<210> SEQ ID NO 427
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 427
ccagcgccag cgataaccgg atccactgct actcatcttc acactact 48

<210> SEQ ID NO 428
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 428
ttaagcgagc gccagaacgt tttttaccga acgtcactca agtatcatct tcacactact 60

<210> SEQ ID NO 429
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 429
actcgcgaca gcttggtttt tagtgagttt tagccataac ccagtcatct tcacactact 60

<210> SEQ ID NO 430
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
tatcgtgttt cccgcaaggt aaacgcgaga acataaccat tcatcttcac actact 56

<210> SEQ ID NO 431
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
cttatcaaca gggcgtacca gagtcatcat cttcacacta ct 42

<210> SEQ ID NO 432
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432
acgttccaag agctcaaaga aacgcggcca tcaacactca gtaatcatct tcacactact 60

<210> SEQ ID NO 433
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
agtaaatttg agcagatttg agtaattcag tgtcatcttc acactact 48

<210> SEQ ID NO 434
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
ttaataatgt tttccgtaaa ggccatcatc ttcacactac t 41

<210> SEQ ID NO 435

<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
actttcatag ccagattaga gcgcatgagc aaattaaacg tcatcttcac actact 56

<210> SEQ ID NO 436
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
tcgggcttca ataaactctg tcatcttcac actact 36

<210> SEQ ID NO 437
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
ttaacgtatg ttccatcttt agcacttggt aagttggatt tcgctcatct tcacactact 60

<210> SEQ ID NO 438
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
gtcagttcac agaatgacac gacccagata caaactcatc attatcatct tcacactact 60

<210> SEQ ID NO 439
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
gctaaaaatt aggagcctgt cgcattgcaa ccaacccgat gggctcatct tcacactact 60

<210> SEQ ID NO 440
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
gtcagtaatt tagacagcac gtaaaggggc cgaagcccct aatttcatct tcacactact 60

<210> SEQ ID NO 441
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
caatagcgag ggtccgccag cagtccactc gaatttagac aggctcatct tcacactact 60

<210> SEQ ID NO 442
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
ccctttgtag caatcgcgaa tcatcttcac actact 36

<210> SEQ ID NO 443
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
aagctagaag tcgtcgggag aggagtggac cagtagatga agtatcatct tcacactact 60

<210> SEQ ID NO 444
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444
cagttgcgta ccaggaagtg cttctgtcat cttcacacta ct 42

<210> SEQ ID NO 445
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
aaccagaacg tgaaaaagtg gaagctcatc ttcacactac t 41

<210> SEQ ID NO 446
<211> LENGTH: 48
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 446
gtcagtatca agtaaacata agagagaaaa cttcatcttc acactact 48

<210> SEQ ID NO 447
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
gtcgcataga aatataactg gtagctttcg tattttgcga tcatcttcac actact 56

<210> SEQ ID NO 448
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
cctacgagtc agtccttggg gataacatca tggtgcat 38

<210> SEQ ID NO 449
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
cctacgagtc agtcctcctt tcaacgtgag ccaggaggaa gcggatgttt 50

<210> SEQ ID NO 450
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
cctacgagtc agtcctgata atctggttga acggcgaagc 40

<210> SEQ ID NO 451
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
cctacgagtc agtcctactc ttgtgccaat tcatccacga 40

<210> SEQ ID NO 452
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 452
cctacgagtc agtcctagta taaagaaatg ccaacgcaag cctccgagca 50

<210> SEQ ID NO 453
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 453
cctacgagtc agtcctttaa tccttctcag agcgcataaa gtgcaatgaa 50

<210> SEQ ID NO 454
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 454
cctacgagtc agtcctaagt tgggcataca tacaacgccc tgcatacgaa aagacacgtc 60

<210> SEQ ID NO 455
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 455
cctacgagtc agtcctcatg cggcagacga gcttagtacc tcgcaacggc tgcggacgac 60

<210> SEQ ID NO 456
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 456
cctacgagtc agtcctcgac tttgaatatt agacatgcaa 40

<210> SEQ ID NO 457
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 457
cctacgagtc agtccttctc ttttcatttt cacattctga ttctgaacag cttcttaacg 60

<210> SEQ ID NO 458
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 458
cctacgagtc agtcctactg atcagcattg ggattatcat aaaacatacg ac 52

<210> SEQ ID NO 459
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 459
cctacgagtc agtcctcgtc acgtcctgcg tgtagcaa 38

<210> SEQ ID NO 460
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 460
cctacgagtc agtccttatc cttatcatcc ttgatttcat cgctgaatag ca 52

<210> SEQ ID NO 461
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 461
cctacgagtc agtcctgatg tctcatttga atcgttagtt gatgaagcca ct 52

<210> SEQ ID NO 462
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 462
cctacgagtc agtcctcagg ttggtatccg aactgcttta ttcgtaaaca ag 52

<210> SEQ ID NO 463
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 463
cctacgagtc agtcctctgc tgttaacatg cttagggatt ttataatagt tg 52

<210> SEQ ID NO 464
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 464
cctacgagtc agtcctgaaa gacgaaaaat gtttcaccat atccttcatg aa 52

<210> SEQ ID NO 465
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 465
cctacgagtc agtcctatag caattcagcg cctttaag 38

<210> SEQ ID NO 466
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 466
gttcagaaaa ctggcctaac cactgcaaca agaaaa 36

<210> SEQ ID NO 467
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 467
gcgtcacctg aaacaataag aggttttgaa gaaataacat catggtaacg 50

<210> SEQ ID NO 468
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 468
aaagcggcat agatattcaa ataagtacgg tcaggcatcc 40

```
<210> SEQ ID NO 469
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469

aggcgctgaa cggacttcat agaagcgc                                          28


<210> SEQ ID NO 470
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470

tataacgtgc tttaggtgtc tgtagaacca gcaataaaag                             40


<210> SEQ ID NO 471
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471

ctgcatgaat atcagcacca acagattagc ggcgttgaca tatcaaaa                    48


<210> SEQ ID NO 472
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472

acggcgcttt accaaatacc taaatagttg ttatggtc                               38


<210> SEQ ID NO 473
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473

ttaaactcaa aattttacat taaaatcatg gt                                     32


<210> SEQ ID NO 474
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 474
aatatgacgg taaagaacca gtagtgtcat agccagatgc ccgtca 46

<210> SEQ ID NO 475
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 475
ataacgatac cactgaccct aatcaccatg gt 32

<210> SEQ ID NO 476
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 476
agaaaaaccg gtcggaccac cattaccatc caaaggataa acccac 46

<210> SEQ ID NO 477
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 477
tctgaatggg gtcggcatca aaagtaatca cgttcttggt 40

<210> SEQ ID NO 478
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 478
accaaaaacc atttttgaat ctctcaga 28

<210> SEQ ID NO 479
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 479
cagcaagaca atatcacgaa aatataatcg gtaaccaacc 40

<210> SEQ ID NO 480
<211> LENGTH: 38
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 480
cagtatgcaa attagcacag gcaaaaaatt tacaatga 38

<210> SEQ ID NO 481
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 481
catcacacag tccttgacgg tcgttctcta atccgc 36

<210> SEQ ID NO 482
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 482
ctgtcgcacc tccagccggc aaaagtggtc ta 32

<210> SEQ ID NO 483
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 483
actcagaaga gaaataagcg aaccaaataa gcagcttgca gacccataat 50

<210> SEQ ID NO 484
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 484
agcagcctta tggccgtcaa ggagcacatc gg 32

<210> SEQ ID NO 485
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
gtcaatagta aagtgcaccg catgcggcca ttagctgtac accctcgg 48

<210> SEQ ID NO 486
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486 taccettgaa agtgggacga ccaaaaagtc tcaggaggaa gcggagcagt 50

<210> SEQ ID NO 487
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 487
tgcggtgaaa aagcgtcctg agcgcgcata aacgta 36

<210> SEQ ID NO 488
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 488
cacacaaact gtaggaagtg tccggtggta gaagtcgtca 40

<210> SEQ ID NO 489
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 489
gataggtcgt agtaatggat acgcgcgccg cc 32

<210> SEQ ID NO 490
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 490
gatagcggcg actggcagtc ggcgtgactg taaccataag gcgaac 46

<210> SEQ ID NO 491
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 491
tctaaaccga acgtgccaag catagacaga atagcttctc 40

<210> SEQ ID NO 492
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 492
tggtaagttg gattaagcac cccagcctca ca 32

<210> SEQ ID NO 493
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 493
tttggcgaga aagctcttag ggtcaacgct acaatact 38

<210> SEQ ID NO 494
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 494
tgttaatttg agcagactca ttctagct 28

<210> SEQ ID NO 495
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 495
ccaaatgttg atttcttacc tattcagcat cggactcaga gactcata 48

<210> SEQ ID NO 496
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 496
gttagcctct gaaacaaatg cttatggtat cagggttaat gtggcatt 48

<210> SEQ ID NO 497
<211> LENGTH: 46

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 497
gtcaaatgag cctgacaaga gaatctatcg aaatcatctt cgtgtt 46

<210> SEQ ID NO 498
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 498
tttcttctgc gtcagtaaga accagggcct tt 32

<210> SEQ ID NO 499
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 499
ggaaaccata acgagctgga aacgtacgga tttaaaat 38

<210> SEQ ID NO 500
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 500
acggcgtcac caatctgccg aagcttgcct tt 32

<210> SEQ ID NO 501
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 501
cgctctttgt tcagtaactt gactttgaga tggcagcaac 40

<210> SEQ ID NO 502
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 502

```
agaggtttat gggatccaaa gcggtcatca tcttgattaa gctcattagg              50


<210> SEQ ID NO 503
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503

aacaccatct taatccactg ttcaatgtct acgagaaaga                         40


<210> SEQ ID NO 504
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504

cggcaacata ccaaaggcgg ctttacgt                                      28


<210> SEQ ID NO 505
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505

actcagcggt cagtagcaat gttgaccacc tgcaat                             36


<210> SEQ ID NO 506
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506

cagcaaggta gcgacagttg ttccttgaac ggcgtcgcgt ctgc                    44


<210> SEQ ID NO 507
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507

agcaccaaac ttgttaaatc ccagcg                                        26


<210> SEQ ID NO 508
<211> LENGTH: 44
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 508

gtactgaata caaaactcgg tatagataag caggagaaac aagc                44


<210> SEQ ID NO 509
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509

caacaggcgc gaatatcttt ttggattctt ta                             32


<210> SEQ ID NO 510
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510

gcgcgagcgc caaaatggta                                           20


<210> SEQ ID NO 511
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511

tctttaatcc agcaatcacc tcaccagata caaactcatc atta                44


<210> SEQ ID NO 512
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512

gaacatgggc atattatcat aaaacgccca cgcaaaaagc ggct                44


<210> SEQ ID NO 513
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513

gaagatttca cgcggcggca agttgccatc tctttaaaga aggtcat             47


<210> SEQ ID NO 514
```

```
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514

gtacggggtg aatcgcaatc ttttttaagt gg                                32


<210> SEQ ID NO 515
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515

aagtgacgtt tgagagatta ccgcgc                                       26


<210> SEQ ID NO 516
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516

acgaagtagc ggtaaagtag cctct                                        25


<210> SEQ ID NO 517
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517

cttcgtcgca gtcgaacaag cggcgccatc tgttgacagg                        40


<210> SEQ ID NO 518
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518

tttatagggt ttgaattcat gcggagtcaa ag                                32


<210> SEQ ID NO 519
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
```

agtcatggcg acctggagta acagaagtac aggtgccata aaca 44

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 520
acacgaaggc ggctcagcgg 20

<210> SEQ ID NO 521
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 521
tccgacagga gcaggaaacg gagta 25

<210> SEQ ID NO 522
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 522
actttcagcg aaggcattta gtcatgataa ggacgtgaaa 40

<210> SEQ ID NO 523
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 523
ttcatgactt tttttagcca tactcatcca caaccagtag 40

<210> SEQ ID NO 524
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 524
cgggatgaaa tgttttttcc atgaccttct gcacgtaatt taga 44

<210> SEQ ID NO 525
<211> LENGTH: 26
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 525

gcgacgtgta gccacgtatt cgccag                                          26


<210> SEQ ID NO 526
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526

ggttcaatca tttttatcga aaggtcgctc at                                   32


<210> SEQ ID NO 527
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527

acgctcgcaa gagtaaactt ggtca                                           25


<210> SEQ ID NO 528
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528

aattacatag aaaccaacca cttcg                                           25


<210> SEQ ID NO 529
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529

gacccatcaa cagggacata aaaagtaaat aaacgtaaga aacg                      44


<210> SEQ ID NO 530
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530

acgcaaccgg acgctcgacg ccattaatac ataataacat cactata                   47
```

<210> SEQ ID NO 531
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 531
cctcaacgac ttctgccatc agaatgagac ag 32

<210> SEQ ID NO 532
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 532
cgaggtcaga aatccaacgc gtcagtttaa gccactcagc gtac 44

<210> SEQ ID NO 533
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 533
tgagtataat aaatcatagg ctgaat 26

<210> SEQ ID NO 534
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
acccgattct gaacagcttc ttgggaagtc catatcatat ctggggt 47

<210> SEQ ID NO 535
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 535
cattagcaat gaaaactcaa aagtgttaca gcgacgacaa 40

<210> SEQ ID NO 536
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 536 cccttttgtag cagatttcat 20

<210> SEQ ID NO 537
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 537
tcgtcaatct caaattcgta 20

<210> SEQ ID NO 538
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 538
ggcgctgcgt aaccgtcttc agtgtcaaat ca 32

<210> SEQ ID NO 539
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 539
acgttccaag agctcagaag caataccgaa cctgatctca gtaaatc 47

<210> SEQ ID NO 540
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 540
catatttaac ctgactattc ttgaattaaa aa 32

<210> SEQ ID NO 541
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 541
acgcccctgc aattaaaatt aggccacgag ga 32

<210> SEQ ID NO 542
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 542
acccttcctg aatgaatggg atac 24

<210> SEQ ID NO 543
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 543
acgcttgtgc caattcatcc acga 24

<210> SEQ ID NO 544
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 544
cagtcagcca tataactgac ca 22

<210> SEQ ID NO 545
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 545
agtggaggtt gcattcaaac gatacgtcag ccaacg 36

<210> SEQ ID NO 546
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 546
agcaatagac caaaccatca at 22

<210> SEQ ID NO 547
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 547
ttcgcatagt gccatgctac ac 22

<210> SEQ ID NO 548
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 548
gtcgcaaatg aaccttcaac ggcagaagct taat 34

<210> SEQ ID NO 549
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 549
aacgcagacg acaccattcg ggagggtaaa gaag 34

<210> SEQ ID NO 550
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 550
aacaagcaga attttcaaag taagcgttag ttgatg 36

<210> SEQ ID NO 551
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 551
aagttgggca tacatacaac gccctgcata cgaaaagaca cgtc 44

<210> SEQ ID NO 552
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 552
tttcttgttg acagtcccaa gctatttaat tgcg 34

<210> SEQ ID NO 553
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 553
caaaaattct aagcagtggc gagattatca gaaaaa 36

<210> SEQ ID NO 554
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 554
ttcttgcaca gcaatcaatc accagaacgg aaaacatcct ggaa 44

<210> SEQ ID NO 555
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 555
cctagagatg tatgacgcgc atgacaagtt gtca 34

<210> SEQ ID NO 556
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 556
ccaacgaaga agcagcatta accgtcaatg tatcca 36

<210> SEQ ID NO 557
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 557
ctttgcattg ggtgaatcat tagccttgta ctcagg 36

<210> SEQ ID NO 558
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 558
agtctctcct cactaccatg aacaaaatgt aatcca 36

<210> SEQ ID NO 559
<211> LENGTH: 24
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 559
attttctctc tttttgcgtt cgta 24

<210> SEQ ID NO 560
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 560
ataagacgca tctcgaacgc aatgagtaga gtcaat 36

<210> SEQ ID NO 561
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 561
taactttttc cgtggaagca ttttcatccc gaagttgcgg tttg 44

<210> SEQ ID NO 562
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 562
tgcggacgac gtcagtcgca aggtaaacgc gaacaattca acga 44

<210> SEQ ID NO 563
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 563
gttggaacgt tttttacctt tttg 24

<210> SEQ ID NO 564
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 564
ataacgcgag ggtatcctag ca 22

<210> SEQ ID NO 565
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 565
aacagacgat gattaacagt cgggagagtg ccaaga 36

<210> SEQ ID NO 566
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 566
ccgcttcggc gttataacct cacac 25

<210> SEQ ID NO 567
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 567
catggaagcg ataaaactct gcagg 25

<210> SEQ ID NO 568
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 568
tcttgaacac tcatccttaa tacct 25

<210> SEQ ID NO 569
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 569
ctgctttatc aagataattt ttcga 25

<210> SEQ ID NO 570
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 570
ttaagagggc gttcagcagc cagct 25

<210> SEQ ID NO 571
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 571
tagacataat ttatcctcaa gtaag 25

<210> SEQ ID NO 572
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 572
gtggtcggca gattgcgata aacgg 25

<210> SEQ ID NO 573
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 573
ccagcaagga agccaagatg ggaaa 25

<210> SEQ ID NO 574
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 574
ggactgactc gtagg 15

<210> SEQ ID NO 575
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 575
agtagtgtga agatg 15